US008088749B2

(12) United States Patent
Simeone et al.

(10) Patent No.: US 8,088,749 B2
(45) Date of Patent: Jan. 3, 2012

(54) COMPOSITIONS AND METHODS FOR TREATING CANCER

(75) Inventors: Diane Simeone, Ann Arbor, MI (US); Mats Ljungman, Ann Arbor, MI (US); Liang Xu, Ann Arbor, MI (US); Lidong Wang, Ann Arbor, MI (US); Fengtian He, Chongqing (CN)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/333,559

(22) Filed: Dec. 12, 2008

(65) Prior Publication Data
US 2009/0192112 A1    Jul. 30, 2009

Related U.S. Application Data

(60) Provisional application No. 61/013,109, filed on Dec. 12, 2007.

(51) Int. Cl.
*A61K 48/00* (2006.01)
*C07H 21/02* (2006.01)
*C07H 21/04* (2006.01)

(52) U.S. Cl. ... 514/44; 536/23.1; 536/24.31; 536/24.33; 536/24.5

(58) Field of Classification Search .................. None
See application file for complete search history.

(56) References Cited

U.S. PATENT DOCUMENTS
6,749,863 B1    6/2004   Chang

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Duxbury et al., RNA interference targeting focal adhesion kinase enhances pancreatic adenocarcinoma gemcitabine chemosensitivity, 2003, biochemical and Biophysical Research Communications, 311, pp. 786-792.*
International Search Report mailed Mar. 26, 2009 for PCT/US2008/086669.
Bafico, A. et al., (2004) "An autocrine mechanism for constitutive Wnt pathway activation in human cancer cells." Cancer Cell 6, 497-506.
Brzoska PM et al., "The product of the ataxia-telangiectasia group D complementing gene, ATDC, interacts with a protein kinase C substrate and inhibitor." 1995 Proc Natl Acad Sci 92 7824-7828.
Cao D. et al., "Identification of novel highly expressed genes in pancreatic ductal adenocarcinomas through a bioinformatics analysis of expressed sequence tags" 2004 Cancer Biol There 3 1081-1089.

Chen R. et al., "Pancreatic Cancer: Novel Approaches to Diagnosis and Therpy" 2005 Gastroenterol. 129 1344-1347.
Choi EK et al., "Effect of Protein Kinase C Inhibitor (PKCI) on Radiation Sensitivity and c-fos Transcription" 2000 Int J Radiat Onco Biol Phys 49 397-405.
Crnogorac-Jurcevic T. et al., "Molecular alterations in pancreatic carcinoma: expression profiling shows that dysregulated expression of S100 genes is highly prevalent." 2003 J. Pathol. 201 pp. 63-74.
Dyrskjot L. et al., "Gene expression in the urinary bladder: a common carcinoma in situ gene expression signature exists disregarding histopathological classification." 2004 Cancer Res. 64 4040-8.
Ernst T, et al. (2002) "Decrease and gain of gene expression are equally discriminatory markers for prostate carcinoma: a gene expression analysis on total and microdissected prostate tissue." Am J Pathol 160, 2169-2180.
Ewald B et al., "H2AX phosphorylation marks gemcitabine-induced stalled replication forks and their collapse upon S-phase checkpoint abrogation." 2007 Mol Cancer Ther 6 1239-1248.
Glebov, O. K., et al (2006) "Gene expression patterns distinguish colonoscopically isolated human aberrant crypt foci from normal colonic mucosa." Cancer Epidemiol Biomarkers Prev 15, 2253-2262.
Greenlee et al., "Cancer statistics, 2001" 2001 CA Cancer J. Clin., 51 pp. 15-36.
Gregorieff, A., and Clevers, H. (2005). "Wnt signaling in the intestinal epithelium: from endoderm to cancer." Genes Dev 19, 877-890.
Hawes et al., "A multispecialty approach to the diagnosis and management of pancreatic cancer." 2000 Am. J. Gastroenterol. 95 pp. 17-31.
Hawthorn, L. et al. (2006) "Characterization of cell-type specific profiles in tissues and isolated cells from squamous cell carcinomas of the lung." Lung Cancer 53, 129-142.
Hosoi Y et al., "Expression of a candidate ataxia-telangiectasia group D gene in cultured fibroblast cell lines and human tissues." 1994 Radiat Biol 66 S71-S76.
Hruban RH et al., "Progression model for pancreatic cancer." 2000 Clin Cancer Res 6 2969-2972.
Iacobuzio-Donahue CA et al., "Highly expressed genes in pancreatic ductal adenocarcinomas: a comprehensive characterization and comparison of the transcription profiles obtained from three major technologies." 2003 Cancer Res 63 pp. 8614-8622.
Jemal A. et al., "Cancer statistics, 2005." 2005 CA Cancer J Clin 55 pp. 10-30.
Jemal et al., "Cancer statistics, 2003." 2003 CA Cancer J Clin 53 pp. 5-26.
Kapp LN et al., "Stable radioresistance in ataxia-telangiectasia cells containing DNA from normal human cells." 1989 Int J Radiat Biol 56 667-675.
Kapp LN et al., "Cloning of a candidate gene for ataxia-telangiectasia group D." 1992 Am J Human Genet 51 45-54.
Kosaka, Y. et al, (2007) "Tripartite motif-containing 29 (TRIM29) is a novel marker for lymph node metastasis in gastric cancer." Ann Surg Oncol 14, 2543-2549.
La Tulippe et al., "Comprehensive Gene Expression Analysis of Prostate Cancer Reveals Distinct Transcriptional Programs Associated with Metastatic Disease" 2002 Cancer Res 62 4499-506.

(Continued)

*Primary Examiner* — Amy Bowman
(74) *Attorney, Agent, or Firm* — Casimir Jones, S.C.

(57) ABSTRACT

The present invention relates to therapeutic targets for cancer. In particular, the present invention relates to small molecules and nucleic acids that target ATDC (TRIM29) expression in cancer with ATDC overexpression.

9 Claims, 45 Drawing Sheets

OTHER PUBLICATIONS

Laderoute KR et al., "Expression of the ATDC (ataxia telangiectasia group D-complementing) gene in A431 human squamous carcinoma cells." 1996 Int J Cancer 66 772-778.

Leonhardt EA et al., "Nucleotide sequence analysis of a candidate gene for ataxia-telangiectasia group D (ATDC)." 1994 Genomics 19 130-136.

Logsdon CD et al., "Molecular profiling of pancreatic adenocarcinoma and chronic pancreatitis identifies multiple genes differentially regulated in pancreatic cancer." 2003 Cancer Res. 63 pp. 2649-2657.

Luo J et al., "Human prostate cancer and benign prostatic hyperplasia: molecular dissection by gene expression profiling." 2001 Cancer Res 61 4683-8.

Lustig, B., and Behrens, J. (2003). "The Wnt signaling pathway and its role in tumor development." J Cancer Res Clin Oncol 129, 199-221.

Mutter GL et al., "Gene Expression Profile in Endometrioid Endometrial Carcinoma" 2004 Gynecol Oncol 83 175-176.

Mutter, G. L. et al., (2001) "Global expression changes of constitutive and hormonally regulated genes during endometrial neoplastic transformation." Gynecol Oncol 83, 177-185.

Nacht M et al. (1999) "Combining serial analysis of gene expression and array technologies to identify genes differentially expressed in breast cancer." Cancer Res 59, 5464-5470.

Ohmachi, T. et al., (2006) "Clinical significance of TROP2 expression in colorectal cancer." Clin Cancer Res 12, 3057-3063.

Pasca Di Magliano, M. et al. (2007) "Common activation of canonical wnt signaling in pancreatic adenocarcinoma." PLoS ONE 2, e1155.

Reymond A et al., "The tripartite motif family identifies cell compartments." 2001 Embo J 20 2140-2151.

Santin, A. D. et al., "Gene expression profiles in primary ovarian serous papillary tumors and normal ovarian epithelium: identification of candidate molecular markers for ovarian cancer diagnosis and therapy." 2004 Int J Cancer 112, 14-25.

Savitsky K et al., "A single ataxia telangiectasia gene with a product similar to PI-3 kinase." 1995 Science 268 1749-1753.

Shinozaki T et al., "Functional role of Mdm2 phosphorylation by ATR in attenuation of p53 nuclear export." 2003 Oncogene 22 8870-8880.

Smith, A. P., et al. (2005). "Whole-genome expression profiling of the melanoma progression pathway reveals marked molecular differences between nevi/melanoma in situ and advanced-stage melanomas." Cancer Biol Ther 4, 1018-1029.

Su T et al., "Deletion of histidine triad nucleotide-binding protein 1/PKC-interacting protein in mice enhances cell growth and carcinogenesis." 2003 Proc Natl Acad Sci 100 7824-7829.

Tauchi H et al., "Altered splicing of the ATDC message in ataxia telangiectasia group D cells results in the absence of a functional protein." 2000 Mutagenesis 15 105-108.

Tibbetts RS, "Functional interactions between BRCA1 and the checkpoint kinase ATR during genotoxic stress." 2000 Genes Dev 14 2989-3002.

Weiske J et al., "The fate of desmosomal proteins in apoptotic cells." 2001 J Biol Chem 281 41175-41181.

Weiske J et al., "The histidine triad protein Hint1 interacts with Pontin and Reptin and inhibits TCF-beta-catenin-mediated transcription." 2005 J Cell Science 118 3117-3129.

Yeo et al., "Six hundred fifty consecutive pancreaticoduodenectomies in the 1990s: pathology, complications, and outcomes." 1997 Ann. Surg. 226 pp. 248-257.

Yu YP et al., "Gene Expression Alterations in Prostate Cancer Predicting Tumor Aggression and Preceding Development of Malignancy" 2004 J Clin Oncol 22 2790-2799.

Zeng G et al., (2006) "Aberrant Wnt/b-catenin signaling in pancreatic adenocarcinoma." Neoplasia 8, 279-289.

Zhan, F., et al. "Global Gene Expression Profiling of Multiple Myeloma, Monoclonal Gammopathy of Undetermined Significance, and Normal Bone Morrow Plasma Cells" (2002) Blood 99, 1745-1757.

Zhang, P., et al. (2006) "Identification of genes associated with cisplatin resistance in human oral squamous cell carcinoma cell line." BMC Cancer 6, 224.

Ziv Y et al., "Chromatin relaxation in response to DNA double-strand breaks is modulated by a novel ATM- and KAP-1 dependent pathway." 2006 Nature Cell Biol 8 870-876.

Zou L, "Sensing DNA damage through ATRIP recognition of RPA-ssDNA complexes." 2003 Science 300 1542-1548.

* cited by examiner

Figure 16
A.
B.
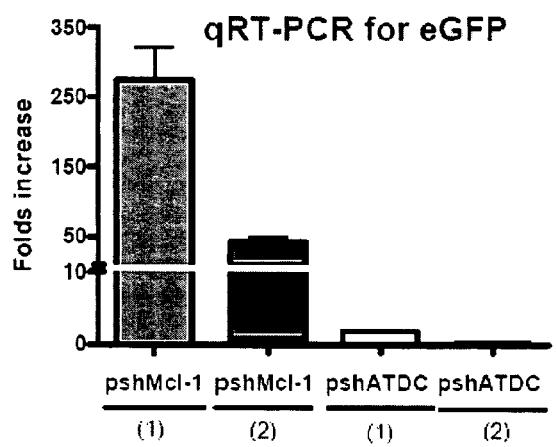
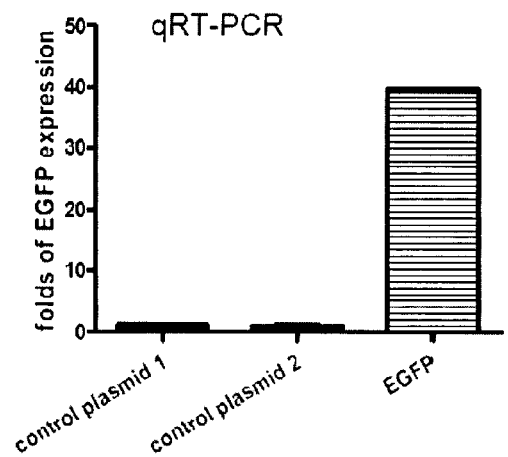
Note: EGFP expression was normalized by β-actin, the mean value of EGFP expression in pshATDC was defined as 1.

Figure 19

SEQ ID NO:01

```
   1 gacgcctgcc agaaaggtca cctatcctga acccagcaa gcctgaaaca gctcagccaa
  61 gcaccctgcg atggaagctg cagatgcctc caggagcaac gggtcgagcc cagaagccag
 121 ggatgcccgg agccgtcgg gcccagtgg cagcctggag aatggcacca aggctgacgg
 181 gaaggatgcc aagaccacca acgggcacgg cggggaggca gctgagggca agagcctggg
 241 cagcgccctg aagccaggt aagtaggag cgccctgttc gcgggcaatg agtggcggcg
 301 accatcatc cagtttgtcg cgacaagagt ccaaactact tccaactact tcagcatgga
 361 ctctatggaa gcaagaggt cgccgtacgc agggctccag ctgggggctg ccaagaagcc
 421 accgttacc tttgccgaaa agggcgagct gcgcaagtcc atttctcgg agtcccgaa
 481 gccacggtg tccatcatgg agccggggga gacccgcgg aacagctacc ccgggccga
 541 cacgggcctt ttttcacggt ccaagtcctg ctcgaggag gtgcgtgcg actcctgcat
 601 cggcaacaag cccacctgg tcaagtcctg aaggcgccgc caggcctcct tctgcagct
 661 gcatctcaag ccccacctgg agggcgccgc cttccagcaa caccagctgc tcgagcccat
 721 ccctacttgc agtgcccgca agtgtccgt gctaccttg gcatgccaag acgatggagc tctttctgcca
 781 gaccaccag acctgcatct gctacctttg catgttccag gagcacaaga atcatagcac
 841 cgtgacagtg gaggagccca aggccgagaa ggaccggag ctgtcactgc aaaagaggca
 901 gctgcagctc aagatcattg agattgagaa tgaagctgag aagtgcaga agagaaagga
 961 ccgcatcaag agcttcacca ccaatgagaa ggcatcctg gagcagaact tccggacct
1021 ggtgcgggac ctggagaagc aaaaggagga agtgaggget gcgctggagc agcgggagca
1081 ggatgctgtg gaccaagtga agtgatcat ggatgctctg gatgagagag ccaagtgct
1141 gcatgaggac aagcagaccc gggagcagct gcatagcatc agcgactctg tgttgttttct
1201 gcaggaattt ggtgcattga tgagcaatta ctctctcccc ccaccccctgc ccacctatca
1261 tgtcctgctg gaggggagg gcctgggaca gtcactaggc aacttcaagg acgacctgct
1321 caatgtatgc atgcgccacg ttgagaagat gtgcaaggcg gacctgagcc gtaacttcat
1381 tgagaggaac cacatggaga acgtgtga ccatcgctat gtgaacaact acacgaacag
1441 cttcgggggt gagtggagtg caccggacac catgaagaga tactccatgt acctgacacc
1501 caaagtggg gtccggacat cataccagcc ctcgtctcct ggccgcttca ccaaggagac
1561 caccagaag aattcaaca atctctatgg caccaaaggt aactacacct ccgggtctg
1621 ggagtactcc tccagcattc agaactctga caatgacctg ccgtcgtcc aaggcagctc
1681 ctccttctcc ctgaaaggct atccctcct catgcggagc caaagcccca agcccagcc
1741 ccagacttgg aaatctggca agcagactat gctgtctcac taccggccat tctacgtcaa
1801 caaaggcaac gggattgggt ccaacgaagc cccatgagct cctggcgaa ggaacgaggc
1861 gccacacccc tgctcttcct cctgaccctg ctgctcttgc cttctaagct actgtgctg
1921 tctgggtggg agggagcctg gtcctgcacc tgccctcgc agccctctgc cagcctcttg
1981 gggcagttc cggcctctcc gacttcccca ctggccacac tccattcaga ctccttcct
2041 gccttgtgac ctcagatggt caccatcatt cctgtgctca gaggccaaacc catcacagg
2101 gtgagatagg ttgggggctg gagtaccgc cctaacccg atggtatcag cctgcctctc cctgctgtct
2161 ggctagcagt gagtaccgc atgtatcag cctgcctctc cgcccacgc cctgctgtct
2221 ccaggcctat agacgtttct ctccaaggcc ctatcccca atgttgtcag cagatgcctg
```

Figure 19 (cont.)

```
2281 gacagcacag ccacccatct cccattcaca tggcccacct cctgcttccc agaggactgg
2341 ccctacgtgc tctctctcgt cctacctatc ctctcagtgt aatgcccagc atgcagaaac ctgcagccct
2401 tggccactgc agatggaaac ctcactttgag tctgtggtcc cttgacatca cctacccag gcggtgggtc
2461 tccaccacag ccactttgag tctgtggtcc ctggagggtg gcttctcctg actggcagga
2521 tgacctttagc caagatattc ctctgttccc tctgctgaga taaagaattc ccttaacatg
2581 atataatcca cccatgcaaa tagctactgg cccagctacc atttaccatt tgcctacaga
2641 atttcattca gtctacactt tggcattctc tctggcgatg gagtgtggct gggctgaccg
2701 caaaaggtgc cttacacact gcccccaccc tcagccgttg cccatcaga ggctgcctcc
2761 tccttctgat tacccccat gttgcatatc agggtgctca aggattggag aggagacaaa
2821 accaggagca gcacagtggg gacatctccc gtctcaacag ccccaggcct atggggctc
2881 tggaaggatg ggccagcttg caggggttgg ggagggagac atccagcttg ggctttcccc
2941 tttggaataa accattggtc tgtcaaaaaa aaaaaaaaaa
```

Figure 20

SEQ ID NO:2

MEPGETRRNSYPRADTGLFSRSKSGSEEVLCDSCIGNKQKAVKSCLVCQASFCELHLKPHLEGAAFRDHQLLEPIPTCSARKCPVHGKTMELF
CQTDQTCICYLCMFQEHKNHSTVTVEEAKAEKETELSLQKEQLQLKIIEIEDEAEKWQKEKDRIKSFTTNEKAILEQNFRDLVRDLEKQKEEV
RAALEQREQDAVDQVKVIMDALDERAKVLHEDKQTREQLHSISDSVLFLQEFGALMSNYSLPPLPTYHVLLEGEGLGQSLGNFKDDLLNVCM
RHVEKMCKADLSRNFIERNHMENGGDHRYVNNYTNSFGGEWSAPDTMKRYSMYLTPKGGVRTSYQPSSPGRFTKETTQKNFNNLYGTKGNYTS
RVWEYSSSIQNSDNDLPVVQGSSSFSLKGYPSLMRSQSPKAQPQTWKSGKQTMLSHYRPFYVNKGNGIGSNEAP

Figure 21

SEQ ID NO:03 sense 5'- caccGCGACCCATCATCCAGTTTGTcgaaACAAACTGGATGATGGGTCGC-3'

SEQ ID NO:04 anti-sense 5'- aaaaGCGACCCATCATCCAGTTTGTttcgACAAACTGGATGATGGGTCGC-3'

SEQ ID NO:05 sense 5'-caccGAAGAGCTCCATCGTCTTGCCAcgaaTGGCAAGACGATGGAGCTC-3'

SEQ ID NO:06 anti-sense 5'- aaaaGAGCTCCATCGTCTTGCCAttcgTGGCAAGACGATGGAGCTCTTC-3'

Figure 23 (cont.)
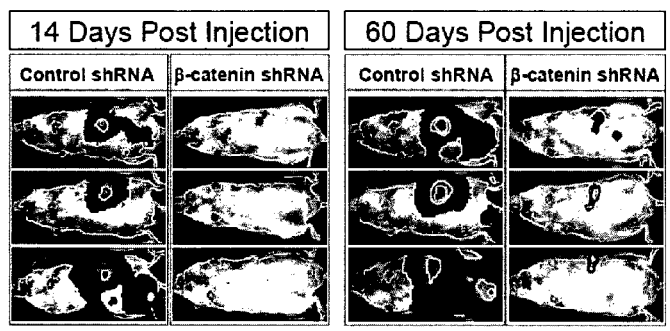
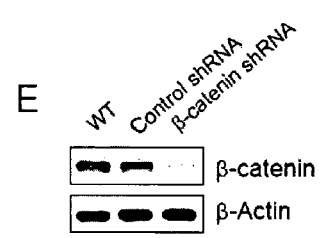
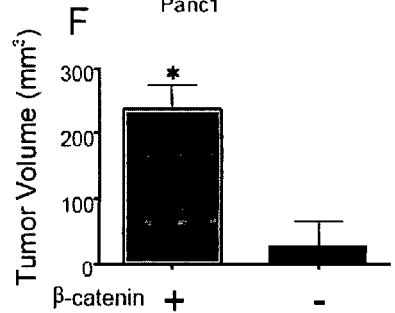

Figure 28

Dvl-2 shRNA1 sense 5'-caccTGTAGCTGCCTTTGTACTCTATTTATTTcgaaAAATAAATAGAGTAACAAAGGCAGCTACA-3' (SEQ ID NO:7)

anti-sense 5'- aaaaTGTAGCTGCCTTTGTTACTCTATTTATTTATTcgAAATAAATAGAGTAACAAAGGCAGCTACA-3' (SEQ ID NO:8)

Dvl-2 shRNA2 sense 5'-caccGGACCGCATGTGGCTCAAGATCACCATCCcgaaGGATGGTGATCTTGAGCCACATGCGGTCC-3' (SEQ ID NO:9)

anti-sense 5'- aaaaGGACCGCAGTGGCTCAAGATCACCATCCttcgGGATGGTGATCTTGAGCCACATGCGGTCC-3' (SEQ ID NO:10)

missense shRNA target sequence (control shRNA)

sense: 5'-caccCAACAAGAGATGAAGAGCACCAAcgaaTTGGTGCTCTTCATCTTGTTG-3' (SEQ ID NO:11)

antisense: 5'-caccCAACAAGATGAAGAGCACCAAcgaaTTGGTGCTCTTCATCTTGTTG-3' (SEQ ID NO:12)

Figure 29

SEQ ID NO:13 (human disheveled 2 (Dvl-2))

```
   1 agtcacgtga catgaggaga ggtggcggg tacctgagg aagctcgcgg cgtcggtggc
  61 ggtggcgcgc ggcggccgct gagaccgggg ctttgagtcg caccccgcg cccgccccc
 121 gccgccaccc tgcagatcc gtgcttttc cccttgctt ctctcccgta ctgggtcagt
 181 cctgtccgcg ctcgcgcgtc ggtttgcggg tgtgcagg cgcggcaggg gccattagcc
 241 ctttggtgg gcggtggagc ccggagcgc gcgggagga ccatgcggg tagcagcact
 301 ggggcggtg gggttgggga gacgaagtg attaccacc tggatgagga agagactccc
 361 tacctgtga agatccctgt ccccgccgag cgcatcaccc tcggcgattt caagagcgtc
 421 ctgcagcggc ccgcggcgc caagtacttt ttcaagtcta tggatcagga tttcgggtg
 481 gtgaaggaag aaattcaga tgacaacgc cgcctcccct gcttcaacg aagggtgta
 541 tcctgctgg tgtcctcaga taatcccaa cccgagatgg cccttccagt ccatgagcct
 601 cgggcagaac tggcgcctcc agccccacct ttacctcctt tgccacccga gaggaccagc
 661 ggcattgggg actcaaggcc tccatcctc cacctcagta tgtccagcag ggctgagaat
 721 ctggagcctg agacagaaac cagtcagta gtgtcactga gcgggagcg gcctgcagg
 781 agagacagca gtgagcatgg cgctgggggc cacaggactg gtggcccctc aaggctggag
 841 cgccacctgg ccggatacga gagctcctct accctcatga ccagcgagct ggagagtacc
 901 agcctggggg actcggacga ggaggacacc atgagcaggt tcagcagctc cacggagcag
 961 agcagtgcct cccgcctcct taagcgccac cggccggcgaa ggaagcagag gccaccccgc
1021 ctggagagga cgtcatcctt cagcagcgtc acagattcca caatgtctct caatatcatc
1081 acagtcacgc taaacatgga gaagtacaac ttcctgggta tctccattgt tggccagagc
1141 aatgagcggg agagcggagg catctacatt ggctccatca tgaagggtgg ggctgtggcg
1201 gccgacgggc gcattgagcc ctgagcgcg agggacatg ctttgcagg tgaatgacat gaactttgag
1261 aacatgagca acatgagcga ctgtgggtg ctgaggaca ttgtgcacaa gcctgcccc
1321 attgtgctga ctgtgccaa gtgctggat cccctctc agccctattt cactctcccc
1381 cgaaatgagc ccatccagcc aattgaccct gctgcctggg tgtccattc cgcggctctg
1441 actgccacct tcccagccta tcccagttcc tcctccatga gcaccattac atctggatcg
1501 tctttgcctg atgctgtga agccggggt ctctccgtcc atacggacat ggcatcggtg
1561 accaagcca tgcagctcca agagtctga ctggaagtcc gggaccgcat gtggctcaag
1621 atcaccatcc ctaatgcctt tctgggctcg gatgtggttg actggctcta ccatcacgtg
1681 gagggctttc ctgagcggcg ggagcccgc aagtatgcca gcgggctgct caaagcaggc
1741 ctgatccgac acaccgtcaa caagatcacc ttctctgagc agtgctatta cgtcttcgga
1801 gacctcagtg gtgctgtga cttcagacca gagctaccta gctcctctgt ctcaatga caacgatggc
1861 tccagtgggg cttcagacca ggataccctg gctcctctgc ccccacac ccctgccac
1921 ctgctgccca cttctcctcta ccaatacct gcccacacc cctacaccc gcagctcca
1981 ccctaccatg agctttcatc ttacacctat ggtggggca gtgccagcag ccagcatagt
2041 gagggcagcc ggagcagtgg gtcgacacgg agtgatgggg ggcaggcg cacggggagg
2101 cccgaggagc gggccccga gtccagtcc gtcagtggca gtgagtctga gccctccagc
```

Figure 29 (cont.)

```
2161 cgaggggca gccttcggcg gggtggggaa gcaagtggga ctagcgatgg gggccctcct
2221 ccatccagag gctcaactgg gggtgcccct aatctccgag cccacccagg gctccatccc
2281 tatggaccgc cccctggcat ggccctcccc tacaacccca tgatggtggt catgatgccc
2341 ccacctccac ctccagtccc tccagcagtg cagcctccgg gggccctcc agtcagagac
2401 ctgggctctg tgccccaga actgacagcc agccgccaaa gcttccacat ggccatgggc
2461 aatcccagcg agttcttttgt ggatgttatg tagcccactg tggggccagg ctgggccggg
2521 cgctcctggt gtgactgg gtgtcctggc cgtcatgtgc ttgctcttac agtgcctggg
2581 ctcagcctac cagctgctgc catacaggag attgtgccaa ctgtgactct caccagcagt
2641 gcctggttcc tccccttcc ctcagggta gacaaggac ctttgattat tttagctttt
2701 gtttttttat aagcctttt gggtttaaa atagagtttc ttacatttt gggactttt
2761 taataggcat ttcctctttt atatgaagaa ttcccatcca ttgggcccct tctaaccca
2821 gaatgtgacc tcctcctcca gttaccaca gccctgccct ttgcagggtt ggggtggtc
2881 agcggtaccc cggggttagg catcctagac agcagcctga ggaagctggg agatttgggc
2941 catgtagctg cctttgttac tctatttatt ttagtcactt gtataaaaca ccaaataaag
3001 caatagaggc aaactcaaaa aaaaaaaaa aaaaaaaaaa aaaaaa
```

Figure 30

SEQ ID NO:14 - 3' UTR of ATDC (TRIM29) gene, exemplary target region for miRNAs of ATDC:

```
          gctcctggc ggaaggaacg aggcgccaca
1921 ccctgctct tcctcctgac cctgctgctc ttgccttcta agctactgtg cttgtctggg
1981 tggagggag cctgtcctg cacctgccct ctgcagccct ctgccagcct cttggggca
2041 gttccggcct ctccgacttc cccactggcc acactccatt cagactcctt tcctgccttg
2101 tgacctcaga tggtcaccat cattcctgtg ctcagaggcc aacccatcac aggggtgaga
2161 taggttgggg cctgcccta cccgccagcc tcctcctctc gggctggatc tgggggctag
2221 cagtgagtac ccgcatggta ctcagcctgcc tctcccgccc acgccctgct gtctccaggc
2281 ctatagacgt ttctctccaa ggccctatcc cccaatgttg tcagcagatg cctggacagc
2341 acagccaccc atctcccatt cacatggccc acctcctgct tcccagagga ctggccctac
2401 gtgctctctc tcgtcctacc tatcaatgcc cagcatggca gaacctgcag ccctggcca
2461 ctgcagatgg aaacctctca gtgtcttgac atcaccctac ccaggcggtg ggtcttccacc
2521 acagccactt tgagtctgtg gtccctggag ggtggcttct cctgactggc aggatgacct
2581 tagccaagat attcctctgt tccctctgct gagataaaga attcccttaa catgatataa
2641 tccaccatg caaatagcta ctgacccagc taccatttac catttgccta cagaaatttca
2701 ttcagtctac actttggcat tctctctggc gatggagtgt ggctgggctg accgcaaaag
2761 gtgccttaca cactgcccc acccttcagcc gttgccccat cagaggctgc ctcctccttc
2821 tgattaccc ccatgttgca tatcaggggtg ctcaaggatt ggagaggaga caaaaccagg
2881 agcagcacag tgggacatc tccgtctca acagcccag gcctatgggg gctctggaag
2941 gatgggccag cttgcagggg ttggggaggg agacatccag cttgggcttt ccccttttgga
3001 ataaaccatt ggtctgtgtcaa aaaaaaaaaa aaaaaaa
```

Silencing of ATDC Impacts Cancer Stem Cell Numbers

P7 Gate: CD44+CD24+ESA+ cells

COMPOSITIONS AND METHODS FOR TREATING CANCER

The present application claims priority to U.S. Provisional Application Ser. No. 61/013,109, filed Dec. 12, 2007, which is herein incorporated by reference in its entirety.

STATEMENT REGARDING FEDERALLY SPONSORED RESEARCH OR DEVELOPMENT

This invention was made with government support under R01 CA121830-01 awarded by the National Institutes of Health. The government has certain rights in the invention.

FIELD OF THE INVENTION

The present invention relates to therapeutic targets for cancer. In particular, the present invention relates to small molecules and nucleic acids that target ATDC (Ataxia-Telangiectasia Group D Complementing Gene, also known as TRIM29) expression in cancer, such as pancreatic cancer.

BACKGROUND OF THE INVENTION

Pancreatic cancer is the most frequent adenocarcinoma and has the worst prognosis of all cancers, with a five-year survival rate of <3 percent, accounting for the $4^{th}$ largest number of cancer deaths in the USA (Jemal et al., CA Cancer J Clin., 53: 5-26, 2003). Pancreatic cancer occurs with a frequency of around 9 patients per 100,000 individuals making it the $11^{th}$ most common cancer in the USA. Currently the only curative treatment for pancreatic cancer is surgery, but only ~10-20% of patients are candidates for surgery at the time of presentation, and of this group, only ~20% of patients who undergo a curative operation are alive after five years (Yeo et al., Ann. Surg., 226: 248-257, 1997; Hawes et al., Am. J. Gastroenterol., 95: 17-31, 2000).

The horrible prognosis and lack of effective treatments for pancreatic cancer arise from several causes. There are currently no effective biomarkers useful for early detection of pancreatic cancer or even to differentiate between pancreatic adenocarcinoma and another major pancreatic disease, chronic pancreatitis. Pancreatic cancer tends to rapidly invade surrounding structures and undergo early metastatic spreading, such that it is the cancer least likely to be confined to its organ of origin at the time of diagnosis (Greenlee et al., 2001. CA Cancer J. Clin., 51: 15-36, 2001). Finally, pancreatic cancer is highly resistant to both chemo- and radiation therapies (Greenlee et al., 2001. CA Cancer J. Clin., 51: 15-36, 2001). Currently the molecular basis for these characteristics of pancreatic cancer is unknown. What are needed are improved methods for the early diagnosis and treatment of pancreatic cancer.

SUMMARY OF THE INVENTION

The present invention relates to therapeutic targets for cancer. In particular, the present invention relates to small molecules and nucleic acids that target ATDC expression in cancer, such as pancreatic cancer or gastric cancer.

Experiments conducted during the course of development of embodiments for the present invention identified ATDC as a novel DNA damage response gene that confers a survival advantage to pancreatic cancer cells when exposed to chemotherapy. It was shown that following DNA damage, ATDC traffics to the nucleus, is phosphorylated in response to gemcitabine and localizes to DNA repair foci. It was also found that high levels of ATDC confer a growth advantage to pancreatic cancer cells both in vitro and in vivo. In addition, it was shown that inhibition of expression of ATDC in an in vivo animal model of pancreatic cancer was highly effective in reducing tumor burden.

Accordingly, in certain embodiments, the present invention provides methods of altering ATDC gene expression in a subject (e.g., a subject exposed to chemotherapy) comprising: introduction of an agent (e.g., an oligonucleotide molecule) into the subject to treat and/or prevent cancer. The methods are not limited to a particular type of cancer. In some embodiments, the cancer is pancreatic cancer or gastic cancer. In particular embodiments, the subject has a cancer overexpressing ATDC, such as pancreatic cancer or gastric cancer. In some embodiments, the cancer is breast cancer. In some embodiments, the cancer is lung cancer. In some embodiments, the cancer is any kind of cancer having altered ATDC expression. In certain embodiments, the subject comprises non-tumorigenic cancer cells and tumorigenic cancer stem cells, and wherein administering the agent kills the non-tumorigenic cancer cells, the tumorigenic cancer stem cells, or both the non-tumorigenic cancer cells and the tumorigenic cancer stem cells.

The present invention is not limited to a particular agent. In some embodiments, the agent comprises an oligonucleotide that functions via RNA interference. In some embodiments, the oligonucleotide is an antisense oligonucleotide, an siRNA, an shRNA, miRNA or a related molecules, or combinations thereof. In some embodiments, the oligonucleotide has a region of identity or of substantial identity of at least 15 nucleotides with the ATDC gene. In some embodiments the oligonucleotide molecule comprises a region of at least 13 (e.g., 13, 14, 15, 16, 17, 18, 19, 20, 21, 22, 23, 24, 25, etc.) contiguous nucleotides of SEQ ID NO:1 or its complement. In some embodiments, the oligonucleotide is SEQ ID NO: 3, SEQ ID NO: 4, SEQ ID NO: 5, and/or SEQ ID NO: 6. In particular embodiments, the oligonucleotide is an miRNA sequence, such as, for example: miR-34a, miR-34c, miR-296, miR-650, miR-299-5p, miR-185, miR-765, miR-522, and miR-362.

The methods are not limited to a particular type or kind of oligonucleotide molecule. In some embodiments, the oligonucleotide molecule comprises shRNA. In some embodiments, the oligonucleotide molecule comprises siRNA. In some embodiments, the oligonucletide molecule comprises DNA molecules encoding siRNA or shRNA molecules. In some embodiments, the oligonucleotide molecule is operably linked with a promoter (e.g., a human U6 promoter). The methods are not limited to a particular type of subject. In some embodiment, the subject is a human being. In some embodiments, the subject has pancreatic cancer or gastic cancer. In some embodiments, the composition comprises a targeting ligand specific for pancreatic cancer tumors (e.g., transferrin).

In some embodiments, the present invention provides compositions, systems, and kits comprising: a) an agent that alters ATDC expression or activity in a subject that has cancer; and b) a chemotherapeutic agent. In certain embodiments, the agent comprises an anti-ATDC siRNA sequence and the chemotherapeutic agent comprises gemcitabine.

In certain embodiments, the present invention provides methods for inhibiting the growth of cancer cells (e.g., non-tumorigenic cancer cells or tumorigenic cancer stem cells), comprising, for example, contacting a cancer cell expressing ATDC (e.g., over-expressing ATDC compared to normal basal levels) with a composition comprising an agent that alters ATDC gene expression under conditions such that the expression of ATDC in the cell is inhibited. The methods are not limited to treatment of a certain type of cancer. In some embodiments, the type of cancer being treated is pancreatic cancer or gastic cancer. The methods are not limited to a particular type of subject. In some embodiments, the subject is a human while in other embodiments, the subject is a non-human (e.g., rodent).

In some embodiments, the present invention provides methods of inhibiting the growth of cancer cells (e.g., non-tumorigenic cancer cells or tumorigenic cancer stem cells), comprising: contacting a cancer cell expressing Dvl-2 and/or Hint-1 with an agent under conditions such that the expression of Dvl-2 and/or Hint-1 in the cancer cell is inhibited. In certain embodiments, the agent comprises an oligonucleotide that functions via RNA interference. In particular embodiments, the oligonucleotide is selected from the group consisting of an antisense oligonucleotide, an siRNA, an shRNA, and a miRNA (e.g., for Dvl-1, SEQ ID NOs: 7, 8, 9, 10 or the complement thereof). In other embodiments, for targeting Dvl-1, the oligonucleotide molecule comprises a region of at least 13 (e.g., 13, 14, 15, 16, 17, 18, 19, 20, 21, 22, 23, 24, 25, etc.) contiguous nucleotides of SEQ ID NO:13 or its complement. In particular embodiments, the cancer cell is a pancreatic cancer cell, pancreatic cancer stem cell, or a gastric cancer cell, or a gastic cancer stem cell. In other embodiments, the cancer cell or cancer stem cell is in an organism (e.g., human, dog, cat, cow, pig or other livestock).

In some embodiments, the present invention provides methods for treating a subject with cancer comprising: administering an agent that alters (e.g., inhibits) ATDC, Dvl-2, or Hint-1 expression or activity to a subject that has cancer. In certain embodiments, the agent comprises an oligonucleotide that functions via RNA interference. In further embodiments, the oligonucleotide is selected from the group consisting of an antisense oligonucleotide, an siRNA, an shRNA, and a miRNA. In particular embodiments, the methods further comprise administering a chemotherapeutic agent to the subject (e.g., gemcitabine or similar agent). In further embodiments, the methods further comprise: exposing the subject to ionizing-radiation and/or UV light. In other embodiments, the subject is a human being that has been previously treated with chemotherapy (e.g, gemcitabine or other chemotherapeutic). In particular embodiments, the subject has, or is suspected to have, pancreatic cancer or gastic cancer. In further embodiments, the agent comprises a targeting ligand specific for pancreatic cancer tumors. In some embodiments, the targeting ligand is transferrin or an antibody or its fragments against the transferrin receptor.

In certain embodiments, the present invention provides methods for treating pancreatic or gastric cancer in a subject (e.g., human subject, non-human subject) comprising inhibiting phosphorylation of ATDC polypeptides within pancreatic cancer cells, and/or inhibiting binding between ATDC polypeptide and HINT1 polypeptide within pancreatic cancer cells. In some embodiments, the methods further involve co-administration of an anti-cancer agent. Examples of anti-cancer agents include, but are not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino) ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserel in Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl- N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis(platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); 2-chlorodeoxyadenosine (2-Cda), Antiproliferative agents, Piritrexim Isothionate, Antiprostatic hypertrophy agents, Sitogluside, Benign prostatic hyperplasia therapy agents, Tamsulosin Hydrochloride, Prostate growth inhibitor agents, Pentomone, and Radioactive agents, Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; and Triolein I 131.

BRIEF DESCRIPTION OF THE DRAWINGS

FIG. 8 also shows ATDC translocates into nuclear foci after gemcitabine (10 mM) and co-localizes with phosphorylated H2AX (C) and ATR (D). ATDC is not required for the formation of either gH2AX or ATR nuclear foci (C, D) suggesting that ATDC functions parallel to or downstream of ATR and gH2AX. Results representative of 3 separate experiments.

FIG. 16: In mice injected with control-shRNA-GFP-nanovector, qRT-PCR showed significantly increased expression of GFP mRNA, 40-250-fold more than ATDC-shRNA-nanovector which lacks GFP gene in the construct, indicating nanovector can efficiently deliver plasmid DNA to BxPC3 orthotopic tumors in vivo (FIG. 16A), and in a PANC-1 orthotopic model (FIG. 16B).

FIG. 19 shows SEQ ID NO:01, which is a nucleic acid sequence of a human ATDC (TRIM 29) gene sequence.

FIG. 20 shows SEQ ID NO:02, which is an amino acid sequence of a human ATDC (TRIM29) protein sequence.

FIG. 21 shows SEQ ID NO:03, SEQ ID NO:04, SEQ ID NO:05, and SEQ ID NO:06.

FIG. 28 shows the sense and anti-sense shRNA sequences to Dvl-2 shRNA1 (SEQ ID NOs: 7 and 8 respectively), the sense and anti-sense shRNA sequences to Dvl-2 shRNA2 (SEQ ID NOs:9 and 10 respectively) and sense and anti-sense missense shRNA target sequences (control shRNA, SEQ ID NOs: 11 and 12).

FIG. 29 shows the nucleic acid sequence of human disheveled 2 (Dvl-2), which is SEQ ID NO:13.

FIG. 30 shows SEQ ID NO:14, which is the 3' of ATDC (TRIM29) gene, which is an exemplary target region for miRNAs of ATDC. In certain embodiments, therapeutic RNA sequences composed of about 18-24 consecutive nucleotides from this sequence are constructed and used to silence ATDC expression.

FIGS. 31A and B are L3.6PL cells, and FIGS. 31 C and D are BXPC3 cells. The lanes in these figures is as follows: 1(a). Lipofectamine2000 only; 2(b). Control miRNA; 3. miR-299-5p; 4. miR-185; 5. miR-522; 6. miR-506; 7. miR-765; 8. miR-362; 9. miR-515-5p; 10. miR-661; 11. miR-525; c. miR-34a; d. miR-34b; e. miR-34c; f. miR-150; g. miR-296; h. miR-500; and i. miR-650.

DEFINITIONS

Figure 1:
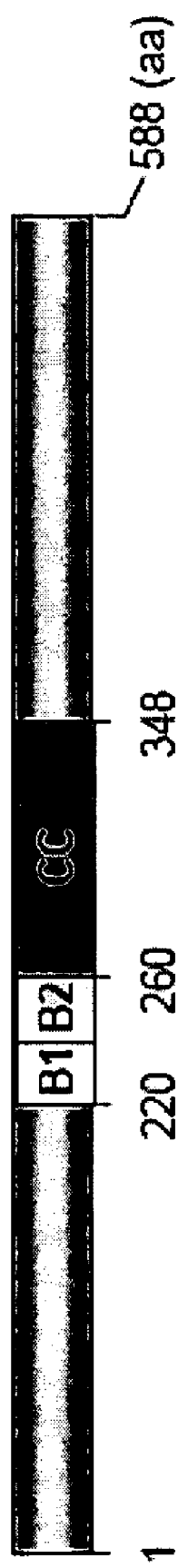
FIG. 1 shows the ATDC protein structure.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject diagnosed with a cancer" refers to a subject who has been tested and found to have cancerous cells. The cancer may be diagnosed using any suitable method, including but not limited to, biopsy, x-ray, CT imaging, blood test, and the diagnostic methods of the present invention.

As used herein, the term "non-human animals" refers to all non-human animals including, but are not limited to, vertebrates such as rodents, non-human primates, ovines, bovines, ruminants, lagomorphs, porcines, caprines, equines, canines, felines, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

The term "RNA interference" or "RNAi" refers to the silencing or decreasing of gene expression by siNAs (e.g., "short interfering RNA", "siRNA", "short interfering nucleic acid molecule", "short interfering oligonucleotide molecule", or "chemically-modified short interfering nucleic acid molecule"). It is the process of sequence-specific, post-transcriptional gene silencing in animals and plants, initiated by siNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner (see, e.g., Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). In some embodiments, the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see, e.g., Martinez et al., 2002, Cell., 110, 563-574 and Schwarz et al., 2002, Molecular Cell, 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. In some embodiments, siNA molecules do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, e.g., Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin siNA molecule of the invention can comprise an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex siNA molecule of the invention can comprise an antisense region having length sufficient to mediate RNAi in a cell or in vitro system (e.g. about 19 to about 22 nucleotides) and a sense region having about 3 to about 18 nucleotides that are complementary to the antisense region.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siNA) of the invention. In one embodiment, inhibition, down-regulation or reduction with an siNA molecule is below that level observed in the presence of an inactive or attenuated molecule. In another embodiment, inhibition, down-regulation, or reduction with siNA molecules is below that level observed in the presence of, for example, an siNA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "target gene" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule.

By "target nucleic acid" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

DETAILED DESCRIPTION OF THE INVENTION

Pancreatic cancer is a highly lethal disease which is often diagnosed in an advanced state, for which there are little/no effective therapies. It has the worst prognosis of any major malignancy (<5% 5 year survival) and is the fourth most common cause of cancer death per year in the United States, with an annual incidence rate of 31,000 people (see, e.g., Jemal A, et al., 2005. CA Cancer J Clin 55: 10-30). Recent advances in surgical and medical therapy have had little impact on the mortality rate of this disease. One of the major hallmarks of pancreatic cancer is extensive local tumor invasion and early systemic dissemination. Pancreatic cancer is also notoriously resistant to chemotherapy and ionizing radiation.

One approach that has been undertaken to further understand the molecular pathogenesis of pancreatic cancer has been to perform genomic and proteomic profiling to identify differentially expressed genes that might represent novel therapeutic targets (see, e.g., Crnogorac-Jurcevic T, et al., J. Pathol. 2003; 201: 63-74; Logsdon C D, et al., Cancer Res. 2003; 63: 2649-2657; Iacobuzio-Donahue C A, et al., Cancer Res. 2003; 63: 8614-8622; Cao D, et al., Cancer Biol Ther. 2004; 3:1081-1089; Chen R, et al., Gastroenterol. 2005; 129: 1344-1347). Using Affymetrix gene profiling, it was recently determined that pancreatic cancer cells overexpress the Ataxia-Telangiectasia Group D Associated gene (ATDC) at a level at least 20-fold higher than normal pancreas and chronic pancreatitis (see, e.g., Logsdon C D, et al., Cancer Res. 2003; 63: 2649-2657). ATDC was initially described in the hunt for the gene responsible for the genetic disorder ataxia telangiectasia (APT), which is characterized by genomic instability, cerebellar degeneration, radiation sensitivity, and predisposition to cancer. Cell lines from AT patients exhibit hypersensitivity to ionizing radiation (IR), and ATDC was isolated based on its ability to suppress the radiation sensitivity of AT complementation group D fibroblasts (see, e.g., Kapp L N, et al., Int. J. Radiat. Biol. 1989; 56; 667-675; Kapp L N, et al., Am. J. Human Genet. 1992; 51, 45-54). No mutations were found in ATDC, and subsequently the gene responsible for ataxia telangiectasia was identified as ATM (ataxia telangiectasia mutated) (see, e.g., Savitsky K, et al., Science 1995; 268, 1749-1753).

The ATDC gene (also known as TRIM29), located on chromosome 11q23, possesses multiple zinc finger motifs and an adjacent leucine zipper motif and has been proposed to form homo- or hetero-dimers. RNA blot analysis shows that there are multiple ATDC transcripts, but only the 3.0 kB transcript has been determined to express a functional protein (see, e.g., Tauchi H, et al., Mutagenesis 2000; 15: 105-108). The 3.0 kB long ATDC transcript corresponds to an open reading frame of 1764 nucleotides, coding for a 588 amino acid protein (see, e.g., Leonhardt E A, et al., Genomics 1994; 19, 130-136). A consensus nucleic acid sequence is provided at accession number NM_012101.3 and a consensus amino acid sequence is provided at accession number NP_036233.2. These sequences are herein incorporated by reference as if fully set forth herein. It is noted that the consensus nucleic acid sequence can be used, for example, to design siRNA sequences in the same manner as SEQ ID NO:1.

Northern blot analysis revealed that ATDC is expressed in placenta, lung, thymus, prostate, testis, and colon, while no expression is observed in heart, brain, skeletal muscle, pancreas, spleen, ovary, or small intestine (see, e.g., Hosoi Y, et al., Int. J. Radiat. Biol. 1994; 66, S71-S76). In addition to an observation of high ATDC levels in primary pancreatic cancers and pancreatic cancer cell lines, a search of the Oncomine database (see, e.g., www, followed by .oncomine.org) revealed that ATDC has been reported to be overexpressed in lung, bladder and ovarian cancers and in endometrial adenocarcinoma and multiple myeloma, while underexpressed in breast and prostate cancer (see, e.g., Mutter G L, et al., Gynecol Oncol. 2004; 83:175-6; Zhan F, et al., Blood 2002; 99:1504; Yu Y P, et al., J Clin Oncol. 2004; 22: 2790-9; LaTulippe E, et al., Cancer Res. 2002; 62:4499-506; Luo J, et al., Cancer Res. 2001; 61:4683-8; Dyrskjot L, et al., Cancer Res. 2004; 64:4040-8; Nacht M, et al. Cancer Res 1999; 59: 5464-5470).

ATDC, also known as TRIM29, is a member of the tripartite motif (TRIM) protein family. TRIM proteins have a series of conserved domains, which include a RING (R), a B-box type 1 (B1) and B-box type 2 (B2), followed by a coiled-coiled (CC) region. While some of the domains may be absent or present in the different TRIM proteins (ATDC contains the B1-B2-CC domains but lacks the R domain) (FIG. 1), their order is always maintained (R-B1-B2-CC) (see, e.g., Reymond A, et al., Embo J 2001; 20, 2140-2151). Genes belonging to the TRIM family have been implicated in a variety of cellular processes, such as development and growth, and in several human diseases, including HIV infection (see, e.g., Stremlau M, et al., Science 2004; 427: 848) and leukemia (see, e.g., Goddard A D, et al., Science 1991; 254: 1371-1374) however, little is known about the biological mechanisms regulated by TRIM proteins. The function of ATDC has not been studied previously in any physiologic or pathologic process.

To understand the functional role of ATDC in pancreatic cancer, experiments conducted during the course of development of embodiments for the present invention explored the effect of ATDC on cellular growth. Using both in vitro and in vivo models, it was shown that ATDC promotes the growth of pancreatic cancer cells. Furthermore, it was shown that the growth-promoting activity of ATDC appears to be linked to the stimulation of the β-catenin pathway via interactions with histidine triad nucleotide-binding protein 1 (HINT1).

Gemcitabine is a nucleoside analogue that is currently considered a gold standard as the chemotherapeutic agent of choice for the treatment of pancreatic cancer. Gemcitabine exerts its anti-tumor effects by becoming incorporated into replicating DNA, which leads to steric hindrance of extending replication forks, leading to fork stalling and S-phase arrest. Previous findings showed that ATDC overexpression rescued the radiosensitivity of AT cells (see, e.g., Kapp L N, et al., Int. J. Radiat. Biol. 1989; 56; 667-675; Kapp L N, et al., Am. J. Human Genet. 1992; 51, 45-54). Experiments conducted during the course of development of embodiments for the present invention showed that ATDC also confers resistance in pancreatic cancer cells to DNA damaging agents and sought to determine the mechanisms involved. Experiments conducted during the course of development of embodiments for the present invention demonstrated that ATDC confers a survival advantage to pancreatic cancer cells in response to DNA damaging agents and ATDC depletion enhances sensitivity to the chemotherapeutic agent gemcitabine. It was also shown that ATDC is a nucleocytoplasmic shuttling protein that following exposure to UV light and gemcitabine becomes phosphorylated and localizes to nuclear foci. Loss of ATDC expression was shown to result in defective DNA double strand break repair, altered cell cycle checkpoint signaling and reduced phosphorylation of p53 and Chk1. These results indicate, for example, ATDC is a highly expressed gene in human pancreatic cancer that promotes tumorigenesis and represents a novel DNA damage response gene.

PKCI, also known as histidine triad nucleotide-binding protein 1 (HINT1), belongs to the histidine triad (HIT) family of proteins. It is a highly conserved protein that shares homology with the tumor suppressor gene fragile histidine triad (FHIT). Although HINT1 was originally thought to inhibit PKC, subsequent studies demonstrated that PKC inhibition might not be the major mechanism by which HINT1 exerted its physiological effects (see, e.g., Su T, et al., Proc. Natl. Acad. Sci. USA 2003; 100, 7824-7829; Choi E K, et al., Int J Radiat Onco Biol Phys 2000; 49; 397-405; Weiske J, et al., J. Cell Science 2005; 118, 3117-3129), and the physiological function of HINT1 remained unclear. However, recent studies have shed some light on the cellular function of HINT1. Cells derived from HINT1 null mice display an increase in growth rate and resistance to DNA damaging agents (see, e.g., Su T, et al., Proc. Natl. Acad. Sci. USA 2003; 100, 7824-7829), similar to observed overexpression of ATDC. Conversely, overexpression of HINT1 was shown to make cells more sensitive to DNA damage (IR) (see, e.g., Choi E K, et al., Int J Radiat Onco Biol Phys 2000; 49; 397-405). HINT1 null mice were more susceptible to carcinogen-induced tumor formation, suggesting that like FHIT, HINT1 might have a tumor suppressor function. HINT1 has also been shown to interact with the proteins pontin and reptin to inhibit TCF-β-catenin-mediated transcription (see, e.g., Weiske J, et al., J. Cell Science 2005; 118, 3117-3129) and to trigger apoptosis by upregulation of p53 expression coinciding with upregulation of the pro-apoptotic factor Bax and downregulation of the apoptosis inhibitor Bcl-2 (see, e.g., Weiske J, et al., J Biol Chem 281:41175-41181.

In experiments conducted during the course of development of embodiments for the present invention, HINT1 and ATDC were shown to be binding partners in pancreatic cancer cells. In addition, experiments conducted during the course of development of embodiments for the present invention indicated that expression targeting of ATDC by nucleic acid interference in an in vivo animal model of pancreatic cancer was highly effective in reducing tumor burden. It was also shown that the nanovector targeting system was highly efficient in targeting human pancreatic cancer cells both in the pancreas and at metastatic sites.

Accordingly, the present invention relates to therapeutic targets for cancer. In particular, the present invention relates to small molecules, nucleic acids, and biomolecules (e.g., peptides, antibodies, etc.) that target ATDC expression in cancer (e.g., pancreatic cancer) or that target ATDC protein or its interaction with other proteins (e.g., antibodies that prevent the association of ATDC with HINT1).

In some embodiments, the present invention provides therapies for cancer (e.g., pancreatic cancer). In some embodiments, therapies target ATDC; Dvl-2, and/or HINT-1.

ATDC was identified as a cancer marker with altered expression in cancer (e.g. pancreatic cancer) in previous studies (see, e.g., U.S. Pat. No. 6,749,863; Tibbetts R S, Genes Dev 2000; 14:2989-3002; Zou L, Science 2003; 300: 1542-1548). The nucleic acid sequence for one exemplary ATDC is provided as SEQ ID NO:01, and the corresponding amino acid sequence as SEQ ID NO:02. A consensus nucleic acid sequence is provided at accession number NM_012101.3 and a consensus amino acid sequence is provided at accession number NP_036233.2.

The present invention is not limited to a particular methods for treating cancer (e.g, pancreatic cancer). In some embodiments, the present invention provides methods for treating cancer wherein ATDC, Dvl-2, or Hint-1 is targeted for purposes of reducing ATDC, Dvl-2, or Hint-1 expression and/or activity within cancer cells (e.g., pancreatic cancer cells; cancer cells known to have elevated ATDC, Dvl-2, or Hint-1 expression). The methods are not limited to a particular method for reducing ATDC, Dvl-2, or Hint-1 expression and/or activity. In some embodiments, reducing ATDC, Dvl-1, or Hint-1 expression and/or activity involves preventing such expression within cancer cells. In some embodiments, reducing ATDC, Dvl-2, or Hint-1 expression and/or activity involves preventing phosphorylation of ATDC within cancer cells. In some embodiments, reducing ATDC expression and/or activity involves preventing an interaction (e.g., a binding interaction) between ATDC and HINT1 within cancer cells. In some embodiments, reducing ATDC expression and/or activity involves prevention of ATDC stimulated beta-catenin-mediated proliferation through sequestration of HINT1 in cancer cells (e.g., pancreatic cancer cells). The present invention is not limited to a particular manner or method for targeting ATDC, Dvl-2, or Hint-1 for purposes of reducing ATDC expression and/or activity within cancer cells (e.g., pancreatic cancer cells; cancer cells known to have elevated ATDC expression).

In certain embodiments, the methods of the present invention involves the administration of antibodies that target ATDC, Dvl-2, and/or Hint-1. Such antibodies are commercially available from Santa Cruz Biotechnology (e.g., sc-33151 for sc-1613 ATDC; sc-30872 and sc-30873 for Dvl-2) and Novus Biologicals (e.g., H00003094-B01 and H00003094-A01 for Hint-1). There are also additional commercial suppliers of such antibodies.

In some embodiments, the methods involve, for example, the delivery nucleic acid molecules targeting ATDC, Dvl-2, or Hint-1 expression and/or activity within cancer cells (e.g., pancreatic cancer cells). For example, in some embodiments, the present invention employs compositions comprising oligomeric antisense compounds, particularly oligonucleotides, for use in modulating the function of nucleic acid molecules encoding ATDC, Dvl-2, or Hint-1, ultimately modulating the amount of ATDC expressed. This is accomplished by providing antisense compounds that specifically hybridize with one or more nucleic acids encoding ATDC, Dvl-2, or Hint-1. Examples of oligomeric antisense compounds include, but are not limited to, a region of at least 19 contiguous nucleotides of SEQ ID NO:1, or accession number NM_012101.3, or its complement (e.g., SEQ ID NOs: 3, 4, 5 and/or 6) (for targeting ATDC), as well as at least 19 contiguous nucleotides of SEQ ID NO:13 or its complement (e.g, for targeting Dvl-2). Useful siRNA sequences are commercially available from, for example, Santa Cruz Biotechnology (e.g., sc-43625 for ATDC; sc-35230 for Dvl-2; and sc-92005 for Hint-1). Other useful siRNA sequences are commercially available from Origen (e.g., TR317032 for ATDC; TR313337 for Dvl-2; and TR302047). siRNA sequences to ATDC, Dvl-2, and Hint-1 are also commercially available from Sigma Aldrich. All of these commercially available siRNA sequences are herein incorporated by reference into this application.

The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of ATDC, Dvl-1, and/or Hint-1. In the context of the present invention, "modulation" means either an increase (stimulation) or a decrease (inhibition) in the expression of a gene. For example, expression may be inhibited to potentially prevent tumor growth, inhibition of complement mediated lysis, angiogenesis and proliferation associated with ATDC (e.g., in pancreatic cancer).

Introduction of molecules carrying genetic information into cells is achieved by any of various methods including, but not limited to, directed injection of naked DNA constructs, bombardment with gold particles loaded with the constructs, macromolecule mediated gene transfer using, for example, liposomes, biopolymers, and the like, and ex vivo transfection and/or gene therapy followed by transplantation. The present invention is not limited to a particular approach for introducing molecules carrying genetic information to a subject (e.g., a human subject, a non-human subject). In some embodiments, the methods employ a nanovector delivery system (e.g., a cationic liposome-mediated gene transfer system; a lipoplex) for delivering gene therapeutics to a subject. Current approaches to deliver gene therapeutics to cancer patients often employ either viral or non-viral vector systems. Viral vector-directed methods show high gene transfer efficiency but are deficient in several areas. The limitations of a viral approach are related to their lack of tumor targeting and to residual viral elements that can be immunogenic, cytopathic, or recombinogenic. To circumvent these problems, progress has been made toward developing non-viral, pharmaceutical formulations of gene therapeutics for in vivo human therapy, particularly nanovector delivery systems (e.g., cationic liposome-mediated gene transfer systems). Indeed, there are multiple clinical trials underway using nanovector delivery systems for gene delivery, and liposomes for delivery of chemotherapeutics such as doxorubicin are already on the market for breast cancer chemotherapy. Features of nanovector delivery systems (e.g., cationic liposomes) that make them versatile and attractive include: ease of preparation, ability to complex large pieces of DNA/RNA, the ability to transfect many different types of cells, including non-dividing cells, and the lack of immunogenicity or biohazard activity.

In some embodiments, the nanovector delivery systems (e.g., cationic liposomes) are configured to bear a ligand recognized by a cell surface receptor (e.g., to increase desired targeting to, for example, a tumor). The nanovector delivery systems are not limited to a particular ligand recognized by a cell surface receptor. In some embodiments, the ligand is recognized by a cell surface receptor specific to a tumor. In some embodiments, the ligand is transferrin (Tf). In some embodiments, the ligand is a single chain antibody fragment (scFv) (e.g., specific to Tf). Receptor-mediated endocytosis represents a highly efficient internalization pathway in eukaryotic cells. The presence of a ligand on a nanovector delivery systems (e.g., cationic liposome; lipoplex) facilitates the entry of DNA into cells. Recently, a tumor specific, ligand-targeting, self-assembled nanoparticle-DNA lipoplex system designed for systemic gene therapy of cancer was developed (see, e.g., U.S. Pat. No. 6,749,863; Tibbetts R S, Genes Dev 2000; 14:2989-3002; Zou L, Science 2003; 300: 1542-1548). These nanovector systems employ transferrin (Tf) or a single chain antibody fragment (scFv) against the transferrin receptor which is overexpressed in the majority of human cancers, including pancreatic cancer (see, e.g., Busino L, et al., Nature 2003; 426: 87-91). TfR-scFv-targeted nanovectors were recently approved by the FDA for clinical testing and the first Phase I clinical trial for non-viral systemic p53 gene therapy is ongoing. This nanovector delivery system for systemic siRNA/shRNA therapy provides a tumor-targeted delivery system for the effective treatment of human pancreatic cancer. Indeed, experiments conducted during the course of development of embodiments for the present invention indicated that shRNA targeting of ATDC in an in vivo orthotopic mouse model of pancreatic cancer was highly effective in reducing tumor burden. It was also shown that the nanovector targeting system was highly efficient in targeting human pancreatic cancer cells both in the pancreas and at metastatic sites.

Some methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is incorporated herein by reference in their entireties.

In some embodiments, the present invention provides shRNAs that inhibit the expression of ATDC (e.g., in pancreatic cancer cells). A short hairpin RNA (shRNA) is a sequence of RNA that makes a tight hairpin turn that can be used to silence gene expression via RNA interference (e.g., silence ATDC gene expression). shRNA typically uses a vector introduced into cells and utilizes a promoter (e.g., the U6 promoter) to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. Examples of shRNAs for ATDC include, but are not limited to, a region of at least 19 contiguous nucleotides of SEQ ID NO:1 (or accession number NM_012101.3) or its complement (e.g., SEQ ID NOs: 3, 4, 5 and/or 6). Other examples include, for Dvl-2, SEQ ID NOs:7-10.

In some embodiments, the present invention provides siRNAs that inhibit the expression of ATDC (e.g., in pancreatic cancer cells). siRNAs are extraordinarily effective at lowering the amounts of targeted RNA (e.g., ATDC RNA), and by extension proteins, frequently to undetectable levels. The silencing effect can last several months, and is extraordinarily specific, because one nucleotide mismatch between the target RNA and the central region of the siRNA is frequently sufficient to prevent silencing (see, e.g., Brummelkamp et al, Science 2002; 296:550-3; and Holen et al, Nucleic Acids Res. 2002; 30:1757-66). An important factor in the design of siRNAs is the presence of accessible sites for siRNA binding. Bahoia et al., (J. Biol. Chem., 2003; 278: 15991-15997) describe the use of a type of DNA array called a scanning array to find accessible sites in mRNAs for designing effective siRNAs. These arrays comprise oligonucleotides ranging in size from monomers to a certain maximum, usually Corners, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29 (10): 2041-2045). Additional methods and concerns for selecting siRNAs are described for example, in WO 05054270, WO05038054A1, WO03070966A2, J Mol. Biol. 2005 May 13; 348 (4):883-93, J Mol. Biol. 2005 May 13; 348 (4):871-81, and Nucleic Acids Res. 2003 Aug. 1; 31 (15): 4417-24, each of which is herein incorporated by reference in its entirety. In addition, software (e.g., the MWG online siMAX siRNA design tool) is commercially or publicly available for use in the selection of siRNAs.

In some embodiments, the present invention provides MicroRNAs that inhibit the expression of ATDC, Dvl-2, or Hint-1 (e.g., in pancreatic cancer cells). MicroRNAs are regulatory, non-protein-coding, endogenous RNAs that have recently gained considerable attention in the scientific community. They are 18-24 nucleotides in length and are thought to regulate gene expression through translational repression by binding to a target mRNA (see, e.g., Lim et al., Science 2003; 299 (5612):1540; Chen et al., Semin Immunol 2005; 17 (2):155-65; Sevignani et al., Mamm Genome 2006; 17 (3): 189-202). They are also proposed to regulate gene expression by mRNA cleavage, and mRNA decay initiated by miRNA-guided rapid deadenylation (Wu et al., Proc Natl Acad Sci USA 2006; 103 (11):4034-9). miRNAs are abundant, highly conserved molecules and predicted to regulate a large number of transcripts. To date the international miRNA Registry database has more than 600 human identified microRNAs (Griffiths-Jones et al., Nucleic Acids Res 2006; 34 (Database issue):D140-4) and their total number in humans has been predicted to be as high as 1,000 (Berezikov et al., Cell 2005; 120 (1):21-4). Many of these microRNAs exhibit tissue-specific expression (Sood et al., Proc Natl Acad Sci USA 2006; 103 (8):2746-51) and many are defined to be either tumor suppressors or oncogenes (Lee et al., Curr Opin Investig Drugs 2006; 7 (6):560-4; Zhang et al., Dev Biol 2006; Calin et al., Nat Rev Cancer 2006; 6 (11):857-66) and play a crucial role in variety of cellular processes such as cell cycle control, apoptosis, and haematopoiesis. Dysregulation of several miRNAs are thought to play a significant role in human disease processes including tumorigenesis (Hwang et al., Br J Cancer 2006; 94 (6):776-80; Thomson et al., Genes Dev 2006; 20 (16):2202-7).

A siNA molecule of the present invention can be adapted for use to treat any disease, infection or condition associated with gene expression, and other indications that can respond to the level of gene product in a cell or tissue, alone or in combination with other therapies. For example, a siNA molecule can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074), poly(lactic-co-glycolic)acid (PLGA) and PLCA microspheres (see for example U.S. Pat. No. 6,447,796 and U.S. Patent Application Publication No. US 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262. Many examples in the art describe CNS delivery methods of oligonucleotides by osmotic pump, (see Chun et al., 1998, Neuroscience Letters, 257, 135-138, D'Aldin et al., 1998, Mol. Brain Research, 55, 151-164, Dryden et al., 1998, J. Endocrinol., 157, 169-175, Ghimikar et al., 1998, Neuroscience Letters, 247, 21-24) or direct infusion (Broaddus et al., 1997, Neurosurg. Focus, 3, article 4). Other routes of delivery include, but are not limited to oral (tablet or pill form) and/or intrathecal delivery (Gold, 1997, Neuroscience, 76, 1153-1158). More detailed descriptions of nucleic acid delivery and administration are provided in Sullivan et al., supra, Draper et al., PCT WO93/23569, Beigelman et al., PCT WO99/05094, and Klimuk et al., PCT WO99/04819 all of which have been incorporated by reference herein. The siNAs of the instant invention can be used as pharmaceutical agents. Pharmaceutical agents prevent, modulate the occurrence, or treat (alleviate a symptom to some extent, preferably all of the symptoms) of a disease state in a subject.

Thus, the invention features a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siNA molecules of the invention to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, Fundam. Clin. Pharmacol., 13, 16-26); biodegradable polymers, such as poly(DL-lactide-coglycolide) microspheres for sustained release delivery after intracerebral implantation (Emerich, D F et al, 1999, Cell Transplant, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies for the nucleic acid molecules of the instant invention include material described in Boado et al., 1998, J. Pharm. Sci., 87, 1308-1315; Tyler et al., 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058.

The invention also features the use of the composition comprising surface-modified liposomes containing poly(ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation based on their ability to avoid accumulation in metabolically aggressive MPS tissues such as the liver and spleen.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In some embodiments, the present invention provides antibodies (e.g., full length or portions thereof, the generation of which is described herein) that target ATDC in pancreatic cancer cells (e.g., tumors). In preferred embodiments, the antibodies used for treating pancreatic cancer are humanized monoclonal antibodies. In preferred embodiments, the antibody alters (e.g., inhibits) ATDC activity or function.

In some embodiments, the methods of the present invention directed toward reducing ATDC expression and/or activity, further involve co-administration with an anti-cancer agent (e.g., chemotherapeutic). The present invention is not limited by type of anti-cancer agent co-administered. Indeed, a variety of anti-cancer agents are contemplated to be useful in the present invention including, but not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

Other anti-cancer agents include: Antiproliferative agents (e.g., Piritrexim Isothionate), Antiprostatic hypertrophy agent (e.g., Sitogluside), Benign prostatic hypertrophy therapy agents (e.g., Tamsulosin Hydrochloride), Prostate growth inhibitor agents (e.g., Pentomone), and Radioactive agents: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony. Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Another category of anti-cancer agents is anti-cancer Supplementary Potentiating Agents, including: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

Still other anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-Cl-2'deoxyadenosine; Fludarabine-$PO_4$; mitoxantrone; mitozolomide; Pentostatin; and Tomudex.

One particularly preferred class of anticancer agents are taxanes (e.g., paclitaxel and docetaxel). Another important category of anticancer agent is annonaceous acetogenin. Other cancer therapies include hormonal manipulation. In some embodiments, the anti-cancer agent is tamoxifen or the aromatase inhibitor arimidex (i.e., anastrozole).

The present invention is not limited by the type of cancer treated. As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

In certain embodiments, the therapies of the present invention target non-tumorigenic cancer cells. In other embodiments, the therapies of the present invention target tumorigenic cancer stem cells. A description of cancer stem cells, such as pancreatic cancer stem cells, is found in U.S. Pat. No. 6,984,522 and WO08092002, both of which are herein incorporated by reference in their entireties.

EXPERIMENTAL

The following examples are provided in order to demonstrate and further illustrate certain preferred embodiments and aspects of the present invention and are not to be construed as limiting the scope thereof.

Example I

Figure 2:
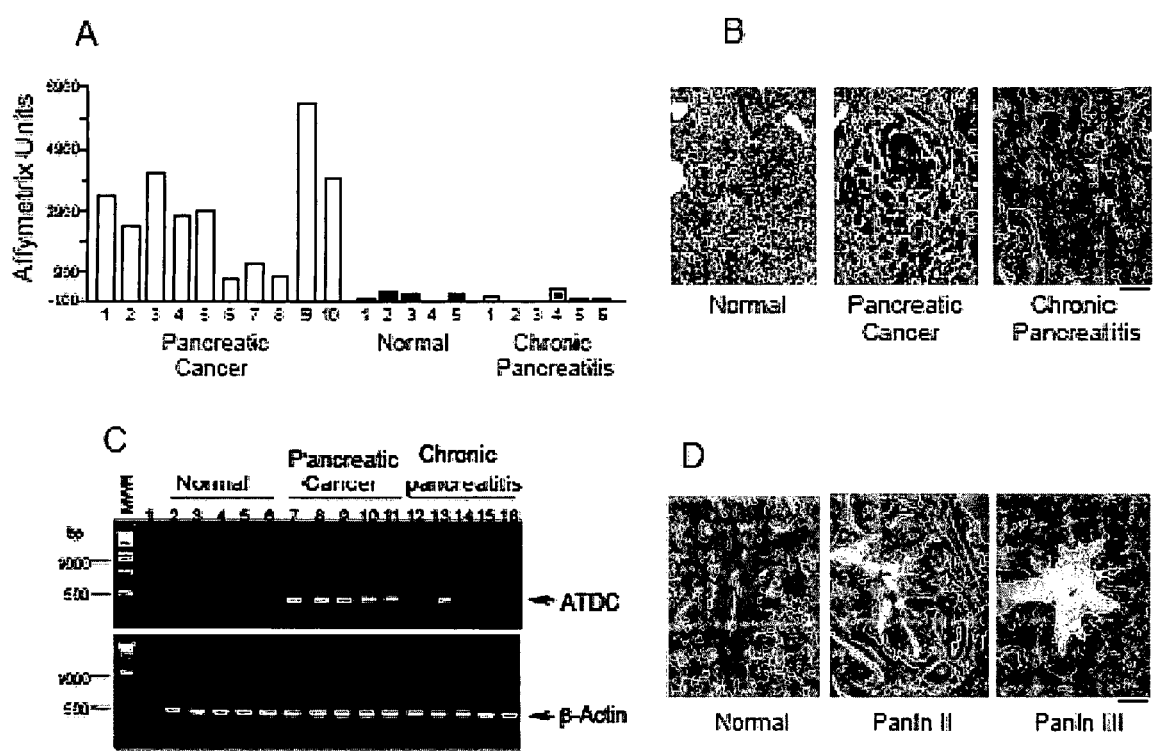
FIG. 2 shows that ATDC is overexpressed in pancreatic cancer. (A) Affymetrix microarray analysis. (B) Immunohistochemistry (IHC) staining using anti-ATDC antibody. (C) Semi-quantitative RT-PCR. (D) IHC staining of ATDC in PanIN lesions.

This example demonstrates that ATDC is overexpressed in the majority of human pancreatic adenocarcinomas. In an attempt to identify novel therapeutic targets for pancreatic cancer, gene expression profiling of microdissected pancreatic adenocarcinomas, and samples of chronic pancreatitis and normal pancreas was performed (see, e.g., Logsdon C D, et al., Cancer Res. 2003; 63: 2649-2657). ATDC (Ataxia-Telangiectasia Group D Complementing Gene) was found to be significantly overexpressed in 10/10 pancreatic adenocarcinomas, with a mean value 20 fold higher than in normal pancreas and chronic pancreatitis (FIG. 2A). ATDC was expressed specifically in the neoplastic epithelium (FIG. 2B). Semi-quantitative RT-PCR (FIG. 2C) was next performed. A progression model of pancreatic cancer is now widely accepted in which normal pancreatic ductal epithelium progresses to infiltrating cancer through a series of morphologically defined pancreatic precursors called PanINs (see, e.g., Hruban R H, et al., Clin. Cancer Res. 2000; 6: 2969-2972). To determine at what stage of the tumorigenic process ATDC is upregulated in pancreatic cancer, the expression of ATDC in PanIN lesions was evaluated. ATDC was not expressed in PanIN 1 (0/4) lesions, occasionally expressed in PanIN 2 (1/7) lesions, and had increased expression in PanIN 3 lesions (3/6) (FIG. 2D), demonstrating, for example, that ATDC is also upregulated in pancreatic cancer precursor lesions.

Example II

Figure 3:
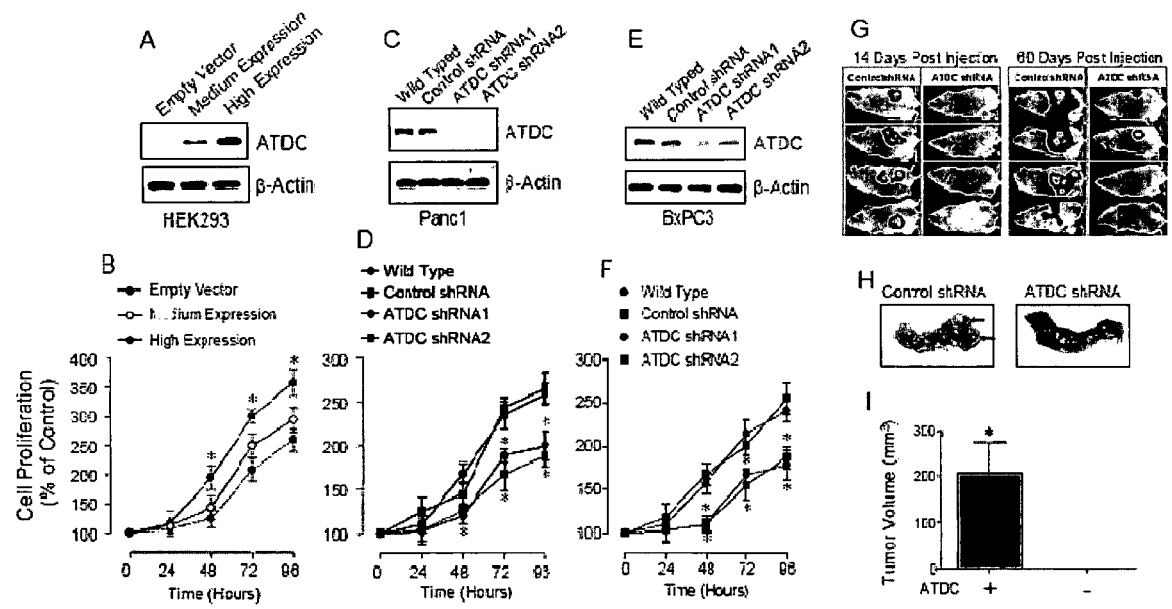
FIG. 3 shows the effect of ATDC on cell proliferation and tumorigenesis. (A) Two HEK cell lines with stable expression (medium or high) of ATDC. (B) Overexpression of ATDC stimulates cell proliferation ($*p<0.05$). (C) Stable knockdown of ATDC with shRNAs in Panc1 cells. (D) Knockdown of ATDC attenuates cell growth of Panc1 cells ($*p<0.05$). (E) Knockdown of ATDC with shRNAs in BxPC3 cells. (F) Knockdown of ATDC inhibits cell growth of BxPC3 cells ($*p<0.05$). (G) Knockdown of ATDC attenuates pancreatic tumor growth in vivo using an othotopic xenograft model. (H) Representative pancreata from NOD-SCID mice 60 days after intrapancreatic injection of tumor cells. (I) Mean tumor volume in control Panc1 cells (ATDC+) and in ATDC knockdown cells (ATDC−) ($*p<0.001$, n=8 per group).

This example demonstrates that overexpression of ATDC confers a growth advantage to pancreatic cancer cells. To understand the functional role of ATDC in pancreatic cancer, the effect of ATDC on cellular growth in vitro was explored by utilizing three cell models with altered levels of ATDC. Following transfection with a construct expressing ATDC ($HEK^{ATDC}$), HEK 293 cells, which normally do not express ATDC, demonstrated a significant increase in cellular proliferation at 72 and 96 hours after plating (FIGS. 3A and B). Conversely, when ATDC was silenced by stable transfection with 2 different shRNAs targeting distinct regions of ATDC in Panc-1 and BxPC-3 pancreatic cancer cells, which have high endogenous levels of ATDC, cellular proliferation was inhibited (FIGS. 3C-F). To examine the effects of ATDC silencing on pancreatic tumor growth and metastasis in vivo, Panc-1 cells expressing control or ATDC shRNA1 were infected with a luciferase-expressing lentivirus. Following injection of $5\times10^5$ cells into the tail of the pancreas, tumor growth was assessed using bioluminescent imaging (n=8 animals per group). All of the animals injected with Panc-1 cells expressing control shRNA demonstrated tumor formation 14 days post-injection while tumors were not detected in the animals injected with Panc-1 ATDC$^{shRNA}$ cells (FIG. 3G). At 60 days post-injection, the control shRNA animals tumors grew significantly larger, with evidence of metastatic spread, while only 25% (2/8) of the ATDC$^{shRNA}$ animals demonstrated evidence of macroscopic tumors (FIGS. 3G and 3H). The mean tumor volume was significantly larger in the tumors grown in mice injected with Panc-1 cells expressing control shRNA compared to mice injected with Panc-1 cells expressing ATDC shRNA (203.2±68.8 vs. 2.01±1.0 mm$^3$, *p<0.001) (FIG. 3I). These data support, for example, the role of ATDC in promoting growth and metastasis of pancreatic cancer cells.

Example III

Figure 4:
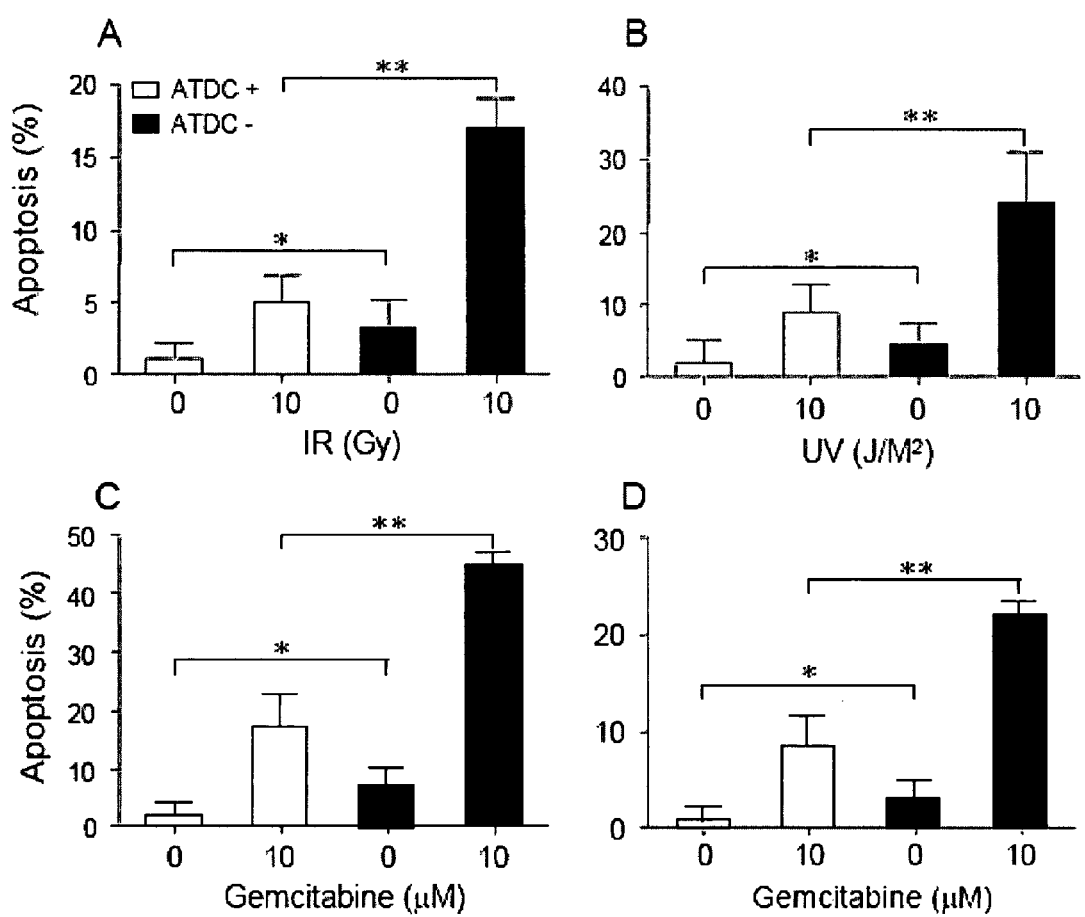
FIG. 4 shows silencing of ATDC renders cells more susceptible to apoptosis induced by IR, UV light, andgemcitabine. Panc1 cells expressing control shRNA (ATDC+) or ATDC-silencing shRNA (ATDC−) were exposed to (A) IR (10 Gy), (B) UV light (10 J/M2) and (C) Gemcitabine (10 µM) and apoptosis was assessed 24 hr later using Annexin V staining. (D) BxPC3 cells with silenced ATDC were also more susceptible to gemcitabine-induced apoptosis ($*p<0.05$, ATDC− vs ATDC+untreated cells; $**p<0.01$, ATDC− vs ATDC+treated cells).
Figure 5:
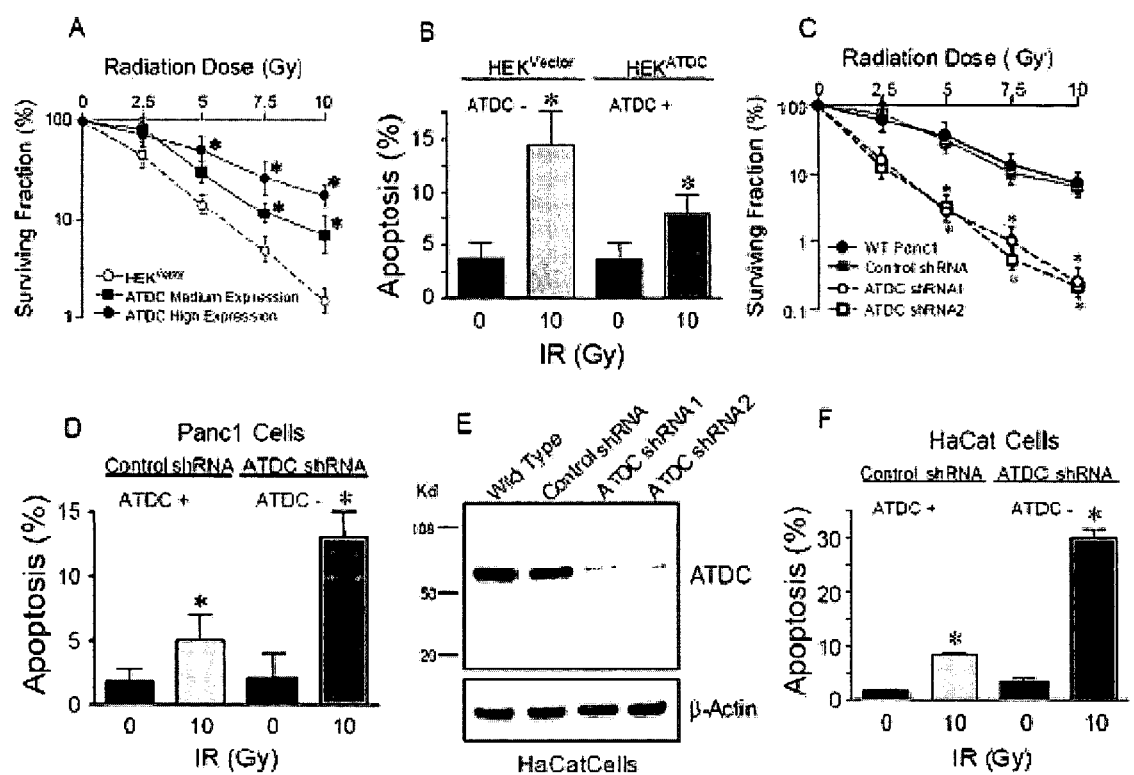
FIG. 5 shows ATDC protects cells against ionizing radiation. (A) Clonagenic cell survival assays in control and ATDC expressing 293 cells following varying doses of IR. (B) HEK-Vector and HEKATDC cells were exposed to IR (10 Gy) for 24 hours. Apoptosis was assessed by annexin staining. (C) Clonagenic cell survival assays following IR in wild type and Panc1 cells stably expressing control shRNA, ATDC shRNA 1, or ATDC shRNA2. (D) Apoptosis in Panc-1 cells expressing control shRNA or ATDC shRNA1 in the absence or presence of 10 Gy IR. (E,F) Similar results are obtained in HaCat cells. ($*p<0.05$ vs IR treated control cells). All experiments were repeated 3 times.

This example demonstrates that ATDC confers a survival advantage in response to DNA damaging agents. Based on previous findings that ATDC overexpression rescued the radiosensitivity of AT cells (see, e.g., Kapp L N, et al., Int. J. Radiat. Biol. 1989; 56; 667-675; Kapp L N, et al., Am. J. Human Genet. 1992; 51, 45-54) it was hypothesized that ATDC also confers radioresistance in HEK 293 cells. It was found that shRNA silencing of ATDC in Panc-1 cells rendered them more susceptible to apoptosis due to IR (FIG. 4A). It is possible that ATDC may also play a role in the DNA damage response elicited by other types of genotoxic insult. A close ally of ATM is ATR, which is primarily responsible for initiating the DNA damage response to genotoxic insult from UV light, chemotherapeutic drugs, and DNA replication-interfering drugs. To explore the possibility that ATDC might participate in ATR-mediated responses, control and ATDC-silenced Panc-1 cells were treated with UV light (10 J/M$^2$, 5 min) and gemcitabine (50 uM/24 hours). Silencing of ATDC in cells made them more susceptible to apoptosis induced by UV light and gemcitabine (FIGS. 4B, 4C), suggesting that, for example, ATDC plays a role in ATR-mediated signaling. Silencing of ATDC in BxPC-3 cells also rendered them more susceptible to apoptosis induced by gemcitabine (FIG. 4D). Expression of ATDC in HEK 293 cells resulted in higher cell survival when exposed to increasing doses of IR compared to wild type HEK 293 cells (FIG. 5A). Similarly, the ability of 10 Gy of IR to induce apoptosis (measured by annexin V expression), was reduced by overexpression of ATDC, confirming that, for example, ATDC confers radiation resistance (FIG. 5B). In contrast, it was found that shRNA silencing of ATDC in Panc-1 cells rendered them more sensitive to IR, with a marked decrease in the surviving fraction following IR (FIG. 5C). It was also found that silencing of ATDC increased susceptibility to apoptosis due to IR (FIG. 5D). To determine if these findings were generalizable to other cell types, the effects of silencing ATDC in HaCAT cells (a cell line derived from immortalized adult skin keratinocytes known to express ATDC) was examined. Annexin V staining in HaCAT cells showed that IR-induced apoptosis was significantly increased when ATDC expression was silenced (FIGS. 5E, 5F).

Example IV

Figure 6:
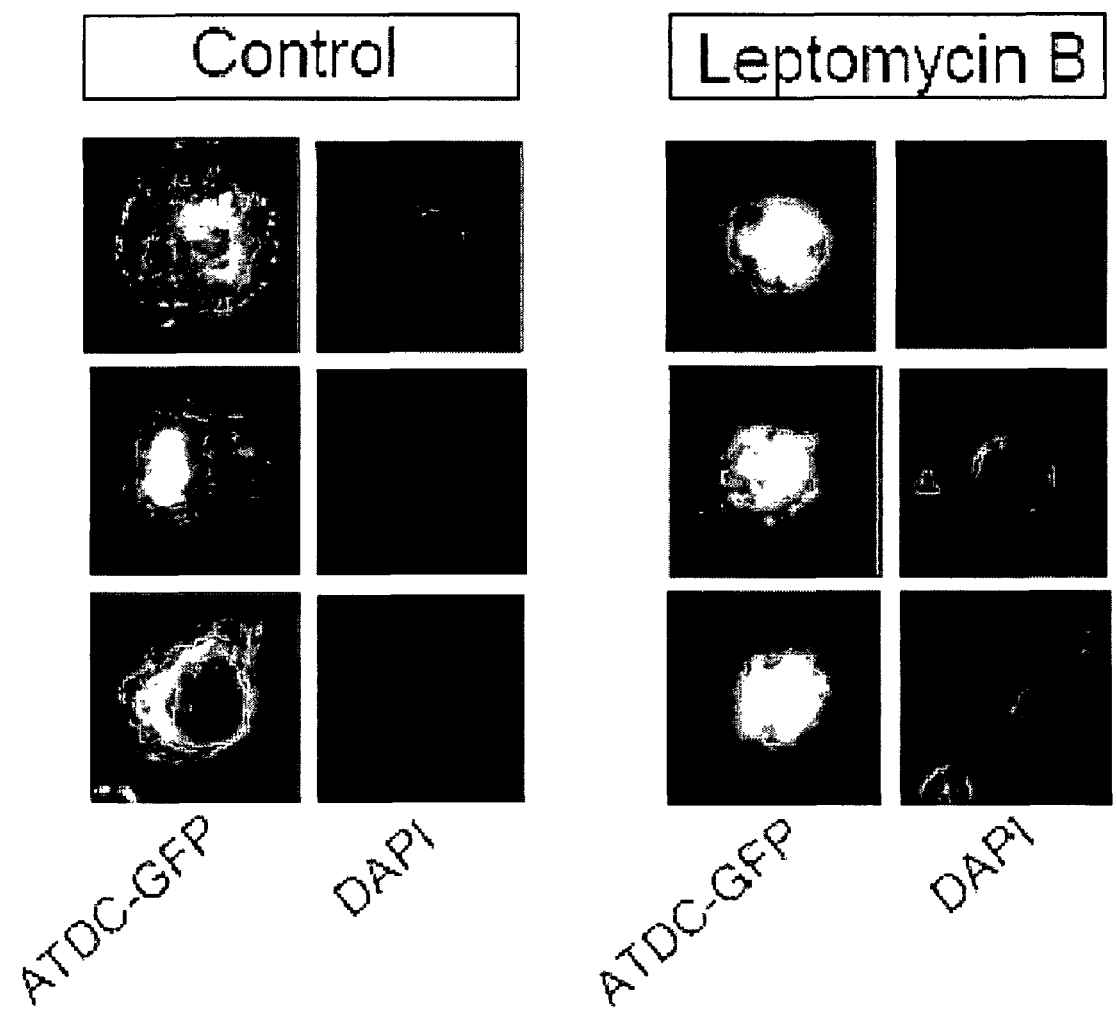
FIG. 6 shows ATDC traffics into the nucleus. Treatment of Panc1 cells expressing an ATDCGFP expression vector with the nuclear export inhibitor leptomycin (1 ng/ml, 6 hr) results in nuclear retention of ATDC.

This example demonstrates that ATDC participates in the DNA damage response. In previous reports, ATDC was described as being predominately cytoplasmic in several cell types (see, e.g., Reymond A, et al., Embo J 2001; 20, 2140-2151; Brzoska P M, et al., Proc. Natl. Acad. Sci. USA 1995; 92, 7824-7828), conflicting with its potential role in the DNA damage response/DNA repair. In localization studies, it was determined that both endogenous ATDC and GFP-tagged ATDC had predominantly cytoplasmic localization, with some staining in the nucleus. To better understand how a protein with predominately cytoplasmic localization might be involved in the DNA response, wild type Panc-1 cells was treated with the nuclear export inhibitor leptomycin B (1 ng/ml) for 6 hours. Treatment with leptomycin B resulted in ATDC accumulation in the nucleus, demonstrating that, for example, ATDC is a nucleocytoplasmic shuttling protein (FIG. 6). Similar results were observed with BxPC-3 cells.

Phosphorylation of the histone variant H2AX (γH2AX) is a well-recognized readout of DNA damage and has been demonstrated at sites of gemcitabine-induced stalled replication forks (see, e.g., Ewald B, et al., Mol Cancer Ther 2007; 6: 1239-1248). γH2AX foci are rapidly formed at DNA damage sites and are thought to play a role in the repair of these alterations. In control Panc-1 cells, gemcitabine treatment (50 uM, x hours) induced a transient H2AX phosphorylation, with induction seen as early as 10 minutes, with return to basal levels after 1 hour (FIG. 6A). In contrast, gemcitabine-treated Panc-1 ATDC$^{shRNA}$ cells showed enhanced phosphorylation of H2AX and a prolonged recovery time, suggesting that, for example, either DNA damage induced by gemcitabine was worsened or DNA double strand break repair was abrogated in these cells (FIG. 6B).

Figure 8:
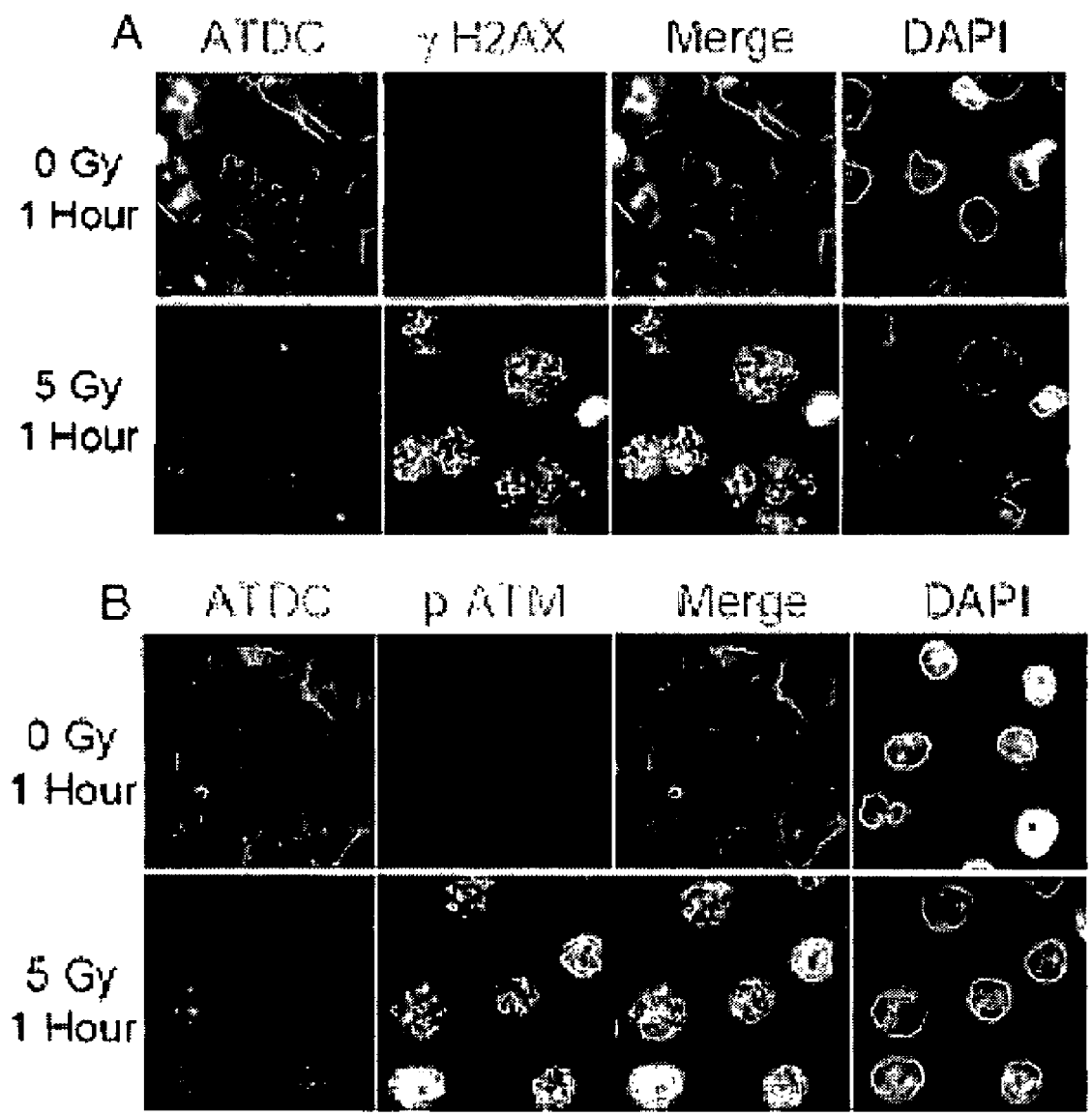
FIG. 8 shows ATDC traffics to DNA repair foci. (A). Panc1 cells exposed to IR (5 Gy, 1 hr) were fixed and costained with anti-ATDC (red) and anti-γH2AX (green) antibodies. Co-localization of ATDC foci (red) with γH2AX foci (green) is demonstrated in the Merge column (yellow). Cell nuclei were counterstained with DAPI (blue). (B) Panc-1 cells exposed to IR (5 Gy, 1 hr) and co-immunostained with anti-ATDC antibody (red) and anti-p-ATM antibody (green). Co-localization of ATDC (red) with p-ATM (green) is observed in yellow in the merged image. Experiments were repeated twice with similar results.
Figure 8:
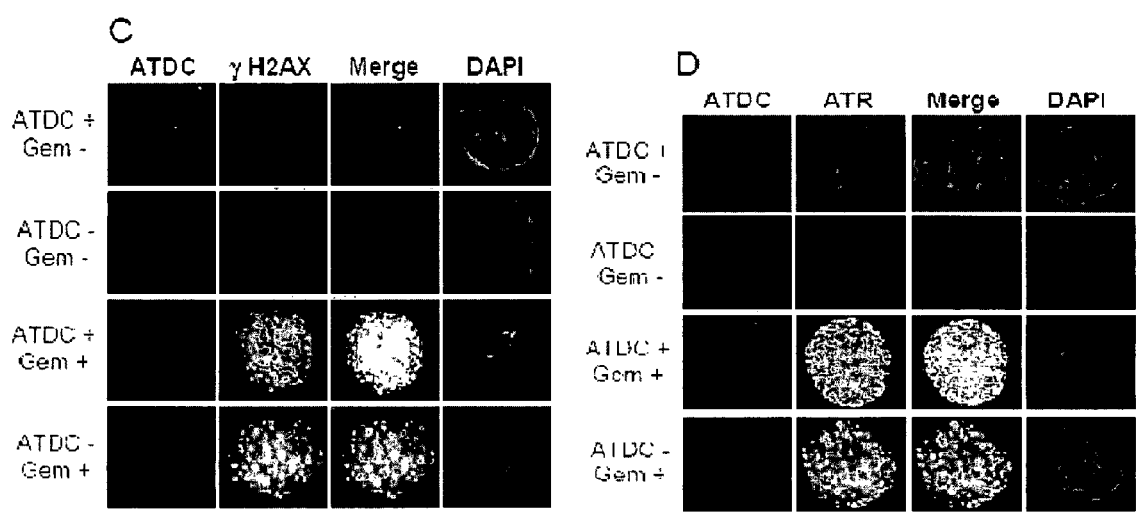
Figure 9:
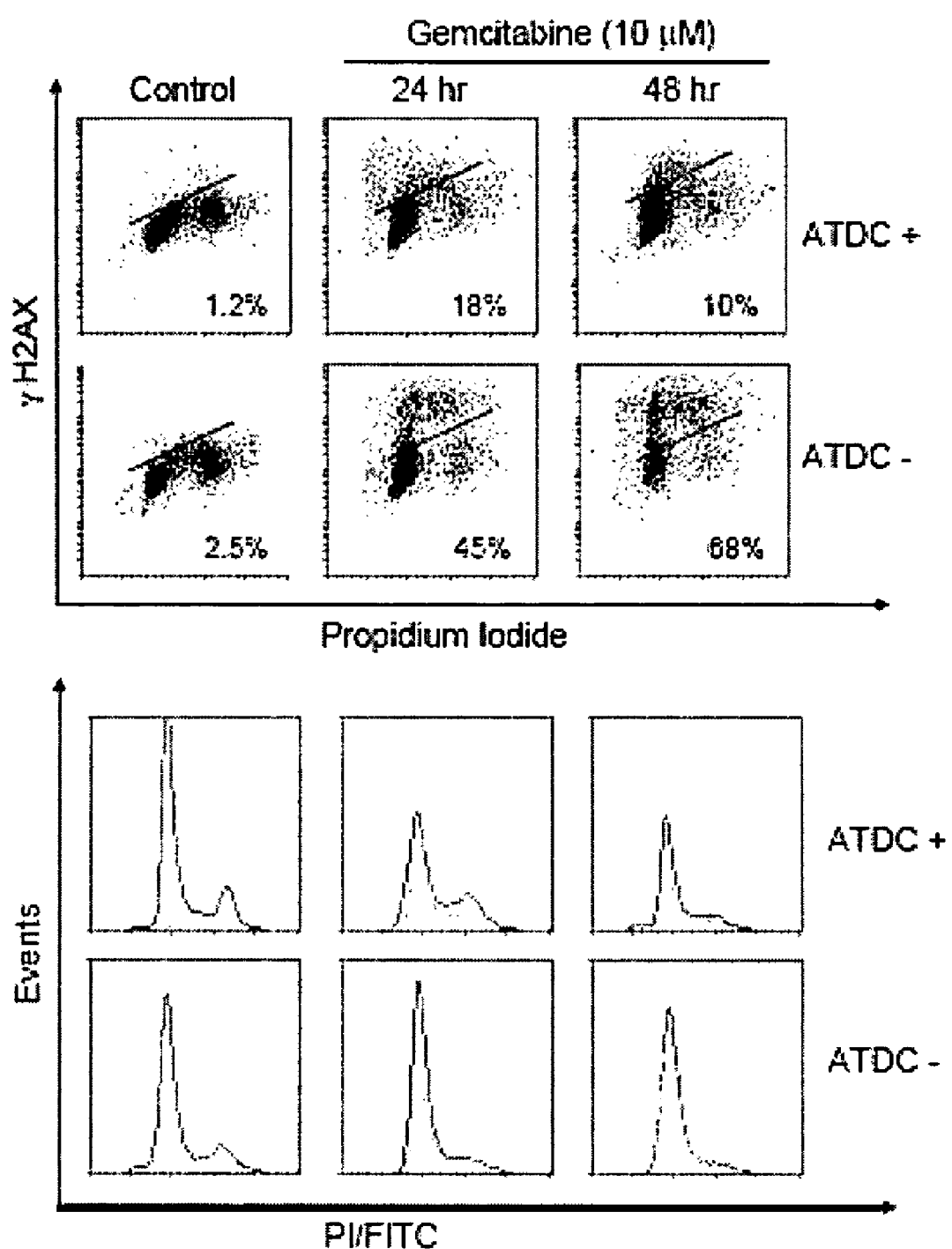
FIG. 9 shows H2AX phosphorylation caused by gemcitabine-induced stalled replication forks. Panc1 cells expressing control shRNA (ATDC+) or ATDC-silencing shRNA (ATDC−) were incubated with 10 µM gemcitabine for 24 to 48 hr, harvested, and subjected to fluorescent staining of γH2AX. Top, flowcytometric analysis of γH2AX and propidium iodide staining of DNA content. Percentages of γH2AX-positive cells are exhibited at low right corner. Bottom, comparison of the total DNA content of the population (black) versus the γH2AX-positive fraction (green). Results are representative of 3 separate experiments.

In response to IR, ATDC formed discrete nuclear foci as early as 5 minutes following irradiation which persisted for up to one hour (FIG. 8A). Using double immunofluorescence staining, it was observed that ATDC co-localized with γH2AX (FIG. 6A), presumably at DNA repair foci. In response to IR, ATM has been shown to undergo phosphorylation (p-ATM) and to traffic to DNA repair foci (see, e.g., Shinozaki T, et al., Oncogene 2003; 22: 8870-8880). ATDC co-localized with p-ATM following radiation treatment (FIG. 8B). The time course of ATDC localizing to DNA damage repair foci was similar to the time course of the formation of foci of phosphorylated H2AX and ATM. Whether ATDC is required for the formation of γH2AX and/or p-ATM foci in pancreatic cancer cells following IR was next investigated. Silencing of ATDC in Panc-1 cells did not alter the formation of γH2AX or p-ATM foci (FIGS. 8C, D) in response to 5 Gy IR (shown at 1 hour), suggesting that, for example, ATDC functions either downstream of the activation of ATM and the formation of γH2AX foci or via a parallel pathway.

Figure 7:
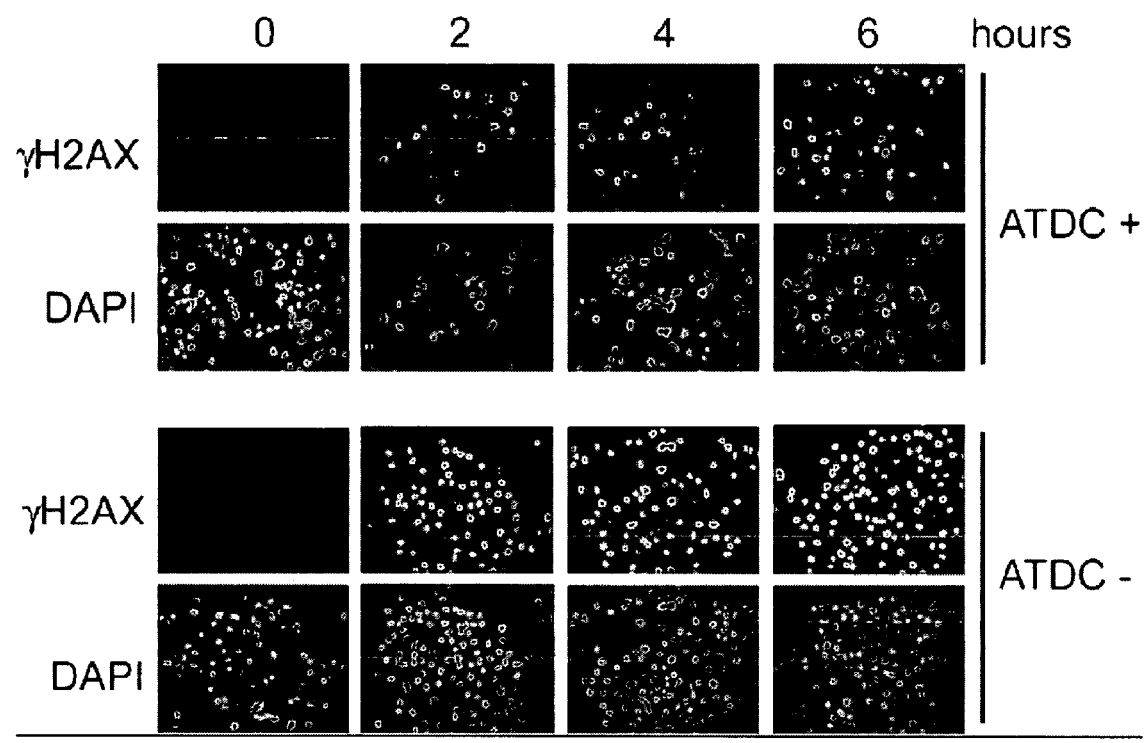
FIG. 7 shows knockdown of ATDC increases H2AX phosphorylation caused by gemcitabine treatment. To examine the effect ATDC silencing may have on the extent of stalled replication, Panc1 cells were treated with gemcitabine (10 mM) for indicated time intervals. The intensity of H2AX phosphorylation and the percentage of cells staining positive for phosphorylated H2AX were significantly increased in (ATDC−) cells.

It has been well-documented that in response to DNA damage, numerous proteins involved in the DNA damage response traffic to discrete nuclear foci. In response to treating Panc-1 cells with gemcitabine (amount/time), ATDC formed discrete nuclear foci (FIG. 7A). Using double immunofluorescence staining, it was observed that ATDC co-localized with γH2AX (FIG. 7A), presumably at DNA damage foci. In response to gemcitabine, ATR has been shown to traffic to DNA damage foci (see, e.g., Ewald B, et al., Mol Cancer Ther 2007; 6: 1239-1248). ATDC co-localized with ATR following gemcitabine treatment (FIG. 7B). The time course of ATDC localizing to DNA damage foci was similar to the time course of the formation of foci of phosphorylated H2AX. Whether ATDC is required for the formation of γH2AX and/or ATR foci in pancreatic cancer cells following gemcitabine was investigated. Silencing of ATDC in Panc-1 cells did not alter the formation of γH2AX or ATR foci as can be seen in FIGS. 7A and 7B in response to 50 uM gemcitabine, suggesting that, for example, ATDC functions either downstream of the activation of ATR and the formation of γH2AX foci or via a parallel pathway.

Figure 10:
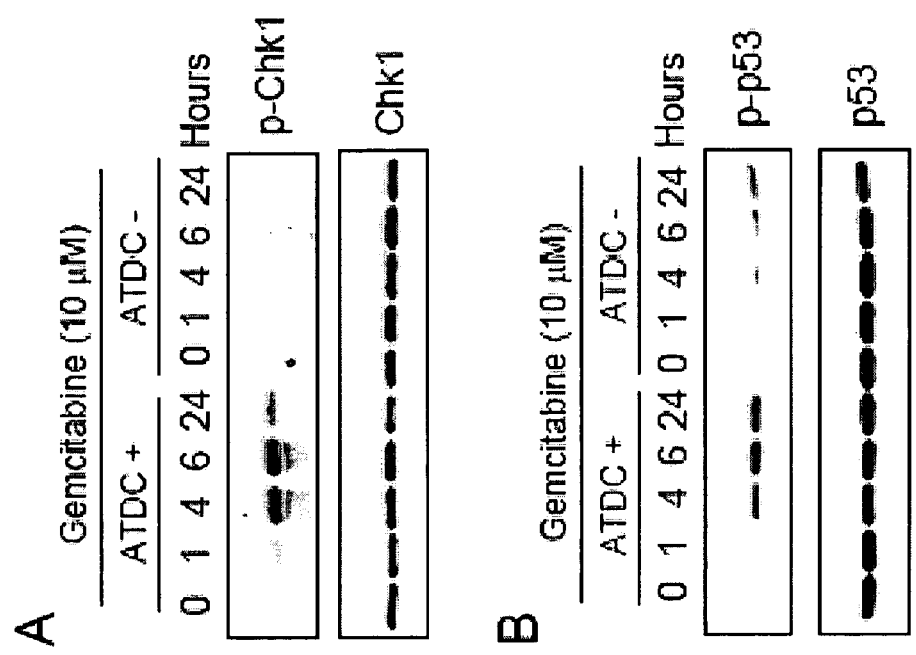
FIG. 10 shows silencing of ATDC by shRNA attenuates gemcitabine-induced phosphorylation of Chk1 and p53 in Panc1 cells.

To further investigate the role of ATDC in the DNA damage response, the effect of silencing ATDC on phosphorylation of p53 and Chk1 was investigated. In response to gemcitabine (10 μM), replication forks stall and the ATR signaling cascade is activated, which phosphorylates and activates several proteins critical to inducing the G1-S cell cycle checkpoint, including p53 and Chk1 (see, e.g., Ljungman M, Mutation Res 2005; 577: 203-216). Both p53 and Chk1 underwent phosphorylation in response to gemcitabine in control shRNA Panc-1 cells which was significantly decreased in ATDC-silenced Panc-1 cells, indicating that, for example, ATDC participates in cell cycle checkpoint signaling (FIG. 10). No changes were observed in total levels of p53 or Chk1.

Example V

Figure 11:
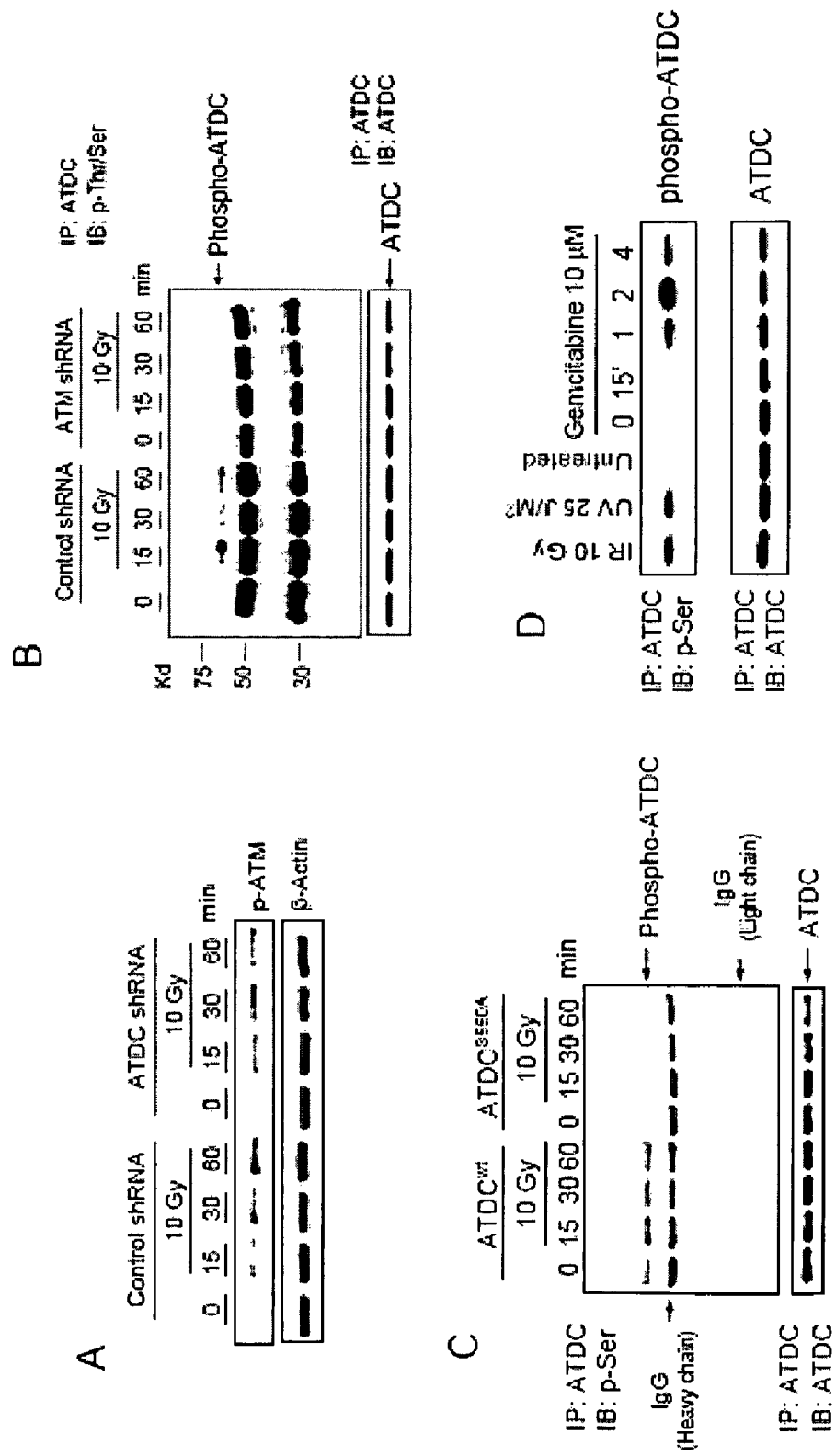
FIG. 11 shows IR, UV and gemcitabine induces ATDC phosphorylation. (A) Silencing of ATDC did not alter IR (10 Gy) induces ATM phosphorylation in Panc1 cells (n=3). (B) Knockdown of ATM by specific ATM shRNA prevents IR induced phosphorylation of ATDC in Panc1 cells (n=3). (C) IR-dependent phosphorylation of ATDC occurs at serine 550. HEK 293 cells over-expressing wild type or S550A mutant ATDC were treated with IR (10 Gy) for varyin times (0-60 min). Cell lysates were harvested and co-immunoprecipitation experiments were performed using anti-ATDC and anti-phospho-serine/threonine antibodies. Results are representative of three separate experiments (D) Gemcitabine induces phosphorylation of ATDC in transfected HEK293 cells.

This example demonstrates that ATDC is a phosphorylation target of ATM and possibly ATR. ATDC has overlapping function with ATM in cell cycle checkpoint activation and that trafficking of ATDC to DNA repair foci was dependent on ATM (see, e.g., FIGS. 4,6,7,8). ATDC had been shown previously to undergo phosphorylation on serine/threonine in A431 cells (see, e.g., Laderoute K R, et al., Int J Cancer 1996; 66: 772-778). It was hypothesized therefore that ATDC is a phosphorylation target of ATM and ATR. It is known that phosphorylation targets of ATM/ATR share a common motif, with either a serine or threonine residue, usually followed by a glutamine (the SQ or TQ motif) (see, e.g., Ziv Y, et al., Nature Cell Biol 2006; 8: 870-876). Examination of the amino acid sequence of ATDC revealed a SQ motif at amino acids 550-551. It was verified that ATDC functioned downstream of ATM, since silencing of ATDC had no effect on the phosphorylation of ATM in response to IR (FIG. 11A). Whether ATDC was phosphorylated in response to IR and if this phosphorylation was dependent on ATM was investigated. Co-immunoprecipitation experiments were performed in untreated and irradiated control and ATM-silenced Panc-1 cells using antibodies directed against ATDC and phosphoserine/threonine. It was found that silencing of ATM completely blocked phosphorylation of ATDC in radiation-treated cells (FIG. 11B), demonstrating that, for example, ATDC is a downstream phosphorylation target of ATM. Whether the SQ motif of ATDC is the preferred site of phosphorylation by ATM was investigated by irradiating HEK 293 cells that exogenously over-express either wild type ATDC or the ATDC mutant in which serine 550 has been mutated to alanine (ATDC(S550A)) and then analyzing the immunoprecipitated ATDC with a serine/threonine phospho-specific antibody. It was shown that the ATDC S550A mutant does not undergo phosphorylation following IR, suggesting that, for example, ATDC is a phosphorylation target of ATM at this site (FIG. 11C). It was also shown that ATDC is phosphorylated in response to both UV light and gemcitabine, both of which induce ATR signaling (FIG. 11D).

Example VI

Figure 12:
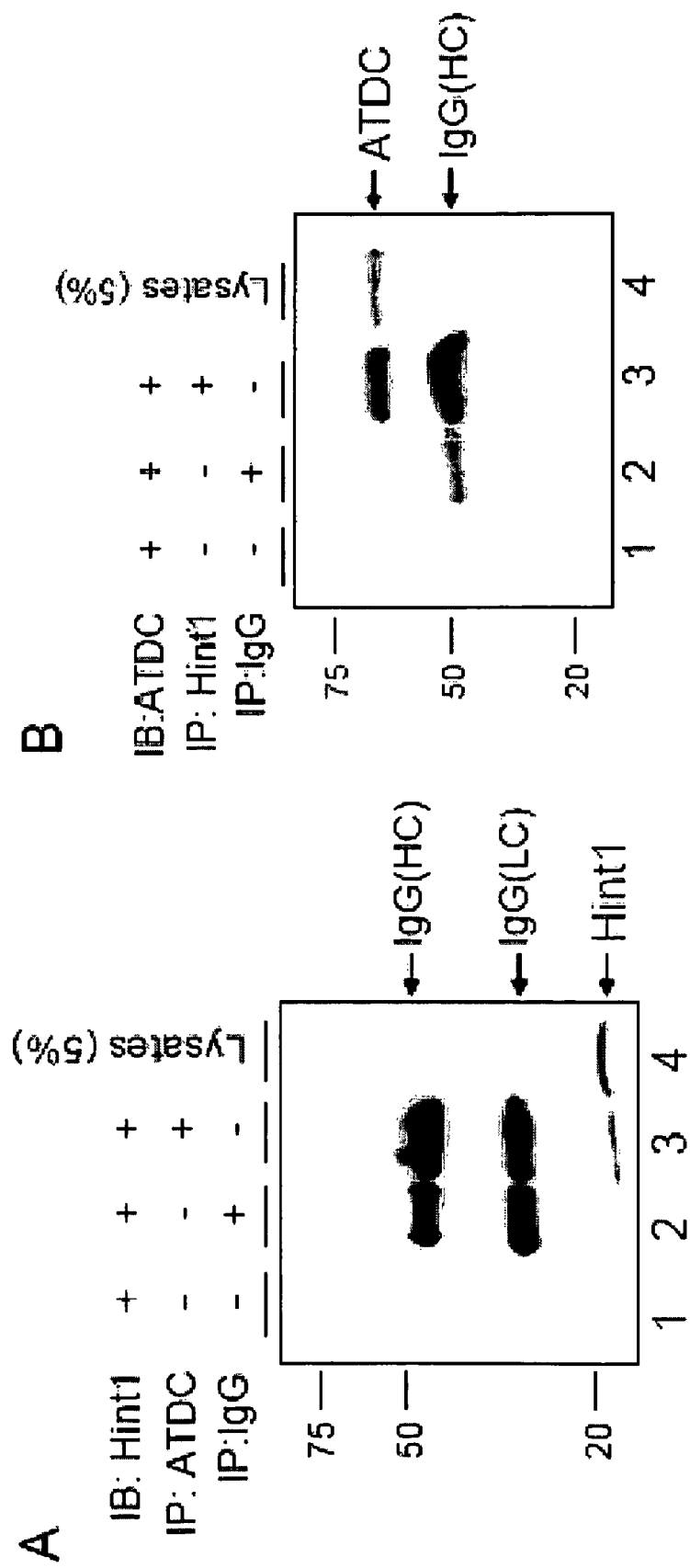
FIG. 12 shows ATDC interacts with HINT1. (A) Lysates from BxPC3 cells were immunoprecipitated with IgG or anti-ATDC antibodies and subjected to SDSPAGE immunoblotting with anti-HINT1 antibodies. (B) Lysates from BxPC3 cell were immunoprecipitated with IgG or anti-HINT1 antibodies and subjected to SDS-PAGE and immunoblotting with anti-ATDC antibodies. HC, heavy chain: LC, light chain.

This example demonstrates that ATDC and HINT1 are binding partners. One of the cellular functions of ATDC is to enhance cellular proliferation. It was hypothesized that ATDC promotes cellular proliferation through interaction with HINT1 and subsequent downstream effects on the β-catenin signaling pathway. To demonstrate that ATDC and HINT1 co-localize in pancreatic cancer cells, co-immunostaining using antibodies directed against both ATDC and HINT1 were performed, and co-localization of these proteins was observed. To show that ATDC physically binds to HINT1, co-immunoprecipitation experiments in BxPC-3 pancreatic cancer cells which have high endogenous levels of ATDC were performed, and binding of endogenous ATDC to HINT1 in the basal state was observed (FIG. 12). Similar results were observed with Panc-1 cells.

Example VII

Figure 13:
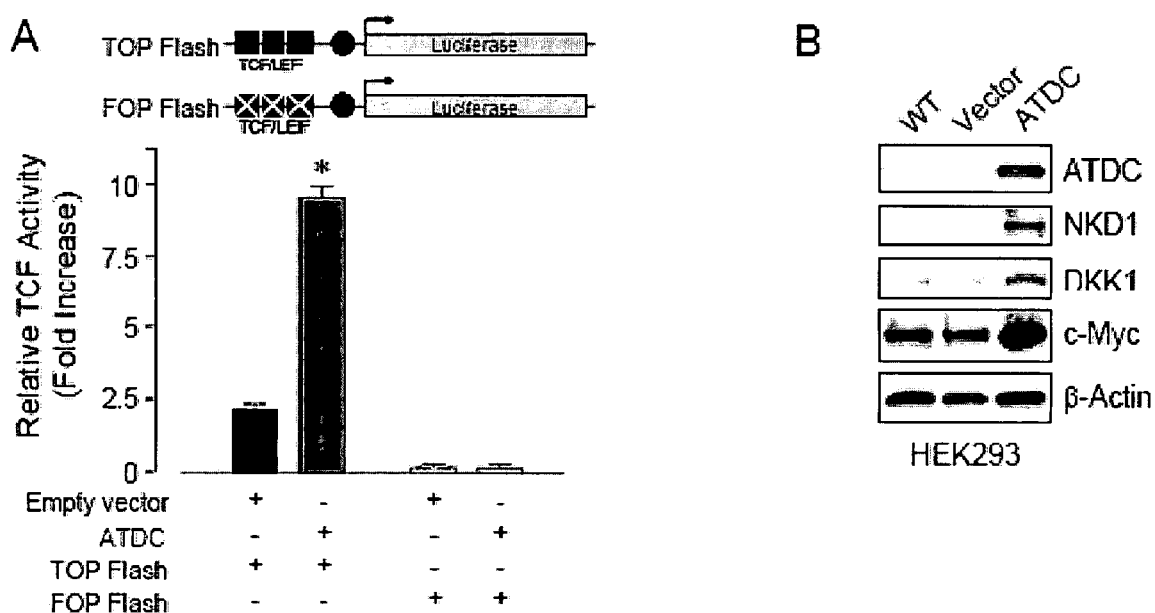
FIG. 13 shows overexpression of ATDC activates TCF/b-catenin signaling pathway. (A) HEK293 cells with or without ATDC expression were transfected with the TOP Flash and FOP Flash luciferase reporters and the relative luciferase activity was measured in three experiments (*p<0.05, HEK-ATDC vs HEKVector cells, n=3). (B) Lysates of HEK293 cells with or without ATDC expression were subjects to SDS-PAGE and immunoblotted with ATDC, Nkd1, DKK1 and c-Myc antibodies. Results representative of 3 different experiments.

This example demonstrates that ATDC stimulates β-catenin-mediated transcription. One of the cellular mechanisms that has been proposed to mediate the tumor suppressor function of HINT1 is inhibition of TCF-β-catenin-mediated transcription (see, e.g., Weiske J, et al., J. Cell Science 2005; 118, 3117-3129). To determine if ATDC may regulate the TCF-β-catenin pathway, whether ATDC overexpression could activate the TOP Flash luciferase reporter was investigated. It was determined that overexpression of ATDC resulted in enhanced β-catenin signaling (FIG. 13A). Furthermore, it was determined that several known direct target genes of the TCF/β-catenin complex, including Nkd1, DKK1 and c-myc were significantly upregulated in ATDC-expressing cells (FIG. 13B).

Example VIII

This example demonstrates that use of nanovectors to deliver ATDC shRNA to pancreatic tumors using an orthotopic model of pancreatic cancer. The transferrin receptor has been shown to be expressed at high levels on the surface of 93% of primary samples of human pancreatic cancer with no expression noted on pancreatic stromal, endothelial, or islet cells (see, e.g., Xu, L., et al., Molecular Cancer Therapeutics. 2002; 1: p. 337-46; Xu, L., et al., Human Gene Therapy., 2002. 13 (3): p. 469-81; Ryschich E, et al., Eur J Cancer 2004; 40; 1418-1422). A nanoscale, non-viral, liposome-based complex that includes an anti-transferrin receptor single chain antibody fragment as the targeting moiety can efficiently and specifically deliver siRNA to both primary and metastatic disease after systemic delivery using three separate in vivo tumor models, including pancreatic cancer (see, e.g., Xu, L., et al., Molecular Cancer Therapeutics. 2002; 1: p. 337-46; Xu, L., et al., Human Gene Therapy., 2002. 13 (3): p. 469-81; Pirollo K F, et al., Hum Gene Ther 2006; 17: 117-124). It was found that Tf-lipoplex nanovectors, when administered intravenously (3 injections of 32 mg of DNA within 24 hours) could efficiently deliver the LacZ reporter gene to a Panc-1 pancreatic xenograft tumor in the pancreas and at metastatic sites, with little/no delivery to normal organs, including the lung and liver, demonstrating the tumor specificity attributable to higher TfR levels in cancer cells than normal cells.

Figure 14:
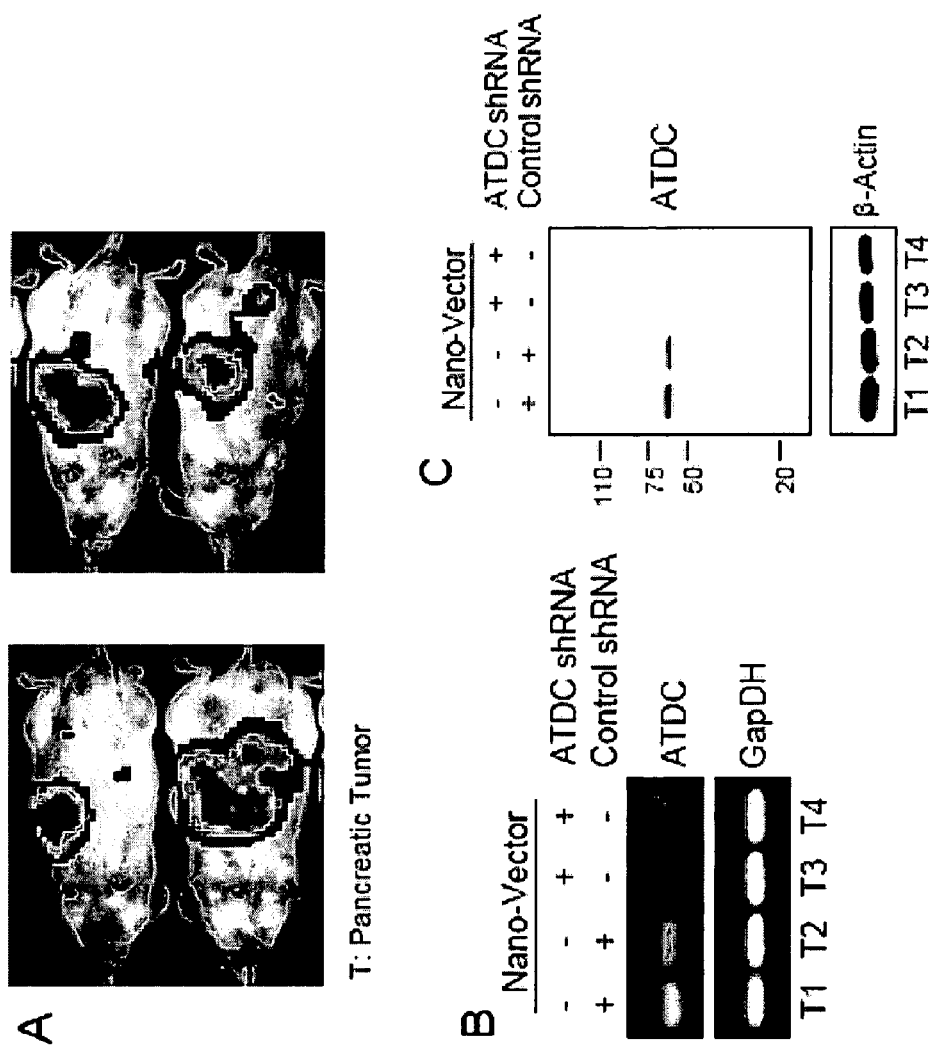
FIG. 14 shows ATDC shRNA-nanovectors knockdown of ATDC expression in BxPC-3 orthotopic xenograft models. (A) BxPC3 othotopic xenografts 1 week after injection of control shRNA-containing nano-liposome (left panel) or ATDC shRNA containing nano-lipsome (right panel) (n=2 per group). (B) Total RNA was extracted from tumors treated with control shRNA or ATDC shRNA nano-vector, and RT-PCR was performed with specific ATDC primers. (C) Lysates from tumors treated with control shRNA or ATDC shRNA plus nanovector were subjected to SDS-PAGE and immunoblotting with ATDC antibody.

These nanovectors have been used to target ATDC shRNA to human pancreatic cancer xenografts. To demonstrate the feasibility of this approach, i.v injections of the Tf-lipoplex containing either control shRNA or ATDC shRNA into mice with established BxPC-3 orthotopic tumors (n=2 per group) was performed (FIG. 14A). Briefly, to establish BxPC-3 orthotopic xenografts expressing luciferase to track tumor growth in real time in vivo, BxPC3 cells were infected with a lentiviral construct pLentiloxEV-Luc encoding luciferase. 48 hours after the lentivirus infection, the luciferase activity was assessed. Then, BxPC3-Luc cells were injected into the pancreatic tail ($10^6$ cells) of NOD-SCID mice, and the luminescence activity was measured once a week to suppose tumor sizes (0.5~0.7 cm in diameter). 3 weeks after implantation, Xenografts were split into the control or ATDC shRNA treatment groups, then ATDC-shRNA-nanovector or control-shRNA-GFP-nanovector were i.v. injected once a day for 4 days, 60 ug plasmid DNA/mouse each injection. The nanovectors were prepared freshly before injection, using transferrin as a targeting ligand, as described previously (see, e.g., Xu, L., et al., Molecular Cancer Therapeutics. 2002; 1: p. 337-46; Xu, L., et al., Human Gene Therapy., 2002. 13 (3): p. 469-81). On Day 5, xenografts and major organs were excised, and the tumor sizes were measured, and the each tumor was divided for total RNA extraction and protein lysis. The target gene ATDC knock-down by shRNA nanovectors was evaluated by Western blot and qRT-PCR.

Figure 15:
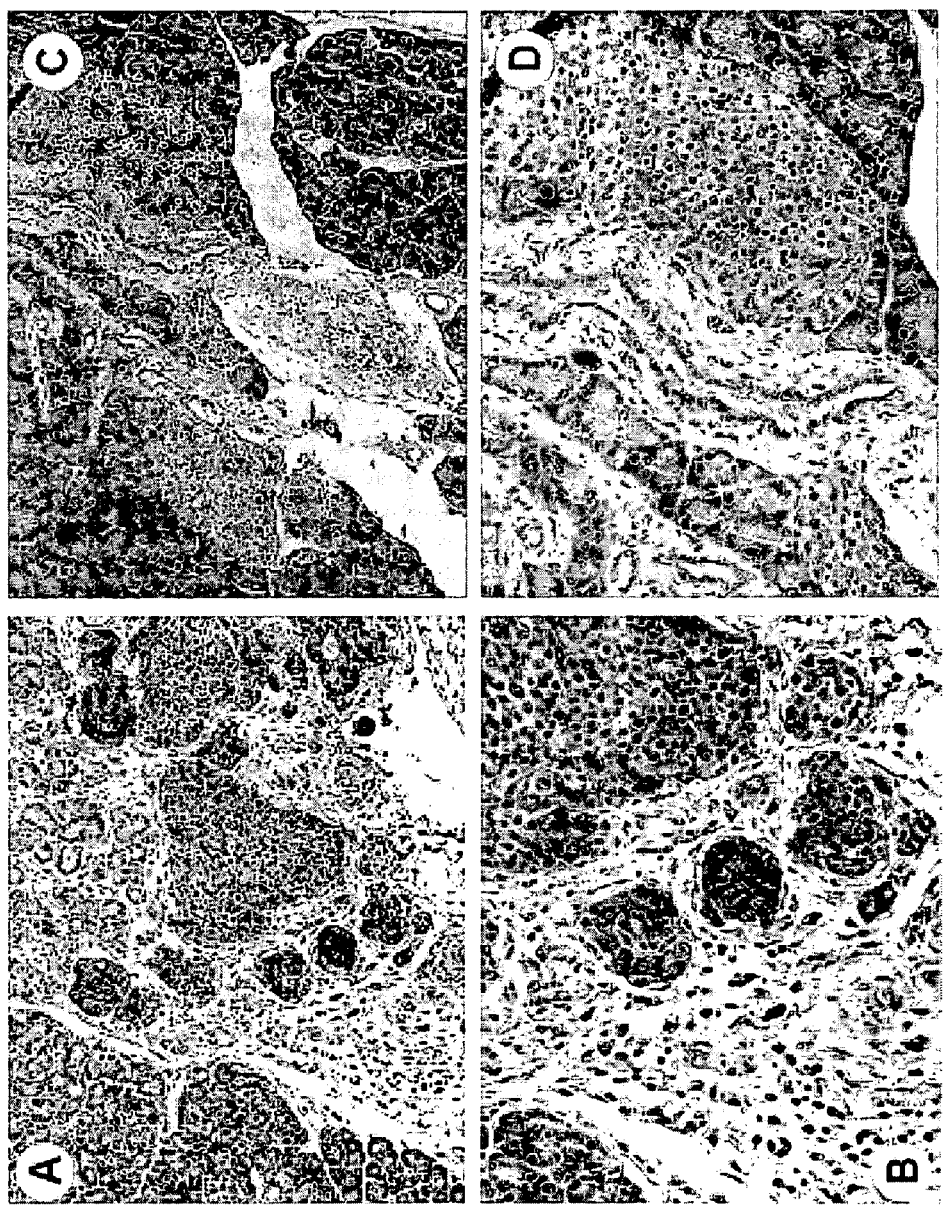
FIG. 15 shows immunohistochemistry (IHC) staining using anti-ATDC antibody in tumors treated with control shRNA nanovector (A) (40×), (B) (100×), or treated with ATDC shRNA nanovector (C) (40×), (D) (100×).

Semi-quantitative RT-PCR and Western blotting performed in these samples showed loss of ATDC expression in the tumors from animals injected with the nanovector containing ATDC shRNA (FIGS. 14B and 14C). As shown in this figure, all BxPC3 orthotopic xenografts generate the comparable sizes of tumors (T1, T2, T3, T4). A representative figure indicates two primary tumors in pancreas and the evidences of tumor metastasis in liver. The sizes of all the tumors are approximately 0.7~1.1 cm in diameter. It was also shown that nano-vector successfully deliver ATDC shRNA into the tumors. ATDC shRNA nearly abolishes ATDC mRNA and inhibits ATDC protein expression about 50~85% in BxPC3 xenografts, respectively. To investigate whether this targeting strategy was able to deliver the targeting construct to tumor cells within a tumor, immunohistochemistry on the tumors was performed, and ATDC expression measured. FIG. 15 shows that the nanovector complex containing ATDC shRNA was capable of decreasing ATDC expression in most of the tumor cells. This experiment demonstrates that, for example, Tf-lipoplexes can be used as a successful targeting strategy to silence ATDC in human pancreatic tumors in vivo.

In mice injected with control-shRNA-GFP-nanovector, qRT-PCR showed significantly increased expression of GFP mRNA, 40-250-fold more than ATDC-shRNA-nanovector which lacks GFP gene in the construct, indicating nanovector can efficiently deliver plasmid DNA to BxPC3 orthotopic tumors in vivo (FIG. 16A). Similar results were obtained in PANC-1 orthotopic model (FIG. 16B).

Example IX

This example demonstrates the efficacy of Nanovector delivered ATDC siRNA in human pancreatic cancer Panc-1 xenograft model in nude mice. Female athymic NCr-nu/nu nude mice about 5 to 6 weeks old, purchased from NCI, were inoculated subcutaneously (s.c.) on both sides of the lower back above the tail with $5 \times 10^6$ cells/0.2 ml of Panc-1 cells. Tumor volume was calculated using the formula $V=a \times b^2/2$, where a and b represented both the long and vertical short diameter of the tumor.

When tumors reached 70~100 mm$^3$, the mice were randomized and treated with Nanovector-siRNA for ATDC or control siRNA, 30 ug/mouse, i.v., 3/week for 5 weeks. Tumor size and body weight were measured twice a week.

Figure 17:
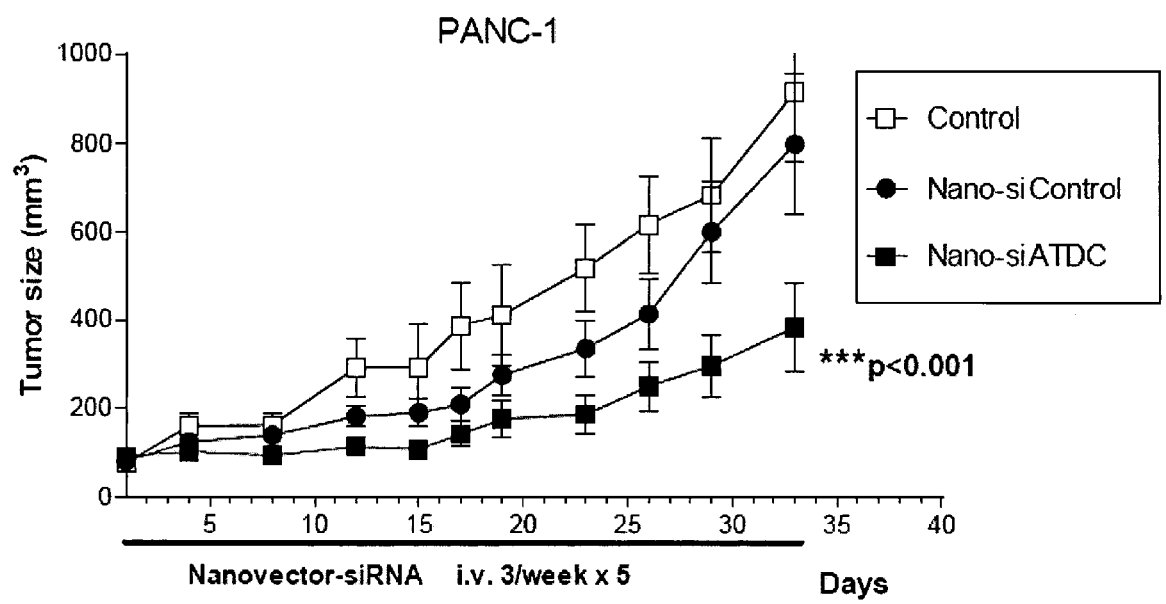
FIG. 17 shows tumor-targeted ATDC gene knock-down inhibited tumor growth in human pancreatic cancer Panc-1 xenograft model in nude mice. Female athymic nude mice were inoculated s.c. with 5×10⁶ Panc-1 cells on both sides near tail. When tumors reached 70~100 mm³, the mice were randomized and treated with Nanovector-siRNA for ATDC or control siRNA, 30 ug/mouse, i.v., 3/week for 5 weeks. Tumor sizes were measured twice a week, and curves were plotted. Nanovector-mediated ATDC siRNA significantly inhibited Panc-1 tumor growth, p<0.001 vs. that of control siRNA (n=8). Nano: Tf-Lipoplex nanovector.
Figure 18:
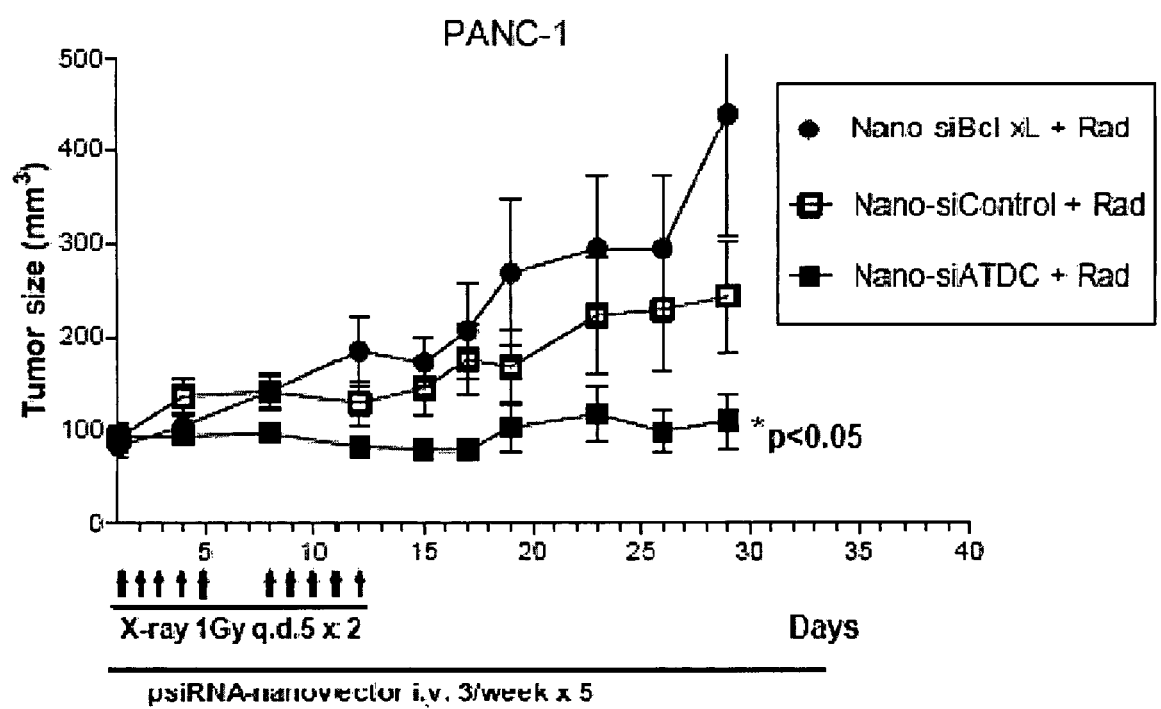
FIG. 18 shows tumor-targeted delivery of ATDC siRNA in combination of radiation completely inhibited Panc-1 tumor growth in vivo. Panc-1 xenograft model in nude mouse was as FIG. 17. When tumors reached 70~100 mm³, the mice were randomized and treated with Nanovector-siRNA for ATDC, Bcl-xL or control siRNA, 30 ug/mouse, i.v., 3/week for 5 weeks, or X-ray irradiation 1 Gy, q.d. 5×2 weeks, or combination. Nano: Tf-Lipoplex nanovector; Rad, X-ray radiation. Tumor sizes were measured twice a week, and curves were plotted. Nanovector-mediated ATDC siRNA plus radiation completely inhibited Panc-1 tumor growth, p<0.05 vs. control siRNA, p<0.001 vs. Bcl-xL siRNA, (n=8). Panc-1 appears not dependent on Bcl-xL for survival.

When tumors reached 70~100 mm$^3$, the mice were randomized and treated with Nanovector-siRNA for ATDC, Bcl-xL or control siRNA, 30 ug/mouse, i.v., 3/week for 5 weeks, or X-ray irradiation 1 Gy, q.d. 5×2 weeks, or combination. Tumor sizes were measured twice a week, and curves were plotted. FIG. 17 shows that nanovector-mediated ATDC siRNA significantly inhibited Panc-1 tumor growth, p<0.001 vs. that of control siRNA (n=8). FIG. 18 shows that nanovector-mediated ATDC siRNA plus radiation completely inhibited Panc-1 tumor growth, p<0.05 vs. control siRNA, p<0.001 vs. Bcl-xL siRNA, (n=8). Interestingly, Bcl-xL siRNA showed no effect on tumor growth, indicating that Panc-1 appears not dependent on Bcl-xL for survival, but dependent on ATDC.

Example X

This example provides evidence that ATDC functions in cancer cells through Wnt pathway activation and β-catenin stabilization. This example also demonstrates that the oncogenic effects of ATDC can be blocked through silencing expression of β-catenin or Dvl-2.

Experimental Procedures

Cell Lines and Human Samples

The human pancreatic ductal adenocarcinoma cell lines Panc1, Mia PaCa2 and BxPC3 and the human embryonic kidney cell line HEK 293 were purchased from American Type Culture Collection (ATCC, Manassas, Va.). Fresh frozen and paraffin-embedded human pancreatic tissues were obtained from patients undergoing surgical resection at the University of Michigan Medical Center. All human samples were obtained in accordance with the policies and practices of the Institutional Review Board of the University of Michigan Medical Center. A pancreatic cancer tissue microarray constructed by the University of Michigan Medical Center's Tissue Procurement Facility contained 5 samples of normal pancreas and 47 samples of pancreatic adenocarcinoma and was used for immunohistochemical analysis of ATDC expression. Twenty-five paraffin-embedded human pancreatic tissue samples containing pancreatic intraductal neoplasia (PanIn) lesions of various stages were analyzed for ATDC expression using an anti-ATDC antibody. ATDC expression in PanIn lesions was evaluated by an experienced pancreatic pathologist and graded as absent or present.

Constructs

The complementary DNA (cDNA) of human ATDC was subcloned into the pcDNA3.1 expression vector (Invitrogen, San Diego, Calif.). Sequence analysis after cloning showed 100% homology to the published sequence of ATDC. Two ATDC-specific short hairpin RNA (shRNA), directed against the human ATDC coding sequence and a missense shRNA to serve as a control were designed using the BLOCK-IT™ RNAi Designer Tool Program (Invitrogen, San Diego, Calif.) (See FIG. 21). Using a BLOCK-iT™ H1 RNAi entry vector kit (Invitrogen, San Diego, Calif.), the ds oligo duplexes of ATDC shRNA1, ATDC shRNA2 and missense control shRNA were cloned into the pENTR™/H1/TO expression vector using the manufacturer's instructions. The sequences of ATDC and control shRNAs were verified by sequence analysis. Endogenous Dvl-2 was knocked down by transient transfection of specific Dvl-2 shRNA1 and 2 (OriGene Technologies, Rockville, Md.) in HEK 293 and Mia PaCa2 cells with or without ATDC overexpression. A reporter plasmid carrying three TCF binding sites upstream of a minimal c-fos promoter driving the firefly luciferase gene (TOP Flash), the plasmid carrying the mutated TCF binding sites upstream of a minimal c-fos promoter driving luciferase expression (FOP Flash), and the expression constructs of wild type or constitutively active β-catenin containing a missense mutation of tyrosine for serine at codon 33 (S33Y) were used (Caca et al., 1999). The PGEX-2T vector containing C-terminal E-cadgherin/glutathione S-transferase (GST) was generated as previously described (Winer et al., 2006).

Creation of Stable Cell Lines

HEK 293 and MiaPaCa2 cell lines with stable expression of ATDC were generated by transfecting cells with a pcDNA3.1 vector containing ATDC. Control HEK 293 and MiaPaCa2 cell lines were generated by transfection with an empty pcDNA3.1 vector. Selection for neomycin resistance was initiated 48 hours after transfection by adding 500 μg G418/mL (Gibco BRL, Gaithersburg, Md.) to the culture medium. Selection media was changed every 3 days for 6 weeks and clones of G418-resistant cells were isolated and expanded for further characterization. To silence ATDC, Panc1 cells were stably transfected with ATDC shRNA1, ATDC shRNA2 and control shRNA expression vectors (shown in FIG. 28). Selection for zeocin resistance was initiated 48 hours after transfection by adding 400 μg/ml of zeocin to the culture medium. The selection media was changed every 3-4 days for several weeks, and clones of zeocin-resistant cells were isolated and expanded for further characterization. Silencing of ATDC expression in stably transfected cells was verified by western blotting using an anti-ATDC specific antibody (Santa Cruz Biotechnology, Santa Cruz, Calif.). Silencing of ATDC in BxPC3 pancreatic cancer cell line was achieved by transient infection with an ATDC shRNA retroviral vector generated in the University of Michigan Vector Core. Endogenous β-catenin was knocked down by stably transfection of specific β-catenin shRNA (OriGene Technologies, Rockville, Md.) in HEK 293 or Mia PaCa2 (with or without ATDC overexpression) or Panc1 cells (with or without ATDC silencing). Selection for puromycin (InvivoGen, San Diego, Calif.) resistance was initiated 48 hours after transfection by adding 5 ug/ml of puromycin to the culture medium. The selection media was changed every 3-4 days for several weeks, and clones of puromycin-resistant cells were isolated and expanded for further characterization. For in vivo bioluminescence imaging studies, Panc1 cells expressing control shRNA, β-catenin shRNA or ATDC-silencing shRNA were infected with the lentivirus construct pLentiloxEV-Luc expressing a luciferase reporter gene as described previously (Arumugam et al., 2005). TCF transcriptional activity was inhibited by transiently transfection of dominant negative TCF (dnTCF) vector in HEK 293, Mia PaCa2 (with or without ATDC overexpression) or Panc1 cells (with or without ATDC silencing). Dominant negative TCF cDNA in pcDNA 3.1 was obtained from Upstate (Temecula, Calif.).

Quantitative Real-Time RT-PCR

Total RNA from the human pancreatic ductal adenocarcinoma, normal pancreas and chronic pancreatitis specimens or Panc1 cells (with or without ATDC shRNA) were isolated using TRIzol reagent (Invitrogen, Carlsbad, Calif.). To avoid amplification of genomic DNA, RNA was pretreated with DNase (DNA-free kit from Applied Biosystems, Foster City, Calif.). cDNA synthesis was performed using a High Capacity cDNA Archive Kit (Applied Biosystems, Foster City, Calif.). The cDNA served as a template in quantitative real-time PCR utilizing TaqMan Fast Universal PCR Master Mix and TaqMan Gene Expression assay probes for ATDC (Hs00232590_m1), Dvl-2 (Hs01005253_m1) or ribosomal protein S6 (RPS6)(Hs02339423_g1) (Applied Biosystems Foster City, Calif.) and an ABI 7500 Fast Sequence Detection System. All reactions were done in triplicate. ATDC mRNA expression of different group specimens were normalized to endogenous ribosomal protein S6. Ct is the threshold cycle value defined as the fractional cycle number at which the target fluorescent signal passes a fixed threshold above baseline. Relative ATDC mRNA levels were presented as unit values of $2^{-\Delta Ct} = 2^{-(Ct(Ribosomal\ protein\ S6) - Ct\ (ATDC))}$.

Immunohistochemical Analysis

The paraffin-embedded pancreatic tissue sections (4-μm-thick) were cut, deparaffinized, and subjected to a heat-induced epitope retrieval step. Endogenous peroxidase activity was blocked with 1% (v/v) hydrogen peroxide in distilled water. To block unspecific binding, the sections were incubated with 1× Power Block (BioGenex, San Ramon, Calif.) for 5 minutes. Subsequently, samples were incubated with a goat polyclonal ATDC antibody raised against a peptide mapping to the C-terminus of ATDC antibody (catalogue number sc-1614, Santa Cruz Biotechnology, Santa Cruz, Calif.) or a β-catenin antibody (catalogue number 9562, Cell Signaling Technology, Beverly, Mass.), each diluted 1:100 in PBS for 30 minutes at 37° C. To serve as negative controls, sections were incubated with PBS without the primary antibody. For detection, specimens were sequentially incubated with biotinylated goat antimouse immunoglobulin G and streptavidin-horseradish-peroxidase. ATDC and β-catenin expression in stained sections were evaluated by an experienced pancreatic pathologist. For immunofluorescence staining, pancreatic cells (with or without silencing of ATDC) were seeded on chamber slides and allowed to grow 24 hours. Cells were then fixed for 5 min in ice-cold acetone/methanol (1:1). The cells were washed in PBS and incubated for 1 hour in TBS containing 5% goat or rabbit serum. Cells were incubated overnight at 4° C. with a β-catenin antibody (1:250 dilution). Slides were rinsed at least three times for 5 minutes in PBS, and then incubated with the secondary antibody fluorescein (FITC)-conjugated anti-rabbit IgG (Jackson, West Grove, Pa.) at a 1:1000 dilution for 1 hour at room temperature simultaneously. Slides were then counterstained with 4',6-diamidino-2-phenylindole (DAPI) and mounted with Vectashield (Vector Laboratories, Burlingame, Calif.). Immunofluorescence was visualized using an Olympus BX-51 fluorescence microscope.

Luciferase Reporter Gene Assays

Pancreatic cancer cells (with or without β-catenin silencing) or HEK 293 and Mia PaCa2 cells (with or without ATDC overexpression) were transfected using the LipofectAMINE 2000 Transfection kit (Invitrogen Carlsbad, Calif.) according to the manufacturer's instructions with 0.2 μg of the TOP-FLASH or FOPFLASH reporter constructs with or without varying amounts (0.2-2 μg) of constructs expressing either wild type β-catenin or the S33Y β-catenin (constitutively activated) mutant and 25 ng of a β-galactosidase construct as an internal control to normal luciferase activity to transfection efficiency. The total DNA for each transfection was kept constant by adding empty pcDNA vector. Forty eight hours after transfection, luciferase activity was measured in a luminometer and normalized to β-galactosidase expression. Endogenous β-catenin or Dvl-2 was silenced by stably expression β-catenin shRNA or transient expression of Dvl-2 shRNAs (OriGene Technologies, Rockville, Md.) in HEK293, Mia PaCa2 or Panc1 cells. TCF transcriptional activity was inhibited by transiently transfection of the dnTCF vector (Upstate, Temecula, Calif.).

Nuclear and Membrane Fractionation

Nuclear and cytoplasmic proteins were extracted using NE-PER Nuclear and Cytoplasmic Extraction Reagents (Pierce, Rockford, Ill.). Membrane proteins were extracted using the Mem-PER Eukaryotic Membrane Protein Extraction Kit (Pierce, Rockford, Ill.) according to the manufacturer's instructions.

C-terminal E-cadherin/Glutathione S-Transferase (GST) Fusion-Mediated Precipitation of the Free β-Catenin Pool The free pool of β-catenin in ATDC transfected and control HEK 293 cells was measured using a C-terminal E-cadherin/glutathione S-transferase fusion protein as previously described (Winer et al., 2006).

Immunoblot Analysis

Immunoblot analysis was done as previously described (Zhang et al., 2004) using antibodies directed against ATDC (Santa Cruz Biotechnology, Santa Cruz, Calif.), c-Myc, DKK1, disheveled-1 (Dvl-1) (Upstate, Temecula, Calif.), disheveled-2 (Dvl-2), disheveled-3 (Dvl-3), β-catenin (Cell Signaling Technology, Beverly, Mass.), GSK3β, Axin and anti-active β-Catenin (anti-ABC) (Upstate, Temecula, Calif.), all at a dilution of 1:1000. After analysis, the blots were stripped, washed and re-probed with a β-actin antibody (Sigma, St Louis, Mo.) to serve as a loading control. Protein expression was quantified using a Kodak Gel Documentation System (model ID 3.6).

Immunofluorescence Staining

HEK 293 cells with or without ATDC overexpression were seeded on chamber slides and allowed to grow 24 hours. The slides were washed in PBS and incubated for 1 hour in TBS containing 5% goat and rabbit serum. For double-immunolabeling experiments, the primary antibodies ATDC (anti-goat) (1:250) and Dvl-2 (anti-rabbit) (1:500 dilution) were incubated simultaneously overnight at 4° C. Slides were then rinsed at least three times for 5 minutes in PBS, and then incubated with the double secondary antibodies Rhodamine Red™-X-conjugated anti-goat IgG (Jackson, West Grove, Pa.), Fluorescein (FITC)-conjugated anti-rabbit IgG (Jackson, West Grove, Pa.) or FITC-conjugated anti-mouse IgG (Jackson, West Grove, Pa.) at a 1:1000 dilution for 1 hour at room temperature simultaneously. Finally, slides were counterstained with 4',6-diamidino-2-phenylindole (DAPI) and mounted with Vectashield (Vector Laboratories, Burlingame, Calif.). Immunofluorescence was visualized by using an Olympus BX-51 fluorescence microscope.

Proliferation Assay

Cell proliferation was measured using a CellTiter 96 AQ nonradioactive cell proliferation assay (Promega, Madison, Wis.) as we have previously described (Zhang et al., 2004).

Co-Immunoprecipitation Experiments

HEK 293 cells with or without stable transfection of ATDC and BxPC-3 cells were lysed by sonicating for 5 sec in 1 ml of detergent free lysis buffer (PBS, 5 mM EDTA, 0.02% sodium azide, 10 mM iodoacetamide, 1 mM PMSF and 2 µg leupeptin) at 4° C. The lysates were cleared by microcentrifuging for 15 minutes at 16,000×g at 4° C. Antibody conjugated beads were prepared by combining 1 µg of polyclonal antibodies with 30 µl of a 50% protein A-Sepharose bead slurry in 0.5 ml of ice-cold PBS for 1 hr at 4° C. in a tube rotator and then were washed two times with 1 ml of lysis buffer. The antibodies used for co-immunoprecipitation were: Dvl-2, β-catenin (Cell Signaling Technology, Beverly, Mass.), axin, and GSK3β (Upstate, Temecula, Calif.). Cell lysates (500 µg) was incubated with the prepared beads and 10 µl of 10% BSA overnight at 4° C. The beads were washed four times with washing buffer (50 mM Tris-Hcl [pH 7.4], 300 mM NaCl, 5 mM EDTA, 0.02% sodium azide, 0.1% Triton X-100) and one time with ice-cold PBS. Proteins were revealed after SDS-PAGE and Western blotting with the following antibodies: Flag (Sigma, St Louis, Mo.), Dvl-2, β-catenin (Cell Signaling Technology, Beverly, Mass.), axin, GSK3β (Upstate, Temecula, Calif.), and ATDC (Santa Cruz Biotechnology, Santa Cruz, Calif.). Images were visualized using an ECL detection system.

Pulse Chase Assays

Panc1 cells (with or without ATDC silencing) were cultured in 6 well plates to 70% confluence. Cells were starved in 2 ml methionine-deficient DMEM (Sigma; Madison, Wis.) for 30 min at 37° C. with 5% $CO_2$. Cells were then pulse-labeled with 100 µCi/ml [$^{35}$S]-methionine (Amersham Pharmacia, Pittsburgh, Pa.) for 30 minutes at 37° C. Labeled cells were chased in DMEM with a saturating amount of cold methionine (2 mM) for various times and lysed in RIPA buffer (10 mM Tris, pH 7.2, 158 mM NaCl, 1 mM EGTA, 1% Triton X-100, 1% deoxycholate, 0.1% SDS, 1 mM PMSF, and 1× concentration of protease inhibitors (Complete Protease Inhibitor Cocktail, Roche Molecular Biochemicals)). Total cell lysates were then prepared and immunoprecipitated with a β-catenin antibody (Cell Signaling Technology, Beverly, Mass.) or Dvl-2 antibody (Cell Signaling Technology, Beverly, Mass.) and protein G-Sepharose beads (Invitrogen, San Diego, Calif.) for 3 hours at 4° C. Immunocomplexes were separated on SDS-PAGE (4-20% gradient gel) and transferred to nitrocellulose. The precipitates were subjected to autoradiography, and then the densities of the labeled proteins were analyzed by Kodak Gel Documentation System (model ID 3.6).

In Vivo Tumorigenicity Studies

Six-week-old male NOD/SCID (non-obese diabetic/severe combined immunodeficient) mice (Taconic, Germantown, N.Y.) were housed under pathogen-free conditions in accordance with University of Michigan Animal Care and Use Committee Guidelines. Mice were anesthetized with an i.p. injection of xylazine (9 mg/kg) and ketamine (100 mg/kg). A median laparotomy was done and 5×10$^5$ Panc1 cells infected with a lentivirus encoding luciferase (control shRNA, ATDC-shRNA1 or β-Catenin shRNA stably transfected) in a volume of 30 µl were injected into the pancreatic tail using a 30-gauge needle (n=8 per group). In the first set of in vivo experiments, Panc1 cells stably expressing control or ATDC shRNA were used. In the second set of in vivo experiments, Panc1 cells expressing control or β-catenin shRNA were used. To prevent leak at the injection site, the needle was slowly withdrawn and a sterile cotton swab was applied to the injection site for 30 sec. Bioluminescent imaging of the mice was performed bi-weekly using a Xenogen IVIS 200 imaging system (Xenogen Biosciences, Cranbury, N.J.) to assess tumor development. To validate the findings with bioluminescent imaging, 60 days following cancer cell injection, mice were euthanized with carbon dioxide inhalation, and autopsies were performed to assess the extent of primary tumor growth and metastasis.

Results

ATDC Activates the Wnt/β-Catenin/TCF Signaling Cascade

Figure 22:
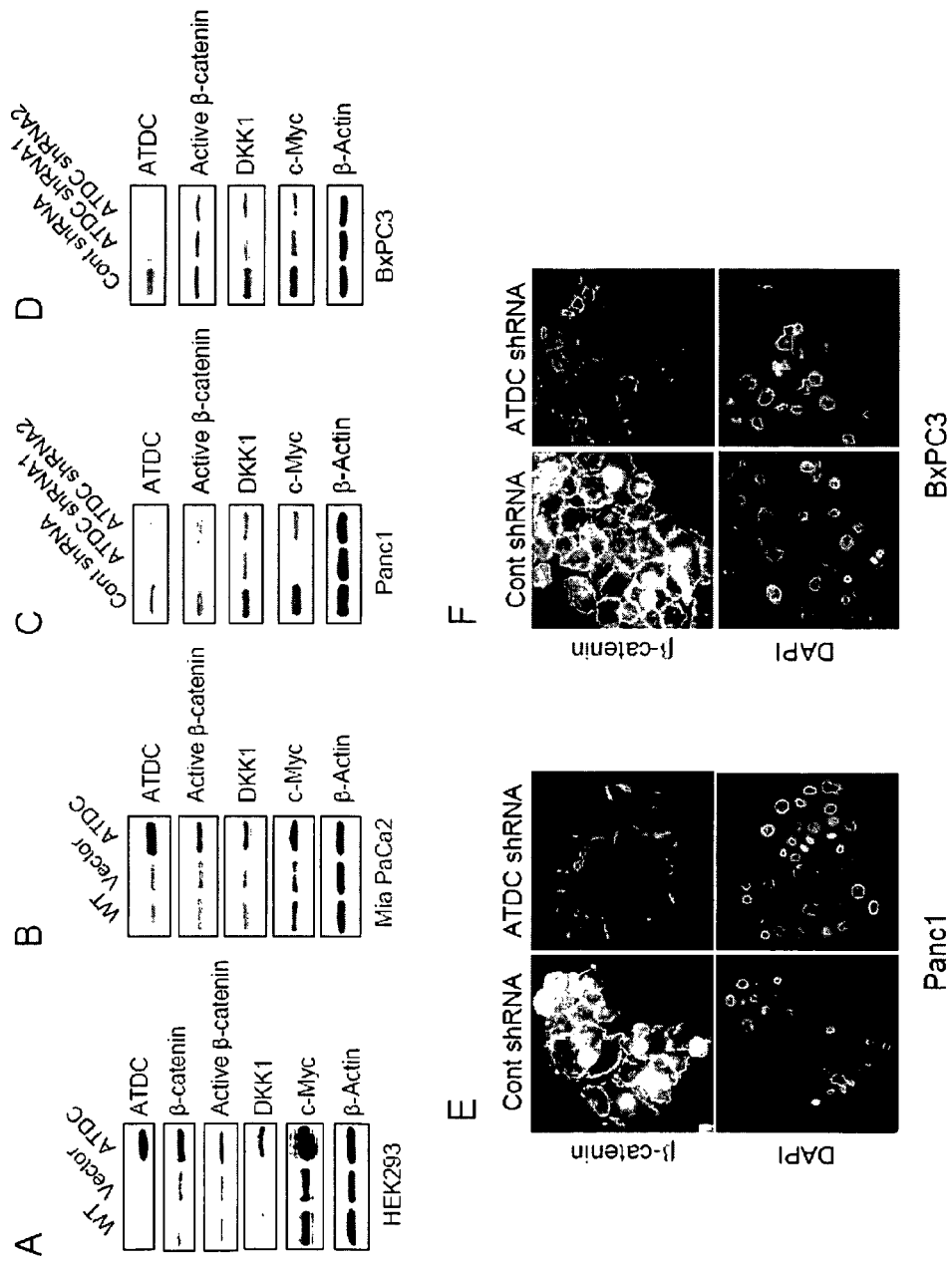
FIG. 22. ATDC upregulates β-catenin levels and TCF transcriptional activity. (A, B) Representative Western blots of wild type, empty vector, and ATDC-transfected HEK 293 (A) and MiaPaCa2 cells (B), cells lines which express little/no endogenous ATDC expression. Overexpression of ATDC results in upregulation of β-catenin, active β-catenin, and the TCF target genes DKK1 and c-Myc. β-actin was used as a loading control. (C, D) Representative Western blots of Panc1 (C) and BxPC3 (D) cells expressing control shRNA, ATDC shRNA1 or ATDC shRNA2. Silencing of ATDC in Panc1 and BxPC3 cells decreases levels of active β-catenin and the TCF target genes DKK1 and c-Myc. β-Actin serves as a loading control. (E, F) Photomicrographs of control shRNA- and ATDC shRNA1-expressing Panc1 cells (E) and BxPC3 cells (F) immunostained with an anti-O-catenin antibody. Cell nuclei were counterstained with DAPI. (G) TCF reporter activity was assessed by using the β-catenin responsive TOP-FLASH reporter and the mutant control FOPFLASH reporter in HEK 293 cells stably transfected with empty vector or an ATDC expression vector. The results from 3 separate experiments, performed in triplicate (*p<0.05 vs empty vector-transfected cells). (H) The GST-E-cadherin (GST-Ecad) fusion protein detects increases in the free pool of β-catenin. HEK 293 cells expressing ATDC or S33Y β-catenin (S33Y) were harvested. Free β-catenin levels were assessed by western blotting of GST-Ecad-bound fractions of 500 ug of total lysate using a specific anti-β-catenin antibody. β-actin (input) was used as a loading control. (I) Up-regulation of β-catenin by ATDC in subcellular protein fractions in HEK 293 cells. Membrane, cytoplasmic and nuclear protein fractions from transfected HEK293 cells were isolated, and western blot analyses were performed. The representative blots show β-catenin levels in membrane (Mem), nuclear (Nuc) and cytoplasmic (Cyto) fractions and total lysates (Lys). β-actin (cytoplasmic expression) and fibrillarin (nuclear expression) were used as loading controls.
Figure 22:
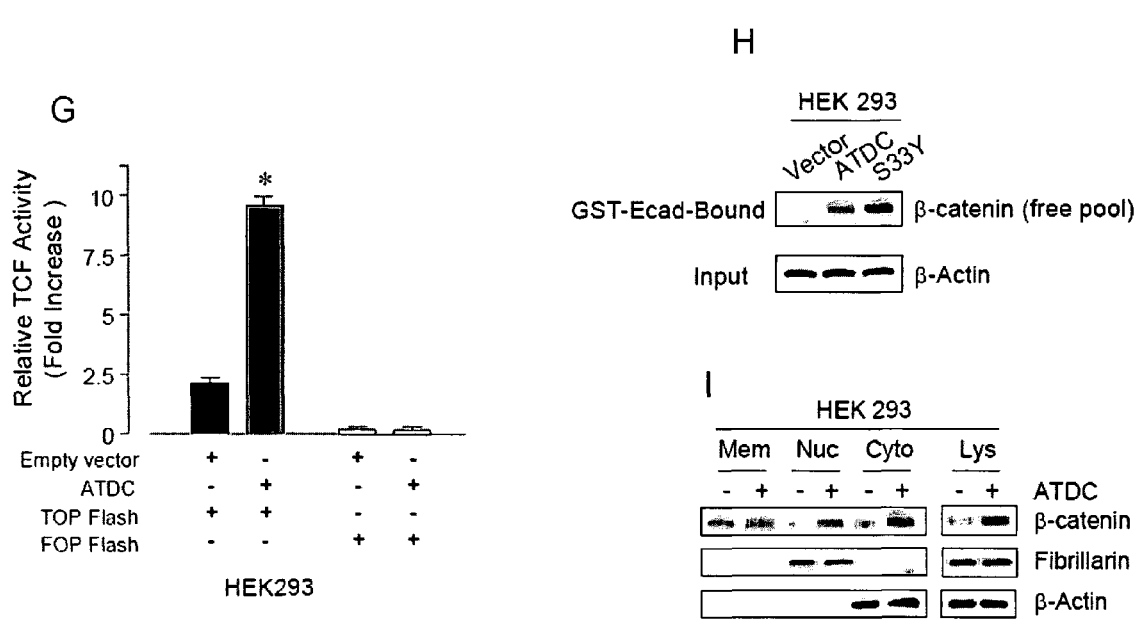

In exploring possible downstream mediators of ATDC's growth-promoting effects, it was noted that over-expression of ATDC resulted in a significant increase in β-catenin levels in HEK 293 cells (FIG. 22A). It was also found that over-expression of ATDC increased expression of the under- or non-phosphorylated forms of β-catenin ("active" β-catenin) presumed to be the forms of β-catenin responsible for mediating Wnt signaling in cells (van Noort et al., 2002) (FIG. 22A). Similar results were obtained in Mia PaCa2 pancreatic cancer cells ectopically expressing ATDC (FIG. 22B). Conversely, ATDC shRNA1- or 2-mediated silencing of endogenous ATDC expression significantly decreased total β-catenin and active β-catenin levels in Panc1 cells (FIGS. 22C, 22E) and BxPC3 cells (FIGS. 22D, 22F).

The active form of β-catenin exerts its growth promoting effects by translocating from the cytoplasm to the nucleus, where it binds to transcription factors such as the TCF/lymphoid enhancer binding factor and thereby stimulates the transcription of Wnt target genes. (Clevers, 2006). Over-expression of ATDC in HEK 293 and MiaPaCa2 cells increased expression of the Wnt/β-catenin target genes c-Myc and DKK1 (FIG. 22A, 22B), while c-Myc and DKK1 levels were significantly reduced in Panc1 and BxPC3 cells expressing ATDC-targeting shRNA1 or 2 (FIGS. 22C, 22D). Consistent with the ability of ATDC to increase β-catenin and active β-catenin levels in HEK 293 cells, we found that ATDC strongly activated the TCF-dependent TOP-FLASH reporter construct in HEK 293 cells (FIG. 22G). Together, these results strongly suggest that ATDC enhances β-catenin levels and activates β-catenin/TCF target gene expression in pancreatic cancer cells.

ATDC Increases the Free Intracellular Pool of β-Catenin Through Activation of the Canonical Wnt Signaling Pathway To address in more detail the means by which ATDC increased β-catenin/TCF-regulated gene expression, the abundance of the free pool of β-catenin in ATDC-expressing cells compared to control cells was assessed. To measure the free pool of β-catenin, a recombinant GST fusion protein containing the cytoplasmic tail of E-cadherin (GST-Ecad) was utilized. It has been previously shown that GST-E-cadherin can readily be used to monitor the abundance of the free pool of β-catenin that is stabilized in response to activation of the Wnt signaling pathway (Winer et al., 2006). As show in FIG. 22H, following ectopic expression of ATDC or the S33Y mutant form of β-catenin in HEK 293 cells, significant increases in the levels of the free β-catenin pool were seen, as demonstrated by the recovery of β-catenin with GST-E-cadherin. In contrast, no significant β-catenin was recovered from control cell lysates following incubation with the GST-E-cadherin.

To confirm that the increase in the free pool of β-catenin seen with ATDC overexpression was associated with increased cytoplasmic and nuclear levels of β-catenin, extracts from control and ATDC-overexpressing HEK 293 cells were separated into membrane, cytoplasmic, and nuclear fractions and the relative abundance of β-catenin in these fractions analyzed. ATDC overexpression increased both the nuclear and cytoplasmic fractions of β-catenin, while having no effect on the membrane bound fraction of ATDC (FIG. 22I). These results suggest that increased levels of ATDC affect β-catenin levels and β-catenin/TCF-dependent transcription in a fashion similar to that seen following activation of the canonical Wnt signaling pathway.

Figure 23:
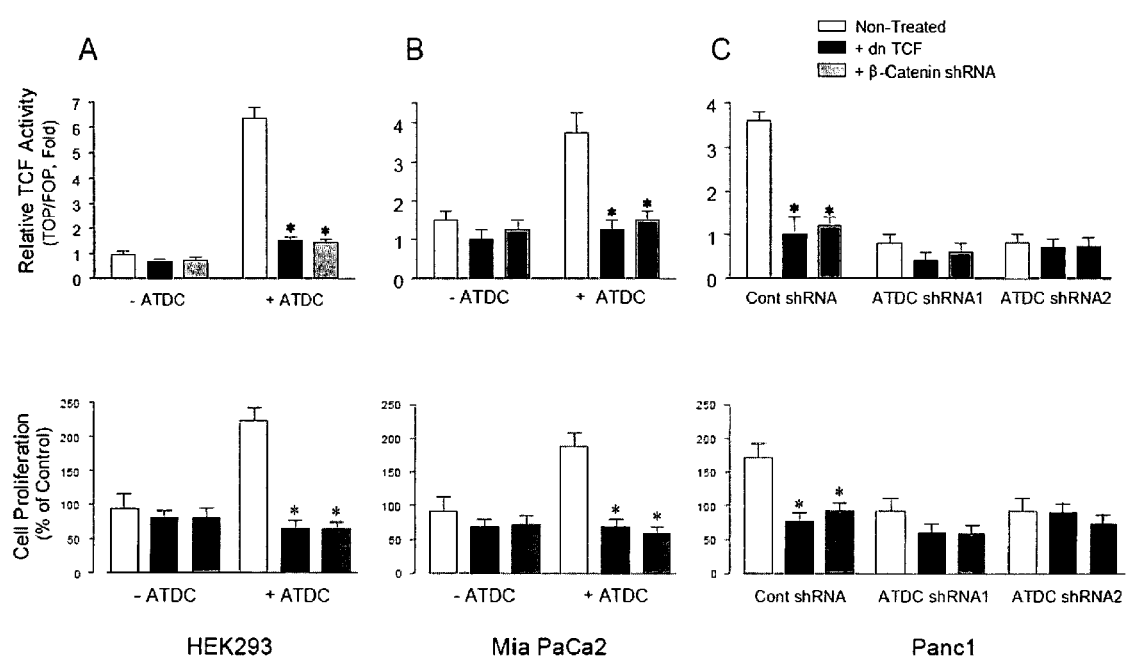
FIG. 23. ATDC stimulates cell proliferation and tumor growth via β-catenin/TCF activation. (A, B, C) In the upper panels, TCF reporter activity was measured in HEK 293 cells (A), MiaPaCa2 cells (B), and Panc1 cells (C) using the β-catenin responsive TOPFLASH reporter and the mutant control FOPFLASH reporter. The mean of the TOP/FOP ratio, as compared with the activity of the non-treated HEK 293 control cells, for three independent experiments, performed in triplicate, is shown. In (A) and (B), empty vector and ATDC expression vector-transfected HEK 293 (A) and MiaPaCa2 (B) cells are shown, while in (C), control shRNA- and ATDC shRNA1 or 2-transfected Panc1 cells are shown. The effects of stable transfection of cells with dnTCF (black bars) and β-catenin shRNA (gray bars) on relative TCF activity is shown (n=3, *p<0.05 vs control, non-treated cells). In the lower panels, cell proliferation of empty vector- and ATDC expression vector-transfected HEK 293 cells (A, lower panel) and MiaPaCa2 cells (B, lower panel), and control shRNA- and ATDC shRNA1 or 2-expressing Panc1 cells (C, lower panel) are shown. The effects of stable transfection of cells with dnTCF (black bars) and β-catenin shRNA (gray bars) on cell proliferation is shown (n=3, *p<0.05 vs control, non-treated cells). (D) $5 \times 10^5$ control shRNA- or β-catenin shRNA-transfected Panc1 cells infected with a luciferase-expressing lentivirus were directly injected into the pancreatic tail of NOD/SCID mice (n=eight animals per group). Representative bioluminescent images of three of the animals in each group are shown at 14 (left panels) and 60 (right panels) days after injection, depicting the extent of tumor burden. (E) Western blotting verifies downregulation of β-catenin in tumors derived from β-catenin shRNA transfected Panc1 cells (harvested at 60 days). (F) Average tumor volume measured in animals injected with control shRNA- and β-catenin shRNA-transfected Panc1 cells at 60 days post-injection (mean±SE, n=3, *p<0.05).

ATDC Stimulates Cell Proliferation and Tumor Growth Via β-Catenin/TCF Activation It was then sought to determine if the growth-promoting effects of ATDC were mediated by activation of the β-catenin signaling pathway. Constitutive activation of Wnt/β-catenin signaling by mutations in known Wnt pathway components, such as inactivating mutations in the APC (adenomatous polyposis coli) or Axin1 tumor suppressor genes or activating mutations in β-catenin are commonly seen in certain cancers, such as colorectal or hepatocellular carcinomas, but are rarely seen in pancreatic adenocarcinoma (Gregorieff et al., 2005; Lustig et al., 2003). However, constitutive activation of β-catenin/TCF-dependent transcription, independent of mutations, has been suggested to play an important role in the development of certain human breast and ovarian cancers (Bafico et al., 2004) and in a mouse model of pancreatic cancer (Pasca di Magliano et al., 2007). To address the contribution of β-catenin/TCF transcription in the growth-promoting effects of ATDC, a β-catenin shRNA or a dominant negative TCF (dnTCF) protein was ectopically expressed in either control vector-transfected or ATDC-expressing HEK 293 and MiaPaCa2 cells. Transfection of either the β-catenin shRNA or dnTCF constructs significantly inhibited ATDC-induced TOPFLASH reporter activity in HEK 293 and MiaPaCa2 cells (FIGS. 23A and 23B, upper panels). In addition, inhibition of β-catenin/TCF function abolished ATDC-stimulated cell proliferation in both the HEK 293 and MiaPaca2 cell lines (FIGS. 23A and 23B, lower panels). Similarly, transfection of β-catenin-targeting shRNA or dnTCF in Panc1 cells inhibited TOPFLASH reporter activity due to high levels of endogenous ATDC in Panc1 cells (FIG. 23C, upper panel) and inhibited the enhanced cellular proliferation seen in Panc1 cells in the setting of high endogenous ATDC levels (FIG. 23C, lower panel).

To examine the effects of β-catenin silencing on pancreatic tumor growth and metastasis in vivo, control or β-catenin shRNA-transduced Panc1 cells were infected with a luciferase-expressing lentivirus. Following injection of $5 \times 10^5$ cells into the tail of the pancreas, tumor growth was assessed using bioluminescent imaging (n=8 animals per group). All of the animals injected with Panc1 cells expressing control shRNA demonstrated tumor formation 14 days post-injection, while tumors were not detected in the animals injected with Panc1 cells expressing the β-catenin shRNA (FIG. 23D, left panels, with three representative animals shown). At 60 days post-injection, the tumors injected with control cells grew significantly larger, with evidence of metastatic spread, while the extent of primary tumor size and metastasis was markedly diminished in animals injected with Panc1 cells expressing the β-catenin shRNA (FIG. 23D, right panels), similar to the effects observed with silencing ATDC in Panc1 cells (FIG. 23E). Western blot analysis of tumors derived from β-catenin shRNA-transfected Panc1 cells harvested at 60 days after injection (FIG. 23E) demonstrated effective silencing of β-catenin (FIG. 23E). The mean tumor volume was significantly larger in the mice injected with Panc1-Luc cells expressing control shRNA compared to mice injected with Panc1-Luc cells expressing β-catenin shRNA ($251.5 \pm 79.2$ vs. $35.2 \pm 7.8$ mm$^3$, respectively, *$p<0.05$) (FIG. 23F). While the present invention is not limited to any mechanism and an understanding of the mechanism is not necessary to practice the present invention, overall, these data indicate that ATDC has a key role in cell proliferation and tumor growth, and ATDC's growth promoting effects are dependent, at least in part, on the β-catenin/TCF signaling pathway.

Correlation Between ATDC and β-Catenin Expression in Pancreatic Adenocarcinoma

Figure 24:
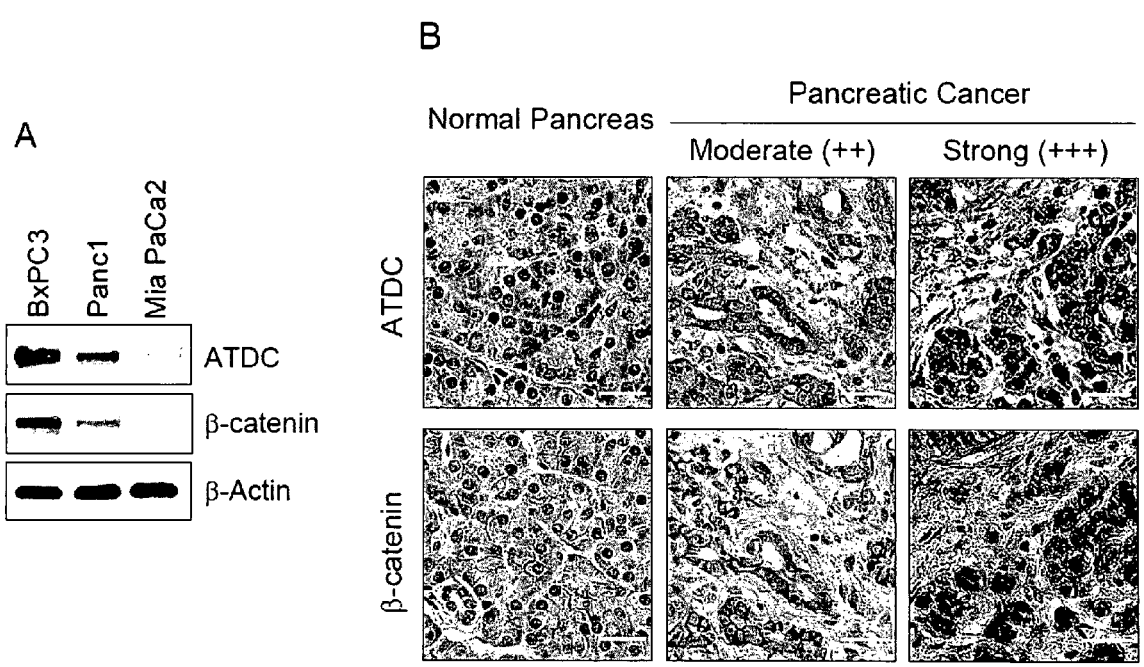
FIG. 24. Correlation between ATDC and β-catenin expression in pancreatic cancer. (A) Western blot analysis of ATDC and β-catenin expression in BxPC-3, Panc-1, and MiaPaCa-2 cells. β-actin served as a loading control. (B) Immunohistochemical (IHC) staining of samples of normal human pancreas (left panels) and human pancreatic adenocarcinomas (middle and right panels). A correlation between ATDC and β-catenin expression in pancreatic adenocarcinoma samples is evident. The scale bar indicates 50 um. IHC scores are: moderate (++, intermediate intensity staining) or strong (+++, intense staining) in pancreatic adenocarcinoma as judged by a blinded, pancreatic pathologist.

Based on the finding that ATDC is highly expressed in human pancreatic cancers and ATDC-mediated cancer cell growth in selected pancreatic cancer cells is dependent on activation of β-catenin signaling, then ATDC expression and β-catenin levels might be predicted to be well-correlated in pancreatic cancer cell lines and primary pancreatic cancers. As shown in FIG. 24A, the level of β-catenin in pancreatic cancer cell lines correlated well with ATDC levels, with the highest levels of β-catenin observed in BxPC3 cells, which have high levels of endogenous ATDC. Intermediate levels of β-catenin and ATDC proteins were found in Panc1 cells, and both β-catenin and ATDC were minimally expressed in MiaPaCa2 cells. To study further the relationship of ATDC and β-catenin expression in pancreatic cancer, immunohistochemical analysis of ATDC and β-catenin in human pancreatic normal and adenocarcinoma tissues was performed. ATDC staining in normal human pancreas was not observed, expression of β-catenin localized to the cell membrane was observed (FIG. 24B, left panels), as has been previously described (Pasca di Magliano et al., 2007). It is commonly thought that both cytoplasmic and nuclear localization of β-catenin is an indicator of active β-catenin signaling in the Wnt pathway (Fodde et al., 2007). To assess the correlation between ATDC expression and β-catenin, a pancreatic cancer tissue microarray (TMA) containing 47 pancreatic carcinoma samples was analyzed. Focal nuclear staining for β-catenin in 5 (11%) tumors was observed and evidence of elevated cytoplasmic levels of β-catenin in 24 (511%) tumors was also observed. These results correlate well with those previously published on β-catenin expression in pancreatic cancer (Pasca di Magliano et al., 2007). A strong correlation between ATDC and β-catenin expression in the 47 pancreatic carcinoma cases was observed, with moderate to high expression of ATDC in the cancer samples that showed elevated cytoplasmic and/or nuclear β-catenin expression.

Representative samples of pancreatic cancers shown in FIG. 24B (middle and right panels) demonstrate the correlation in ATDC and β-catenin expression in cancer samples with moderate and high levels of ATDC. Importantly, no evidence of pancreatic cancers expressing elevated levels of β-catenin without expressing high levels of ATDC was found, suggesting that elevated cytoplasmic and nuclear levels of β-catenin expression may in fact be dependent on the overexpression of ATDC.

ATDC Interacts with Disheveled-2 and Components of the β-Catenin Destruction Complex to Stabilize Beta-Catenin In the absence of Wnt ligands, cytoplasmic levels of β-catenin are regulated by a multi-protein complex, termed the destruction complex and which contains the Axin, APC, and glycogen synthase kinase 3-β (GSK3β). Axin and APC are believed to function in facilitating efficient phosphorylation of β-catenin by GSK3beta at multiple serine and threonine residues in its N-terminus. Phosphorylated β-catenin is then ubiquinated, leading to its rapid proteosomal degradation (Gordon et al., 2006). To determine if ATDC might increase β-catenin levels by stabilizing β-catenin in pancreatic cancer cells, Panc1 cells (with or without ATDC silencing) were incubated with cycloheximide (CHX) (10 μg/ml) to prevent new β-catenin synthesis and β-catenin levels were then measured over time, with the levels reflective of the rate of β-catenin protein degradation. Silencing of ATDC expression significantly increased the β-catenin degradation rate, resulting in a marked reduction in the levels of remaining β-catenin. The effect of ATDC on β-catenin stability was validated by performing a [$^{35}$S]-methionine pulse-chase assay in Panc1 cells with or without ATDC silencing. It was found that β-catenin was rapidly degraded in Panc1 cells where ATDC expression had been silenced by RNAi approaches, compared to control Panc1 cells (FIGS. 25A, 25B), demonstrating that endogenous ATDC increases β-catenin levels by stabilizing β-catenin in pancreatic cancer cells.

Figure 25:
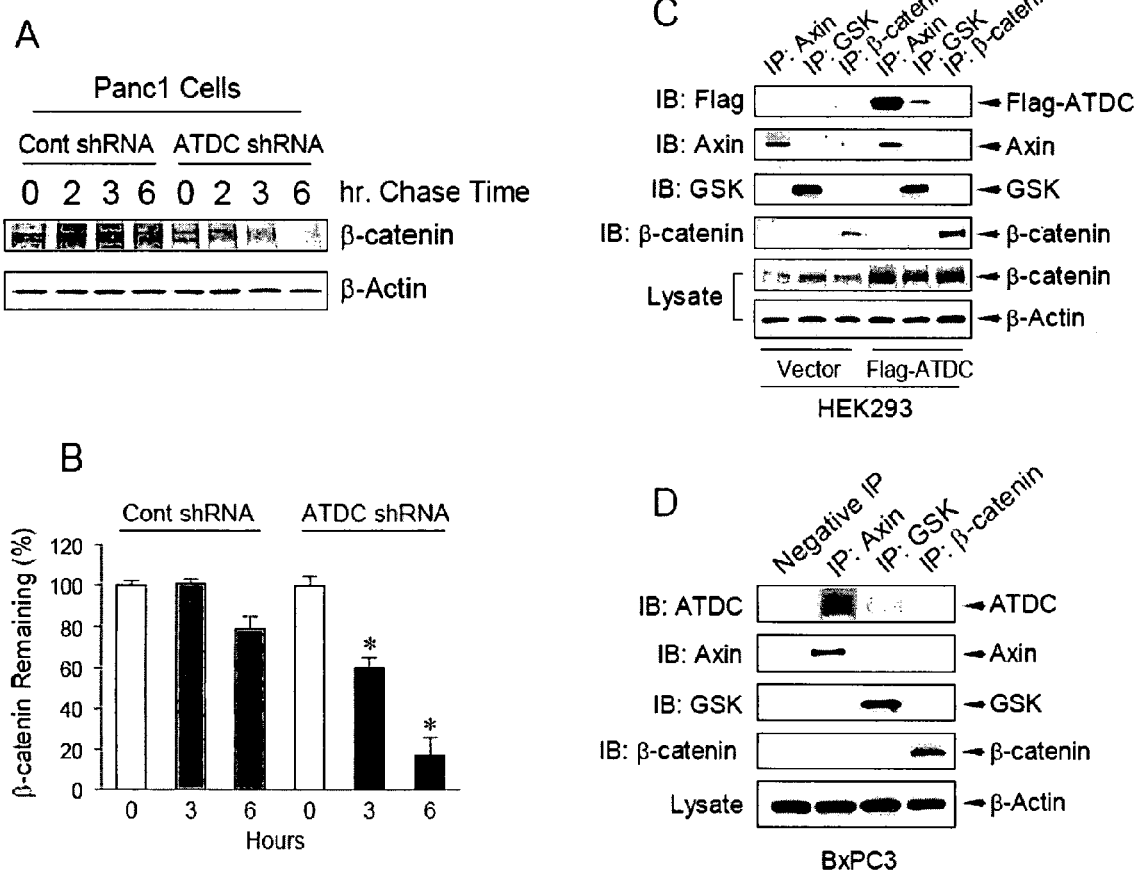
FIG. 25. ATDC stabilizes β-catenin by interacting with disheveled-2 and the β-catenin destruction complex. (A) A pulse-chase assay was used to determine β-catenin stability. Panc1 cells (with or without ATDC silencing) were pulse-labeled with [$^{35}$S]-methionine for 30 min. Pulse-labeled cells were then washed and incubated in chase media for various times. Cell lysates were generated and β-catenin was isolated by immunoprecipitation. Precipitates were analyzed by SDS-PAGE and β-catenin was visualized by autoradiography. (B) β-catenin remaining in (A) was quantitated by densitometry at hours 0, 3 and 6 and normalized relative to the 0 hour time point. Results shown representative of the mean±SE of three independent experiments (n=3 experiments, *p<0.05 vs control shRNA cells at 6 hours). (C) Cell lysates from HEK 293 cells transfected with empty vector or Flag-ATDC were subjected to immunoprecipitation (IP) with Axin, GSK3β or β-catenin antibodies. Immunocomplexes were resolved by SDS-PAGE and subjected to western analysis with anti-Flag antibody. Blotting with an anti-β-actin antibody revealed equal loading. (D) Cell lysates from BxPC3 cells were subjected to immunoprecipitation (IP) with control IgG (negative IP), Axin, GSK3β or β-catenin antibodies. Immunocomplexes were resolved by SDS-PAGE and subjected to western analysis with an ATDC antibody. Blotting with an anti-β-actin antibody revealed equal loading. (E-G) Lysates of HEK 293 cells (E) transfected with empty vector (Vector) or ATDC expression vector (ATDC), and control shRNA- or ATDC shRNA1 or 2-expressing Panc1 (F) and BxPC3 (G) cells were subjected to Western blotting with an anti-Dvl-2 antibody. The upper arrow indicates the phosphorylated form and the lower arrow indicates the non-phosphorylated form of Dvl-2. The experiments were performed twice with similar results. (H) Western blotting of protein isolated from 5 samples of pancreatic adenocarcinoma and 5 samples of normal pancreas. Dvl-1, Dvl-2, Dvl-3 and ATDC expression in pancreatic tissue samples was measured. The experiments were repeated twice with similar results. (1) Cell lysates from HEK 293 cells transfected with empty vector or Flag-ATDC were subjected to immunoprecipitation (IP) with Dvl2 or β-catenin antibodies. Immunocomplexes were resolved by SDS-PAGE and subjected to western analysis with an anti-Flag antibody. Blotting with an anti-β-actin antibody showed equal loading. (J) Cell lysates from BxPC3 cells were subjected to immunoprecipitation (IP) with control IgG (negative IP), Dvl-2 or β-catenin antibodies. Immunocomplexes were resolved by SDS-PAGE and subjected to western analysis with ATDC antibody. Blotting with an anti-β-actin antibody showed equal loading. (K) A pulse-chase assay was used to determine Dvl-2 stability. Panc1 cells (with or without ATDC silencing) were pulse-labeled with [$^{35}$S]-methionine for 30 min. Pulse-labeled cells were then washed and incubated in chase media for various times. Cell lysates were generated and Dvl-2 was isolated by immunoprecipitation. Precipitates were analyzed by SDS-PAGE and Dvl-2 was visualized by autoradiography. (L) Dvl-2 remaining in (K) was quantitated by densitometry at hours 0 and 6 and normalized relative to the 0 hour time point. Results shown are representative of the mean±SE of three independent experiments (n=3 experiments, *p<0.05 vs control shRNA cells at 6 hours).
Figure 25:
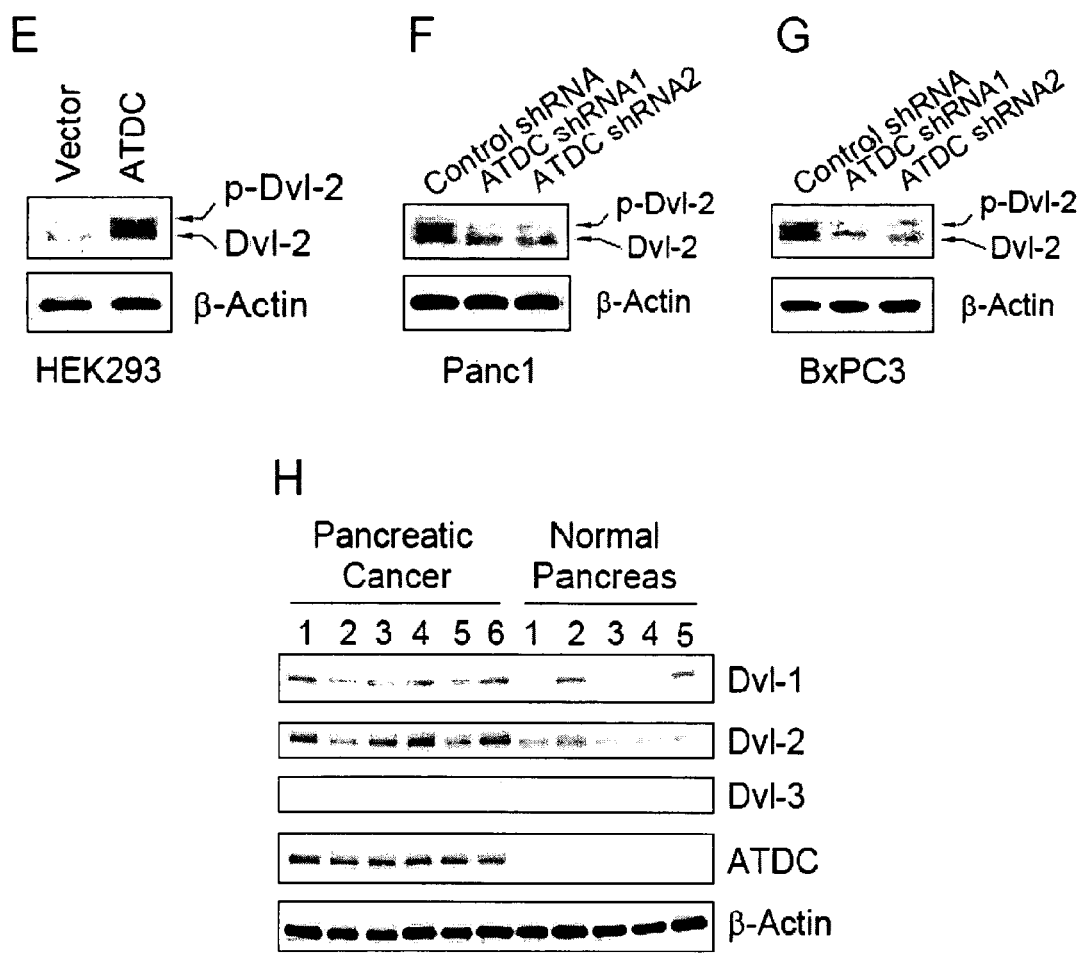
Figure 25:
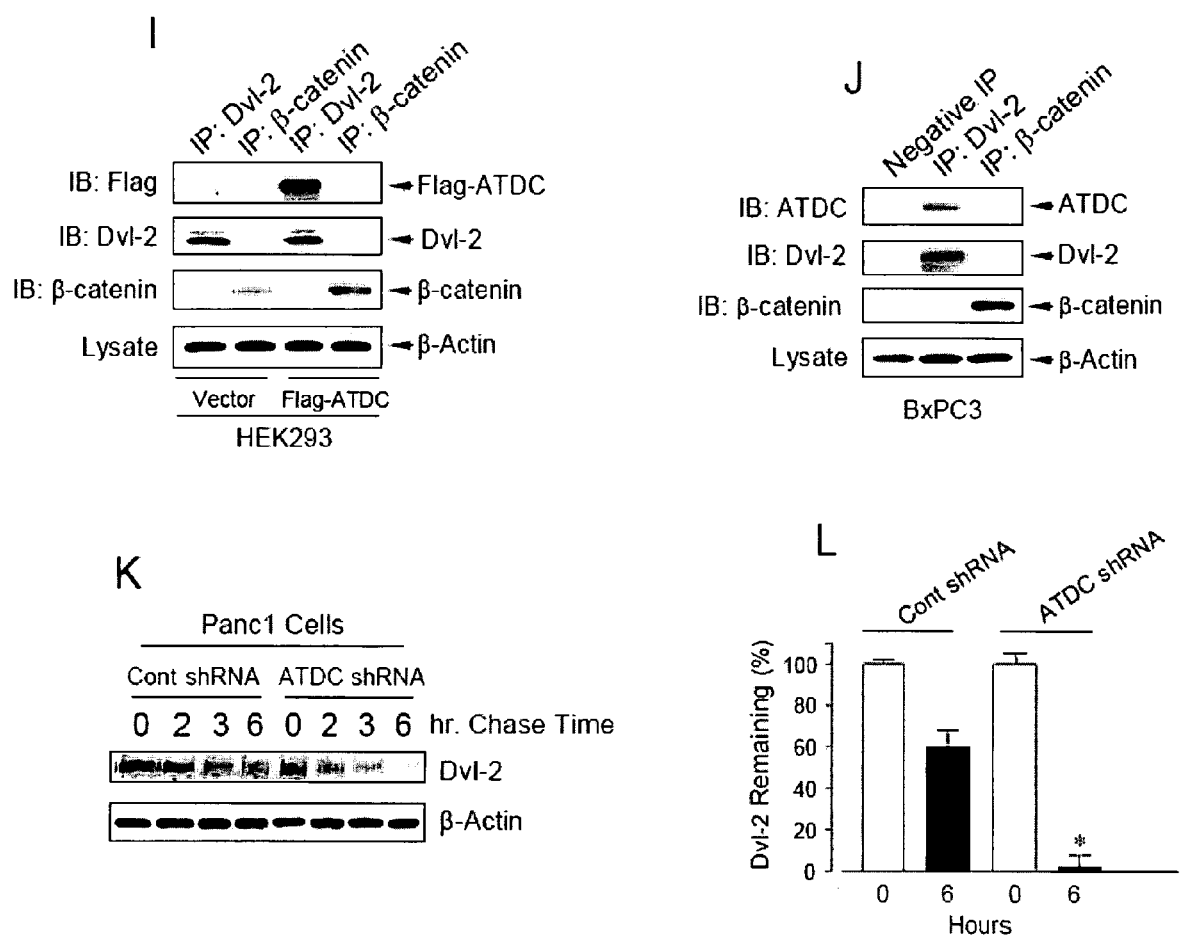

To ascertain the mechanism by which ATDC stabilizes β-catenin, it was first examined whether ATDC interacts with the components of the multi-protein complex that regulates β-catenin stability. In co-immunoprecipitation experiments using antibodies directed to Axin, GSK-3β and β-catenin, evidence of complexes containing ATDC and Axin and complexes containing ATDC and GSK-3β were observed in HEK 293 cells transfected with a Flag-tagged ATDC construct (FIG. 25C). To verify that this interaction was physiologically relevant, the ability of endogenous ATDC in BxPC3 cells to interact with Axin and GSK3β was tested and similar results were obtained (FIG. 25D). ATDC did not interact with β-catenin in either HEK 293 cells over-expressing ATDC or in BxPC3 cells with high endogenous levels of ATDC (FIGS. 25C, 25D). The results are consistent with the possibility that ATDC may interfere with GSK-3β-dependent phosphorylation of β-catenin by the destruction complex.

Based on the findings, it was examined if ATDC might activate disheveled (Dvl), a cytoplasmic protein that is activated by binding of Wnt ligands to the frizzled/LRP coreceptor at the cell surface. Activated Dvl then binds to the Axin/GSK3β complex and antagonizes GSK-3β dependent phosphorylation of β-catenin in a manner not dissimilar to what we observed with ATDC. Indeed, increased Dvl-2 levels (total and phosphorylated forms) in HEK 293 cells overexpressing ATDC were found, as well as in Panc1 and BXPC3 cells which have high endogenous levels of ATDC (FIGS. 25E-G). Furthermore, silencing of endogenous ATDC expression in Panc1 and BxPC3 cells reduced the expression of Dvl-2 (FIGS. 25F, 25G). Conversely, increased levels of Dvl-2 were present in primary pancreatic cancer samples that had elevated expression of ATDC (FIG. 25H). Finally, immunohistochemical analysis revealed co-localization of ATDC and Dvl-2 in pancreatic cancer cells. Co-immunoprecipitation experiments in HEK 293 cells and BxPC3 cells demonstrated that ATDC formed a complex with Dvl-2 (FIGS. 25I, 25J). Complex formation between ATDC and Dvl-1 or Dvl-3 in either ATDC-transfected HEK 293 or BxPC3 cells was not seen. To determine which region of the ATDC molecule interacted with Dvl-2, a series of Flag-tagged ATDC truncation mutants and performed co-immunoprecipitation experiments were created. It was found that the ATDCΔ260 deletion mutant was able to interact with Dvl-2 while the ATDCΔ348 mutant did not interact, suggesting that the ATDC region containing amino acids 260-348, a region which contains a coiled-coil domain, interacted with Dvl-2.

It was then tested whether modulating the levels of ATDC in cells affected the abundance of Dvl-2 transcripts. Dvl-2 gene expression, as measured by semi-quantitative RT-PCR, was not altered in either HEK 293 cells overexpressing ATDC or in Panc1 cells with ATDC knockdown compared to control cells. It was then tested whether ATDC might be altering Dvl-2 levels by affecting protein stability. The [$^{35}$S]-methionine pulse-chase assays in Panc1 cells with or without ATDC knockdown showed that Dvl-2 was rapidly degraded in Panc1 cells with ATDC knockdown compared to control Panc1 cells (6K,6L), suggesting that ATDC forms a complex with Dvl-2 and increases Dvl-2 levels by regulating Dvl-2 post-transcriptionally, perhaps via direct effects on Dvl-2 protein stability.

The Oncogenic Effects of ATDC are Mediated by Dvl-2

Figure 26:
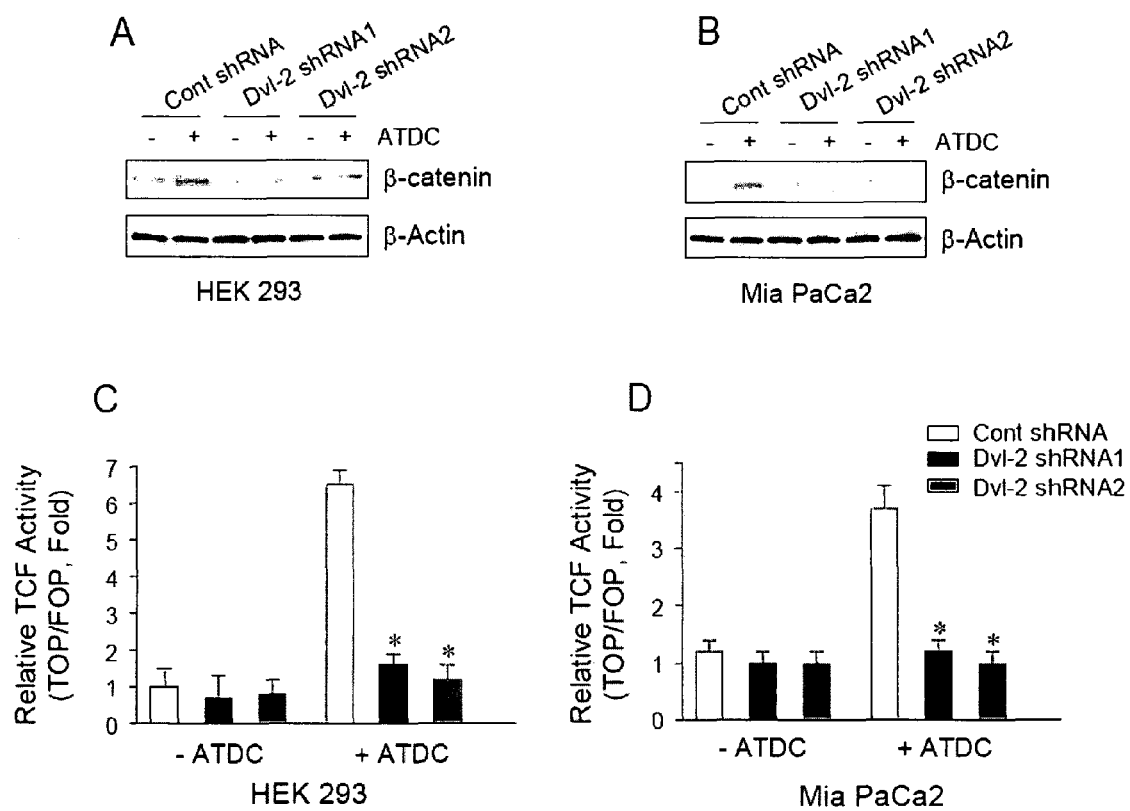
FIG. 26. The oncogenic effects of ATDC are mediated by Dvl-2. (A. B) The effects of Dvl-2 shRNA 1 or 2 on b-catenin expression is shown in representative Western blots of HEK 293 (A) and MiaPaCa2 cells (13) with or without ATDC overexpression. (C, D) TCF reporter activity was assessed in Dvl-2 shRNA 1 or 2-transfected HEK 293 (C) or Mia PaCa2 cells (D) with (+) or without (−) ATDC overexpression. The results from 3 separate experiments, performed in triplicate (*p<0.05 vs empty vector-transfected cells). (E. F) MTS proliferation assays in Dvl-2 shRNA1 or 2-transfected HEK 293 (E) and MiaPaCa2 (F) cells with (+) or without (−) ATDC overexpression (n=3, *p<0.05 vs wild type cells). (G) TCF reporter activity was measured in HEK 293, SW480, DLD-1 and HCT-116 cells with vector (white bars) or ATDC (black bars) transfection using the β-catenin responsive TOPFLASH reporter and the mutant control FOPFLASH reporter. The mean of the TOP/FOP ratio, as compared with the activity, for three independent experiments, performed in triplicate. (H) Cell proliferation of empty vector- and ATDC expression vector-transfected HEK 293, SW480, DLD-1 and HCT-116 cells are shown (n=3, *p<0.05 vs control, non-treated cells). (I) Varying amounts of wild type β-catenin (β-Cat) (1-2 μg) or constitutively active mutant β-catenin (S33Y) (0.2 or 0.5 ug) constructs with TOPFLASH (0.2 ug) or FOPFLASH (0.2 ug) reporter constructs were co-transfected into Panc1 cells with control shRNA or ATDC shRNA expression. 48 hours after transfection, TOPFLASH reporter assays were performed. The experiments were repeated three times and the data is expressed as the mean±SE. (*p<0.05, control shRNA vs ATDC shRNA; p<0.01, Panc1 cells (ATDC shRNA) with β-catenin vs. without β-catenin; and *p<0.001, Panc1 cells (ATDC shRNA) with S33Y vs without S33Y). (J) Varying amounts of wild type-βcatenin (β-Cat) (1-2 μg) or constitutively active mutant β-catenin (S33Y) (0.2 or 0.5 ug) constructs were co-transfected into Panc1 cells with control shRNA or ATDC shRNA expression. 48 hours after transfection, cell growth rates were assessed. The experiments were repeated three times and the data is expressed as the mean±SE. (*p<0.05, control shRNA vs ATDC shRNA; p<0.01, Panc1 cells (ATDC shRNA) with β-catenin vs. without β-catenin; and *p<0.001, Panc1 cells (ATDC shRNA) with S33Y vs without S33Y).
Figure 26:
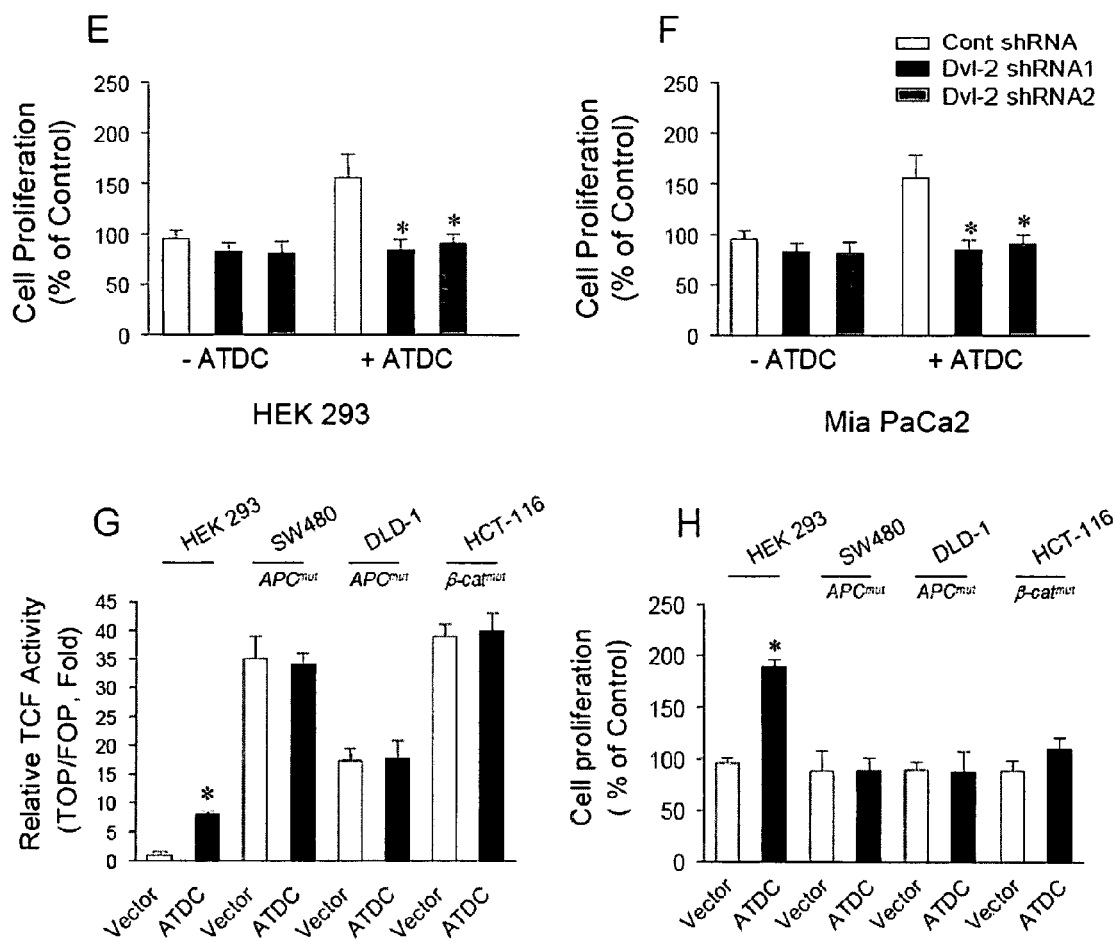
Figure 26:
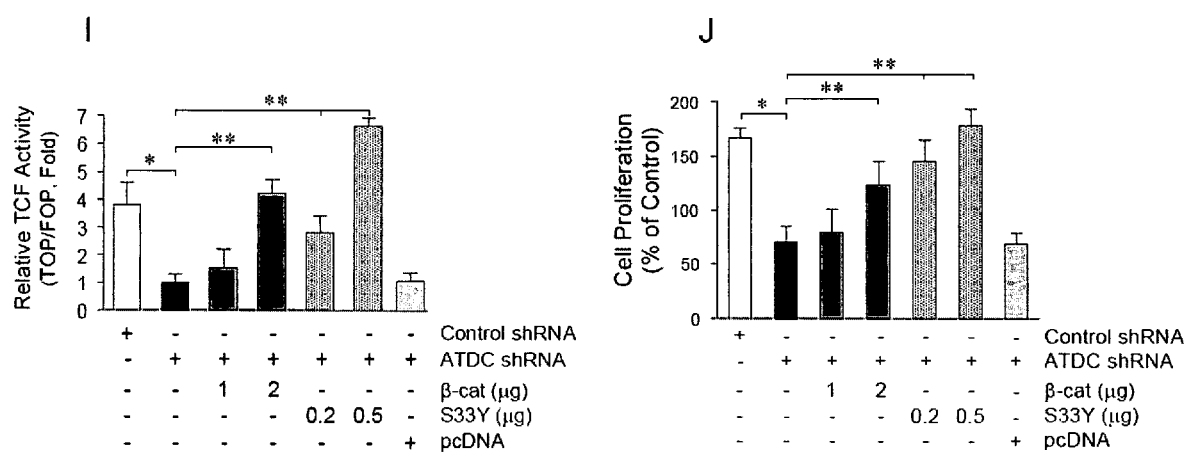

To verify that the ability of ATDC to increase TCF activity and cellular proliferation is mediated through Dvl-2, two Dvl-2 shRNA constructs targeting different regions of Dvl-2 were transfected into HEK 293 and MiaPaCa2 cells in order to examine the effects of Dvl-2 knockdown on ATDC function. Both Dvl-2 shRNA 1 and 2 (FIG. 28) were effective in knocking down levels of Dvl-2 in HEK 293 and MiaPaCa2 cells. Knockdown of Dvl-2 in both HEK 293 and MiaPaCa2 cells overexpressing ATDC was able to inhibit the increases in β-catenin levels (FIGS. 26A, 26B), TCF activity (FIGS. 26C, 26D) and cell proliferation (FIGS. 26E, 26F) induced by ATDC.

If ATDC stabilizes β-catenin levels by acting on upstream signaling events mediated by Dvl-2, then modulating ATDC levels should not influence β-catenin levels in cell lines with either APC or β-catenin mutations. Indeed, over-expression of ATDC in the APC mutant SW480 and DLD-1 cell lines or the β-catenin mutant HCT-116 cell line did not alter TCF activity or cell proliferation as compared to control cells (26G and 26H). These findings also predicted that the decrease in TOPFLASH reporter caused by silencing of ATDC in Panc1 cells would be reversed by increasing the levels of β-catenin to the cells. It was observed that silencing of ATDC in Panc1 cells significantly inhibited the increase in TOPFLASH reporter activity seen in control Panc1 cells and that transfection with wild type or a mutant oncogenic form of β-catenin (S33Y β-catenin) was able to reverse the inhibitory effect of silencing of ATDC on TOPFLASH reporter activity (FIG. 26I) and cell proliferation (FIG. 26J) in a dose-dependent fashion.

Discussion

The above Examples have identified ATDC as a protein highly expressed in the majority of human pancreatic adenocarcinomas and pancreatic cancer precursor lesions and have demonstrated that expression of ATDC in pancreatic cancer cells promoted cellular proliferation and enhanced tumor growth and metastasis. Additionally, these Example provide evidence that elevated levels of ATDC expression correlates with elevated β-catenin levels in pancreatic cancer cell lines and primary pancreatic cancers, and that silencing of ATDC via shRNA approaches antagonized β-catenin/TCF-mediated reporter activation and activation of TCF target genes. β-catenin was implicated in the oncogenic effects of ATDC in vitro and in vivo, and this data indicates that ATDC's ability to increase β-catenin levels appeared to be attributable to ATDC's effects on disheveled-2 protein expression.

ATDC has been reported to be up-regulated in a number of different cancer types, including lung, bladder, colorectal, ovarian and endometrial cancers and multiple myeloma (Dyrskjot et al., 2004; Glebov et al., 2006; Hawthorn et al., 2006; Mutter et al., 2001; Ohmachi et al., 2006; Santin et al., 2004; Zhan et al., 2002). A recent report identified a correlation between ATDC expression in gastric cancer and poor histological grade, large tumor size, extent of tumor invasion, and lymph node metastasis (Kosaka et al., 2007). ATDC has also been reported to be down-regulated in some cancer types (Smith et al., 2005, Nacht et al., 1999; Zhang et al., 2006; Ernst et al., 2002) suggesting the function of ATDC may be depend on cellular context. In none of these reports was the role of ATDC in tumorigenesis determined.

It was found that ATDC upregulated β-catenin levels in pancreatic cancer cell lines and primary pancreatic cancers. A large body of data supports the contribution of activation of the canonical (β-catenin-dependent) Wnt signaling pathway in the development of colorectal cancer. Sustained β-catenin pathway activation independent of APC, Axin1 or β-catenin mutations has been demonstrated in a subset of breast and ovarian cancer (Bafico et al., 2004). Mutations in APC or β-catenin appear to be rare in pancreatic adenocarcinoma (Zeng et al., 2006). While robust activation of the pathway due to signature mutations in components of the β-catenin signaling cascade that are commonly observed in other gastrointestinal cancers are not present in pancreatic adenocarcinoma, immunohistochemical analyses of β-catenin suggest a possible contribution of β-catenin signaling during PanIN progression and the development of invasive pancreatic cancer. Increased levels of both cytoplasmic and nuclear β-catenin, indicative of β-catenin signaling activity, have been reported in a substantial group of pancreatic adenocarcinomas and PanINs (Zeng et al., 2006; Pasca di Magliano et al., 2007). Pasca di Magliano and colleagues reported that 65% of pancreatic cancers have an increase in either cytoplasmic and/or nuclear β-catenin. Similar results were obtained in Pdx-Cre;Kras$^{G12D}$ and Pdx-cre; Kras$^{G12D}$;p53$^{f/+}$ transgenic mice that developed PanIN lesions and subsequent invasive pancreatic cancers that were phenotypically indistinguishable from pancreatic adenocarcinomas seen in human patients. Moreover, the authors showed that cancer cell survival and proliferation, depended, at least in part, on β-catenin signaling activity in multiple human pancreatic cancer cell lines.

The mechanisms by which ATDC levels are upregulated in pancreatic adenocarcinomas remain unclear. However, an understanding of such mechanism is not necessary to practice the present invention. Interestingly, Pasca di Magliano and colleagues demonstrated that increased hedgehog signaling, which is one of the earliest changes in PanIN lesions, activated β-catenin signaling in transgenic mice and untransformed pancreatic duct cells, suggesting that hedgehog may play a role in upregulating β-catenin activity in some pancreatic adenocarcinomas. A possible connection between hedgehog upregulation and ATDC expression in human pancreatic cancer cell lines or primary tumors remains to be explored.

The levels of the free cytoplasmic pool of β-catenin are known to be regulated by Wnt ligands. In the absence of an activating Wnt signal, mediated via Wnt binding to the frizzled-low density lipoprotein-related (LRP) 5/6 co-receptor complex, cytoplasmic β-catenin is destabilized by a multiprotein complex containing axin, GSK3β, and APC. Axin acts as the scaffold of this complex as it directly interacts with all the other components-β catenin, APC, and GSK3β. Interaction of GSK3β with Axin in the complex facilitates efficient phosphorylation of β-catenin by GSK3β. Phosphorylated β-catenin is then ubiquinated, leading to its rapid proteosomal degradation. It was found that ATDC bound to Axin and GSK-3β in pancreatic cancer cells, suggesting that ATDC interacted with the destruction complex to prevent phosphorylation and subsequent ubiquination of β-catenin.

When Wnt binds to the frizzled/LRP co-receptors at the cell surface, a cytoplasmic protein, Dvl, antagonizes GSK-3β dependent phosphorylation of β-catenin. Although it is not known if Dvl binds directly to the frizzled/LRP co-receptor or whether intermediary proteins are involved in the signal transduction between frizzled and Dvl, Dvl appears to bind to axin and inhibit GSK-3β-dependent phosphorylation of β-catenin, APC and axin. Once the phosphorylation of β-catenin is reduced, beta-catenin dissociates from the axin complex, resulting in its accumulation in the cytoplasm. Once stabilized, a fraction of the β-catenin is translocated to the nucleus, where it binds to transcription factors such as the TCF/lymphoid enhancer binding factor and thereby stimulates the transcription of β-catenin target genes. The above Example shows that ATDC expression in HEK 293 cells induced expression of Dvl-2, and demonstrated that ATDC formed a complex with Dvl-2 in pancreatic cancer cells. It was demonstrated that levels of ATDC in a set of primary pancreatic cancer correlated well with Dvl-2 levels, suggesting that ATDC upregulates Dvl-2 levels in primary pancreatic cancers, and increases β-catenin levels by this mechanism. This Example further showed that knockdown of Dvl-2 in ATDC expressing cells abrogates that enhanced TCF activity and cell proliferation induced by ATDC, directly implicating Dvl-2 as an intermediary in this process.

The regulation of the disheveled protein is still poorly understood, but recent data suggest that disheveled, like β-catenin, may be controlled by ubiquination and degradation by the proteosome (Hershko et al., 1998; Simons et al., 2005; Miyazaki et al., 2004). Dvl-1 has been reported to interact with the neuronal Homologous to E6AP carboxyl terminus (HECT)-type ubiquitin ligase NEDL1 (Miyazaki et al., 2004). The proteins inversin and the interactions between PP2A phosphatase and the Wnt-induced antagonist naked cuticle have been shown to modulate the stability of Dvl-1 (Simons et al., 2005; Creyghton et al., 2005). And, in a recent manuscript published by Angers and colleagues, it was shown that the KLHL12-Cullin-3 ubiquitin ligase negatively regulates the Wnt-β-catenin pathway by targeting disheveled for degradation (Angers et al., 2006). This Example found that ATDC did not increase Dvl-2 levels by changes in Dvl-2 gene expression but rather by enhancing the stability of the Dvl-2 protein, supporting changes in Dvl stability serve as a important common mechanism in regulating the Wnt/β-catenin signaling pathway.

Figure 27:
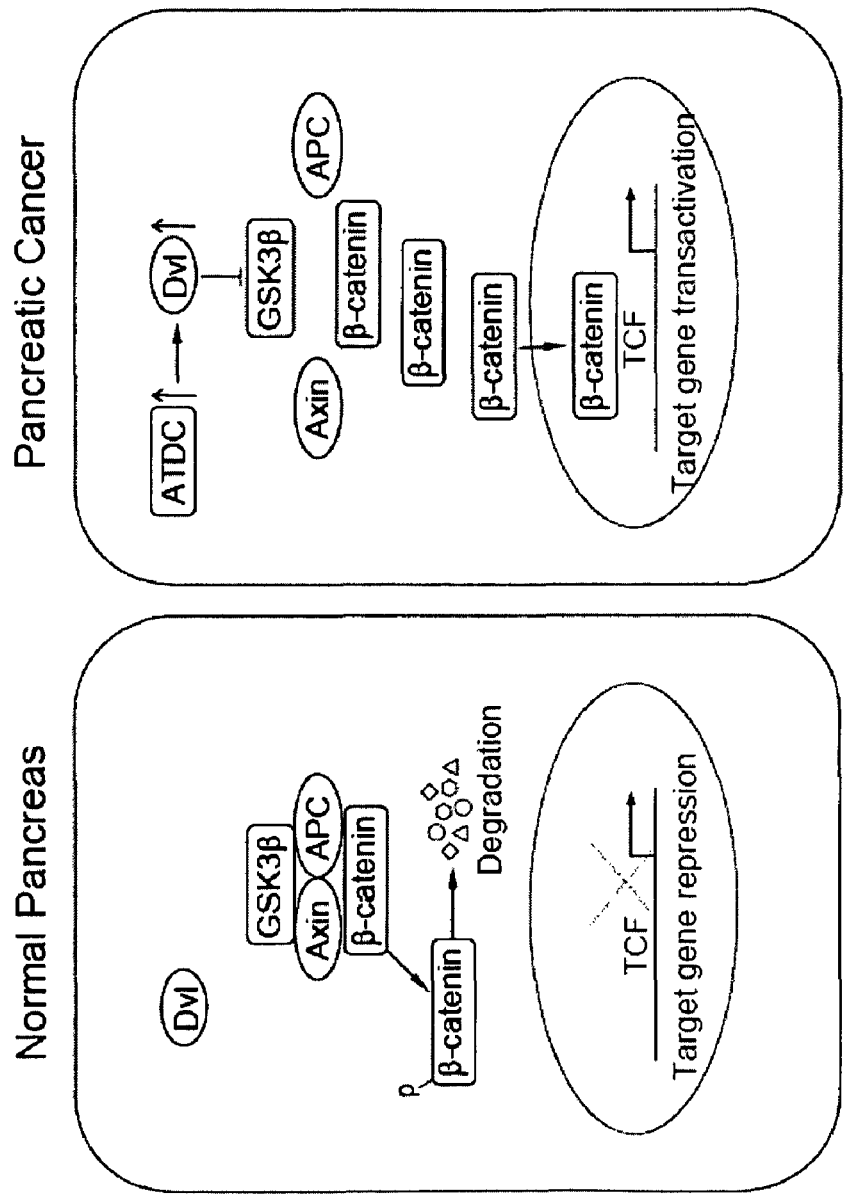
FIG. 27. Model of how ATDC mediates activation of β-catenin signaling in pancreatic cancer cells. (Left panel). In unstimulated normal pancreatic cells lacking ATDC, disheveled-2 (Dvl-2) is in the cytoplasm and is not bound to the Axin/GSK-3β/APC destruction complex. This allows the destruction complex to phosphorylate β-catenin and target it for ubiquitin-mediated degradation. (Right panel). In pancreatic cancer cells expressing high levels of ATDC, ATDC binds to an stabilizes Dvl-2, bringing it to the β-catenin destruction complex. Binding of the ATDC and Dvl-2 to the destruction complex inhibits destruction complex function, resulting in the release of β-catenin from the destruction complex, leading to increased β-catenin levels and subsequent activation of downstream target genes.

While the present invention is not limited to any mechanism and an understanding of the mechanism is not necessary in order to practice the present invention, the data in the present Examples support a model for the mechanism by which ATDC functions to promote the oncogenesis of pancreatic cancer cells as shown in FIG. 27. For example, in this hypothetical model, in unstimulated, normal pancreatic cells lacking ATDC, disheveled-2 (Dvl-2) is in the cytoplasm and is not bound to the Axin/Gsk-3β/APC destruction complex. This allows the destruction complex to phosphorylate β-catenin and target it for ubiquitin-mediated degradation. In pancreatic cancer cells expressing high levels of ATDC, ATDC binds to and stabilizes Dvl-2, resulting in the release of β-catenin catenin from the destruction complex, increased β-catenin levels and subsequent activation of downstream β-catenin/TCF-regulated target genes.

Example XI miRNAs that Regulate ATDC

This example relates to MicroRNAs that inhibit the expression of ATDC (e.g., in pancreatic cancer cells). MicroRNAs are regulatory, non-protein-coding, endogenous RNAs that have recently gained considerable attention in the scientific community. They are 18-24 nucleotides in length and are thought to regulate gene expression through translational repression by binding to a target mRNA (see, e.g., Lim et al., Science 2003; 299 (5612):1540; Chen et al., Semin Immunol 2005; 17 (2):155-65; Sevignani et al., Mamm Genome 2006; 17 (3):189-202). They are also proposed to regulate gene expression by mRNA cleavage, and mRNA decay initiated by miRNA-guided rapid deadenylation (Wu et al., Proc Natl Acad Sci USA 2006; 103 (11):4034-9). miRNAs are abundant, highly conserved molecules and predicted to regulate a large number of transcripts. To date the international miRNA Registry database has more than 900 human identified microRNAs (Release 12.0: September 2008, "http://" followed by "microrna.sanger.ac.uk/sequences/") and their total number in humans has been predicted to be as high as 1,000 (Berezikov et al., Cell 2005; 120 (1):21-4). Many of these microRNAs exhibit tissue-specific expression (Sood et al., Proc Natl Acad Sci USA 2006; 103 (8):2746-51) and many are defined to be either tumor suppressors or oncogenes (Lee et al., Curr Opin Investig Drugs 2006; 7 (6):560-4; Zhang et al., Dev Biol 2006; Calin et al., Nat Rev Cancer 2006; 6 (11):857-66) and play a crucial role in variety of cellular processes such as cell cycle control, apoptosis, and haematopoiesis. Dysregulation of several miRNAs are thought to play a significant role in human disease processes including tumorigenesis (Hwang et al., Br J Cancer 2006; 94 (6):776-80; Thomson et al., Genes Dev 2006; 20 (16):2202-7).

A search for potential miRNAs that regulate ATDC gene expression via 3'-UTR region has been performed (See FIG. 30; SEQ ID NO:14), from miRNA databases (Release 12.0: September 2008, "http://" followed by "microrna.sanger.ac.uk/sequences/"), and screened a list of identified miRNAs from the search. The sequences of the identified miRNAs are listed in Table 1.

TABLE 1

| Name of miRNA (bottom) and position on target region (top) | predicted consequential pairing of target region (top) and miRNA (bottom) | seed match |
|---|---|---|
| Position 1111-1117 of TRIM29 3' UTR (SEQ ID: 15) | 5' . . . CUUUCCCUUUGGAA---UAAACCAU . . . | 7mer-1A |
| hsa-miR-299-5p (SEQ ID NO: 16) | 3'         UACAUACACCCUGCCAUUUGGU |  |
| Position 401-408 of TRIM29 3' UTR (SEQ ID NO: 17) | 5' . . . AGGCCUAUAGACGUU---UCUCUCCA . . . | 8mer |
| hsa-miR-185 (SEQ ID NO: 18) | 3'              CUUGACGGAAAGAGAGGU |  |
| Position 781-788 of TRIM29 3' UTR (SEQ ID NO: 19) | 5' . . . GCUACUGGCCCAGCUACCAUUUA . . . | 8mer |
| hsa-miR-522 (SEQ ID NO: 20) | 3'           UUGUGAGAUUUCCCUUGGUAAAA |  |
| Position 870-877 of TRIM29 3' UTR (SEQ ID NO: 21) | 5' . . . GGCUGACCGCAAAAG-GUGCCUUA . . . | 8mer |
| hsa-miR-506 (SEQ ID NO: 22) | 3'              AGAUGAGUCUUCCCACGGAAU |  |
| Position 880-886 of TRIM29 3' UTR (SEQ ID NO: 23) | 5' . . . AAAAGGUGCCUUACACACUGCCC . . . | 7mer-m8 |
| hsa-miR-34c (SEQ ID NO: 24) | 3'            CGUUAGUCGAUUGAUGUGACGGA |  |
| Position 920-926 of TRIM29 3' UTR (SEQ ID NO: 25) | 5' . . . CCCAUCAGAGGCUGCCUCCUCCU . . . | 7mer-m8 |
| hsa-miR-765 (SEQ ID NO: 26) | 3'              GUAGUGGAAGGAAGAGGAGGU |  |

TABLE 1-continued

| | | | |
|---|---|---|---|
| Position 299-305 of TRIM29 3' UTR (SEQ ID NO: 27) | 5' | . . . CCCUAACCCGCCAGCCUCCUCCU . . . | 7mer-m8 |
| | | ```         |||  |||||||``` | |
| hsa-miR-765 (SEQ ID NO: 28) | 3' | GUAGUGGAAGGAA-GAGGAGGU | |
| Position 962-968 of TRIM29 3' UTR (SEQ ID NO: 29) | 5' | . . . GCAUAUCAGGGUGCUCAAGGAUU . . . | 7mer-m8 |
| | | ```         |||  |||||||``` | |
| hsa-miR-362 (SEQ ID NO: 30) | 3' | UGAGUGUGGAUCCAAG--GUUCCUAA | |
| Position 968-974 of TRIM29 3' UTR (SEQ ID NO: 31) | 5' | . . . CAGGGUGCUCAAGGAUUGGAGAG . . . | 7mer-m8 |
| | | ```       |||||  |||||||``` | |
| hsa-miR-515-5p (SEQ ID NO: 32) | 3' | GUCUUUCACGAAAGAA-AACCUCUU | |
| Position 1025-1031 of TRIM29 3' UTR (SEQ ID: 33) | 5' | . . . UCCCGUCUCAACAGC--CCCAGGCC . . . | 7mer-m8 |
| | | ```         |||  |||||||``` | |
| hsa-miR-661 (SEQ ID NO: 34) | 3' | UGCGCGUCCGGUCUCUGGGUCCGU | |
| Position 1041-1048 of TRIM29 3' UTR (SEQ ID: 35) | 5' | . . . CCAGGCCUAUGGGGG-CUCUGGAA . . . | 8mer |
| | | ```        ||   |||||||``` | |
| hsa-miR-525 (SEQ ID NO: 36) | 3' | UCUUUCACGUAGGGAGACCUC | |
| Position 880-886 of TRIM29 3' UTR (SEQ ID NO: 37) | 5' | . . . AAAAGGUGCCUUACACACUGCCC . . . | 7mer-m8 |
| | | ```         ||   |||||||``` | |
| hsa-miR-34a (SEQ ID NO: 38) | 3' | UUGUUGGUCGAUUCUGUGACGGU | |
| Position 917-923 of TRIM29 3' UTR (SEQ ID: 39) | 5' | . . . UGCCCCAUCAGAGGC-UGCCUCCU . . . | 7mer-m8 |
| | | ```        ||||  |||||||``` | |
| hsa-miR-650 (SEQ ID NO: 40) | 3' | CAGGACUCUCGCGACGGAGGA | |
| Position 952- of TRIM29 3' UTR (SEQ ID NO: 41) | 5' | . . . GUGACC..AU--GUUCCAACC-CUCU 5' | |
| | | ```        ||  |:  |||||  ||||  |||:``` | |
| hsa-miR-150 (SEQ ID NO: 42) | 3' | UCAGGG..UGCUCAAGGAUUGGAGAGG 3' | |
| hsa-miR-296-5p (SEQ ID NO: 43) | 5' | AGGGCCCCCCCUCAAUCCUGU | |
| hsa-miR-296-3p (SEQ ID NO: 44) | 5' | GAGGGUUGGGUGGAGGCUCUCC | |

Figure 31:
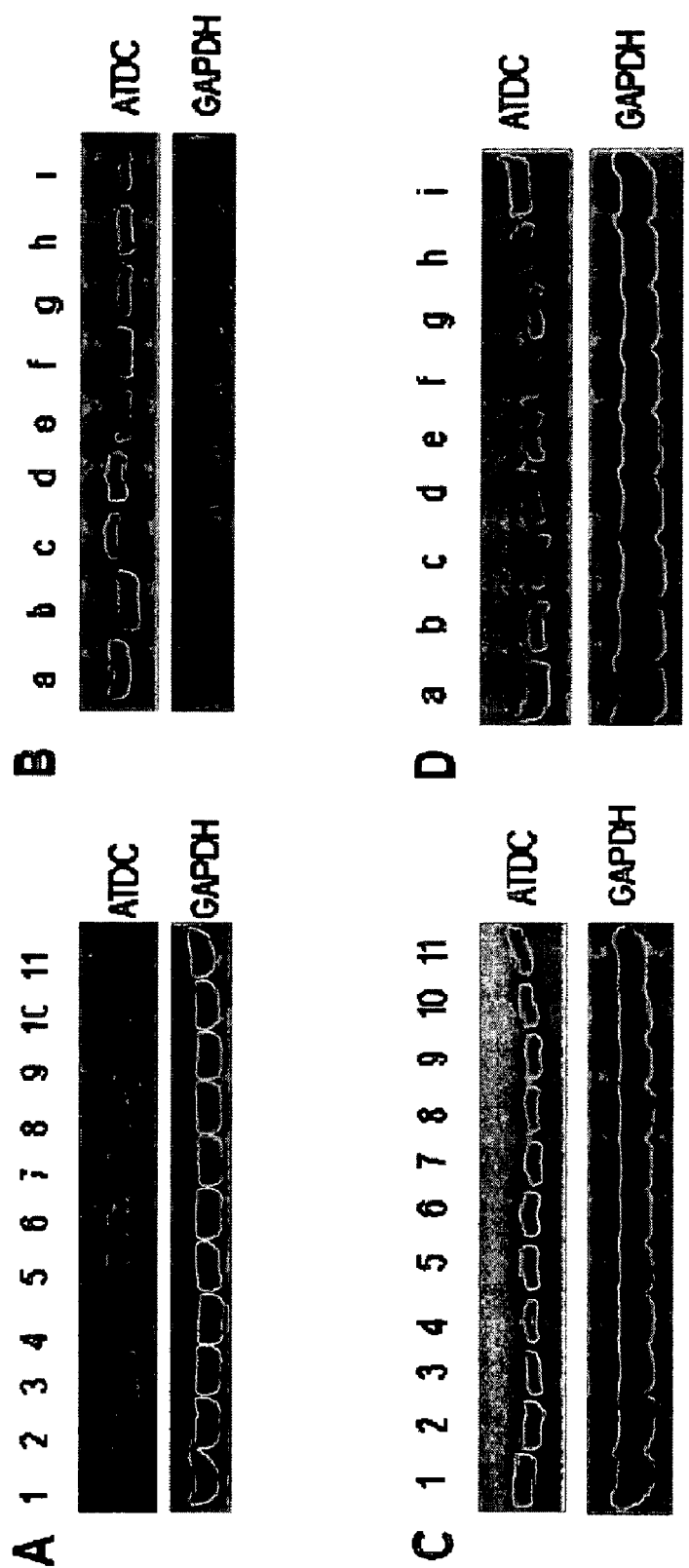
FIG. 31 shows a Western blot analysis of ATDC in L3.6PL and BXPC3 cells 36 h after transfection with different miRNA mimics.

For testing the miRNAs for ATDC, Western blot analysis of pancreatic cancer cells transfected was carried out with the miRNAs by Lipofactamine2000. As shown in FIG. 31, several tested miRNAs potently reduced ATDC protein levels in both pancreatic cancer BXPC-3 cells and L3.6PL cells. They are miR-34a, miR-34c, miR-296, miR-650, miR-299-5p, miR-185, miR-765, miR-522, and miR-362. Interestingly, the miRNA-mediated inhibition of ATDC may be cell context dependent, as miR-500 and miR-525 downregulated ATDC in L3.6PL cells but were less potent in BXPC3 cells, vise versa for miR-650 and miR-765. Although miRBase predicted miR-515-5p targets ATDC, actual assay showed it had no obvious effect on ATDC, demonstrating that empirical testing of individual miRNA is generally required to find miRNAs that regulate ATDC.

Figure 32:
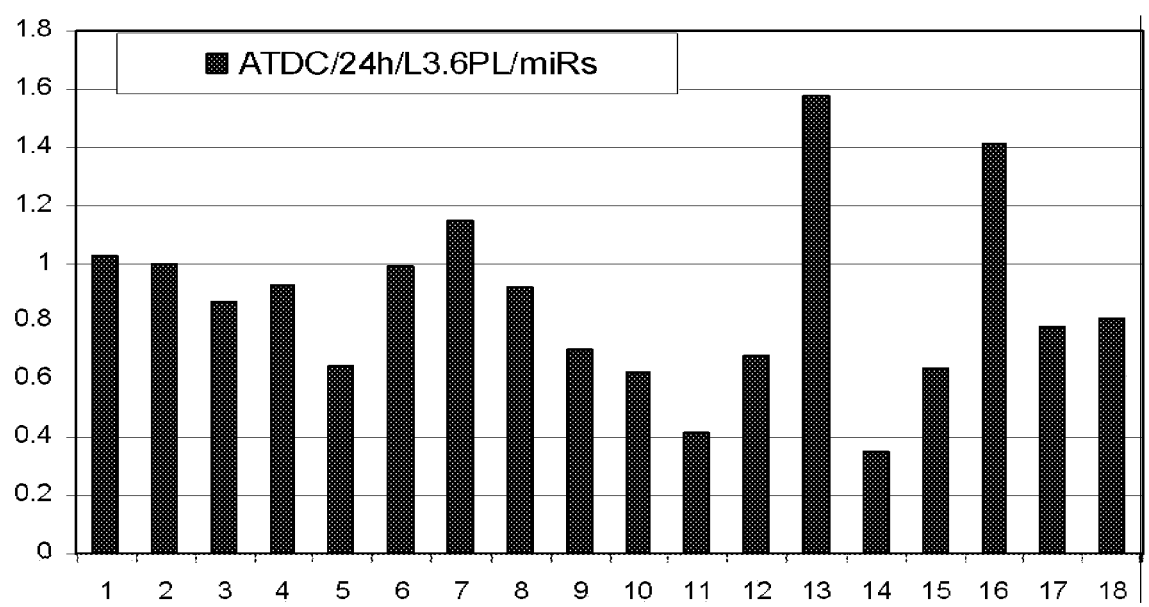
FIG. 32 shows qRT-PCR analysis of ATDC gene expression 24 h after transfection with different miRNA mimics in L3.6PL cells. The lanes in this figure are as follows: 1. Lipofectamine-2000 only; 2. control miRNA; 3. miR-34a; 4. miR-34b; 5. miR-34c; 6. miR-150; 7. miR-296; 8. miR-500; 9. miR-650; 10. miR-299-5p; 11. miR-185; 12. miR-522; 13. miR-506; 14. miR-765; 15. miR-362; 16. miR-515-5p; 17. miR-661; and 18. miR-525.
Figure 33:
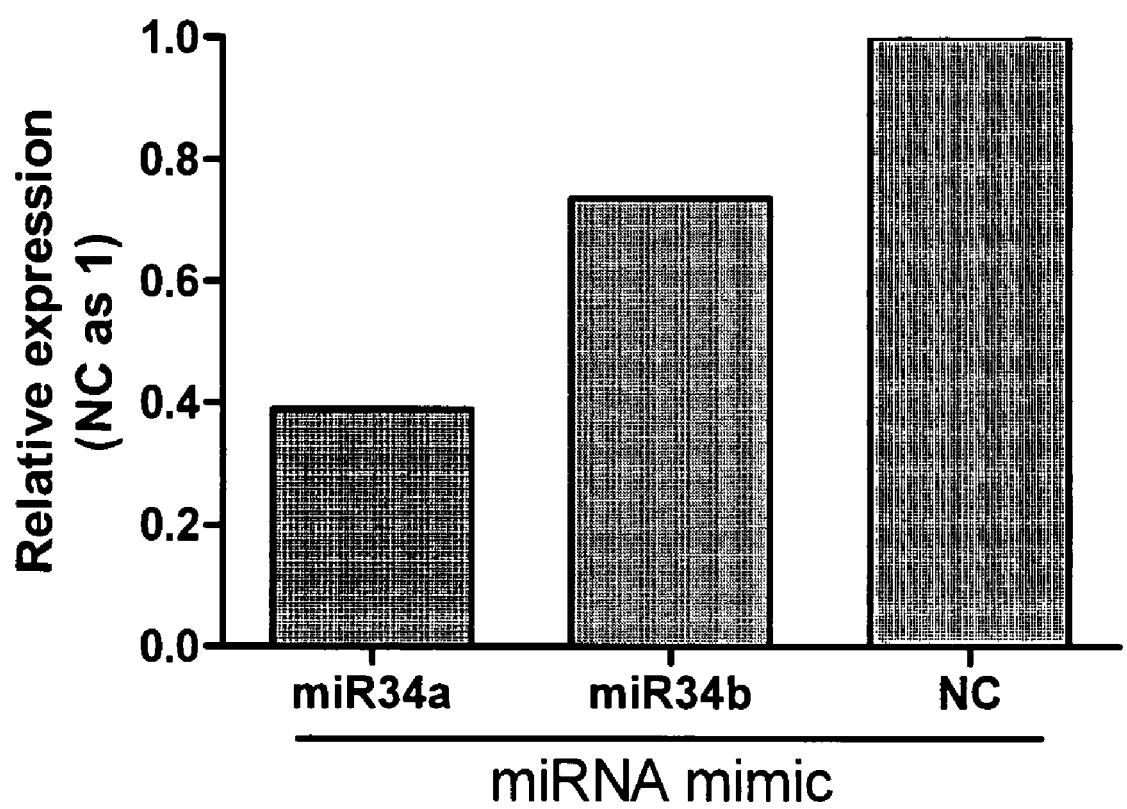
FIG. 33 shows that miR-34a significantly inhibited ATDC gene expression in human gastric cancer KATO III cells.
Figure 34:
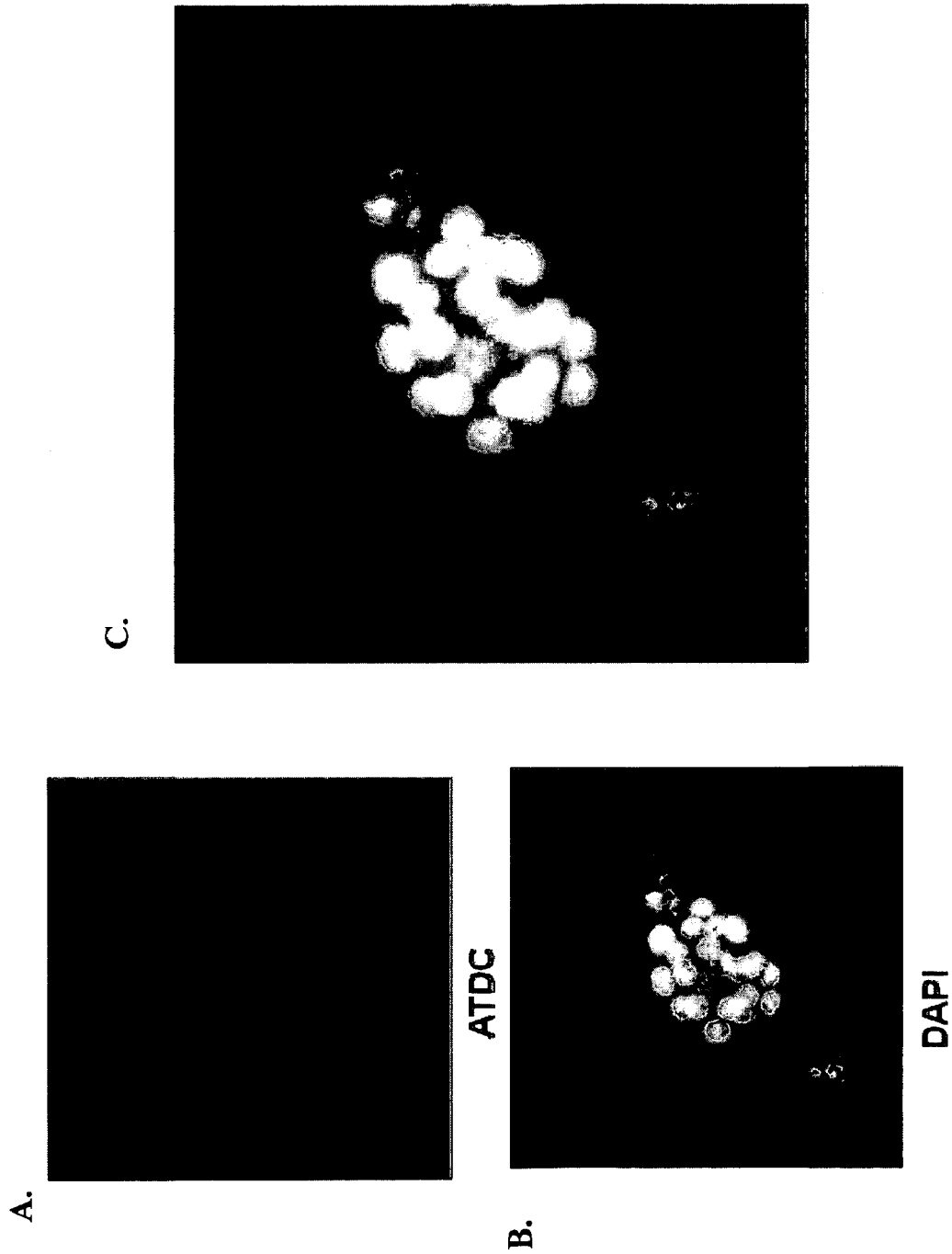
FIG. 34 shows staining of a cancer stem cell tumorsphere with ATDC specific stain (34A), DAPI stain (34B), and the combination in 34C, which shows that cancer stem cells express ATDC.
Figure 35:
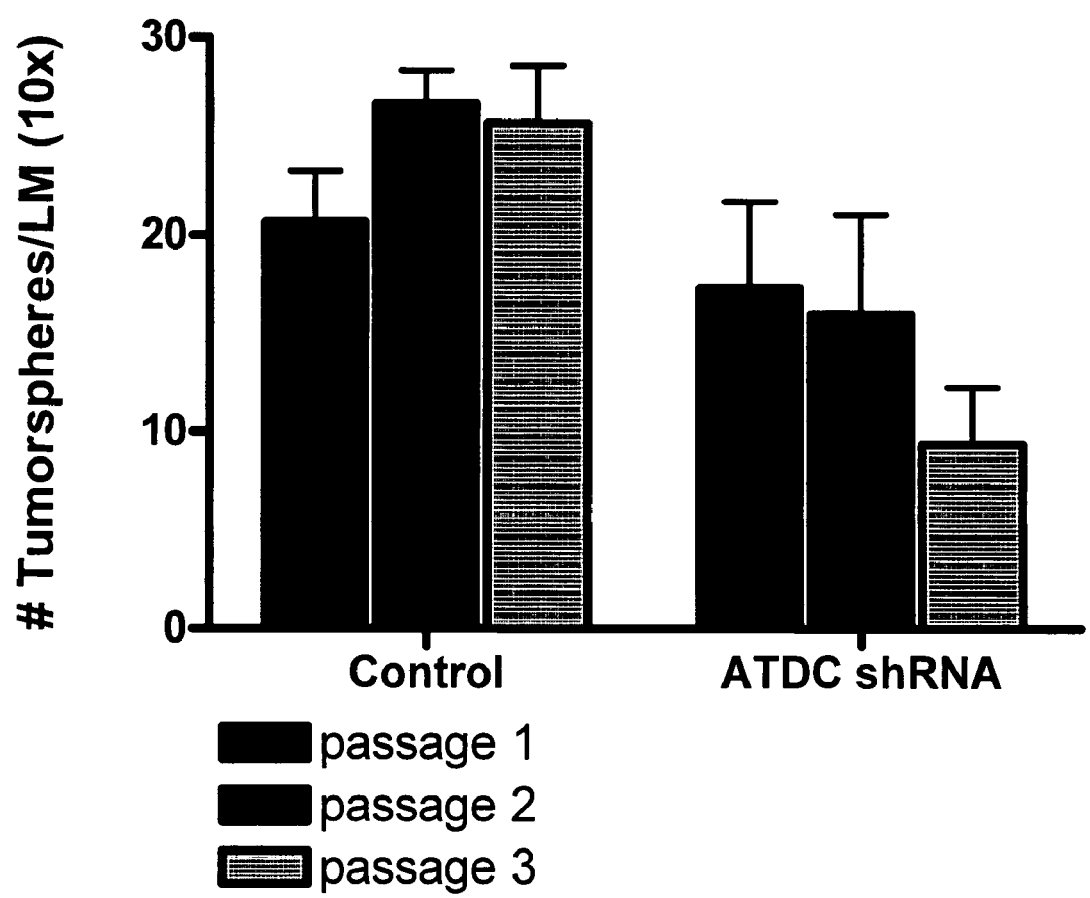
FIG. 35 shows that ATDC shRNA is able to reduce cancer stem cell tumorsphere formation, thereby indicating that targeting ATDC can kill and inhibit cancer stem cells.
Figure 36:
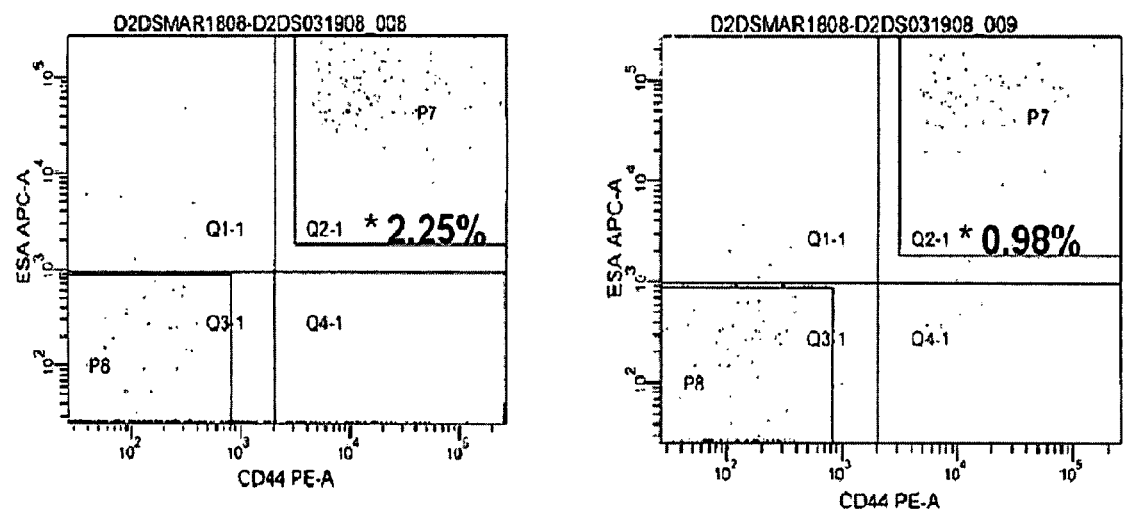
FIG. 36 shows the results of flow cytometry after cancer stem cells have been treated with ATDC silencing agents. These results indicate that targeting ATDC can kill and inhibit cancer stem cells.

Next, the miRNAs regulation of ATDC by qRT-PCR was examined. 24 hours after miRNA mimic transfection of the cancer cells (100 pmol per well in 6-well plates), ATDC mRNA levels were measured by qRT-PCR with TaqMan SYBR Green PCR System (Applied Biosystems). Briefly, total RNA was extracted from the transfected cells using TRIZOL (Invitrogen) according to the manufacturer's instructions. Reverse transcription was performed using a TaqMan Reverse Transcription Kit (Applied Biosystems). For qRT-PCR, 1 μl of gene primers with SYBR Green (Applied Biosystems) in 20 μl of reaction volume was applied. Primers for ATDC: Forward: 5'-CAAGGACGACCTGCT-CAATGT-3' (SEQ ID NO:45), Reverse: 5'-CGATGGTCAC-CACCGTTCTC-3' (SEQ ID NO:46). The qRT-PCR results shown in FIG. 32 are mostly consistent with Western data in FIG. 31, except that miR-506 moderately reduced ATDC protein but it increased ATDC mRNA level. miR-34 was also tested in human gastric cancer KATO III cells. miR-34a potently down-regulated ATDC (FIG. 33).

The miRNAs network provides another layer of epigenetic regulation of ATDC. miR-34a has been shown to be a p53 target and a tumor suppressor, and involved in cancer stem cells regulation. p53 loss of function leads to loss of miR-34, which may be involved in upregulation of ATDC during tumorigenesis and tumor progression. Restoration of those miRNA such as miR-34a will downregulate ATDC, thus overcoming the ATDC-induced tumor promotion and drug resistance. As such, miRNAs, such as miR-34a, may be used for cancer therapy targeting ATDC.

REFERENCES

Angers S, Thorpe C J, Biechele T L, Goldenberg S J, Zheng N, MacCoss M J, Moon R T. (2006). The KLHL12-Cullin-3 ubiquitin ligase negatively regulates the Wnt-β-catenin pathway by targeting disheveled for degradation. Nature Cell Biol 8, 348-357.

Arumugam T, Simeone D M, Van Golen K, Logsdon C D. (2005). S100P promotes pancreatic cancer growth, survival, and invasion. Clin Cancer Res 11, 5356-5364.

Bafico, A., Liu, G., Goldin, L., Harris, V., and Aaronson, S. A. (2004). An autocrine mechanism for constitutive Wnt pathway activation in human cancer cells. Cancer Cell 6, 497-506.

Caca, K., Kolligs, F. T., Ji, X., Hayes, M., Qian, J., Yahanda, A., Rimm, D. L., Costa, J., and Fearon, E. R. (1999). Beta- and gamma-catenin mutations, but not E-cadherin inactivation, underlie T-cell factor/lymphoid enhancer factor transcriptional deregulation in gastric and pancreatic cancer. Cell Growth Differ 10, 369-376.

Cao, D., Hustinx, S. R., Sui, G., Bala, P., Sato, N., Martin, S., Maitra, A., Murphy, K. M., Cameron, J. L., Yeo, C. J., et al. (2004). Identification of novel highly expressed genes in pancreatic ductal adenocarcinomas through a bioinformatics analysis of expressed sequence tags. Cancer Biol Ther 3, 1081-1089; discussion 1090-1081.

Chen, R., Yi, E. C., Donohoe, S., Pan, S., Eng, J., Cooke, K., Crispin, D. A., Lane, Z., Goodlett, D. R., Bronner, M. P., et al. (2005). Pancreatic cancer proteome: the proteins that underlie invasion, metastasis, and immunologic escape. Gastroenterology 129, 1187-1197.

Clevers H. (2006). Wnt/beta-catenin signaling in development and disease. Cell 127, 469-480.

Creyghton M P, et al. (2005). PR72, a novel regulator of Wnt signaling required for Naked cuticle function. Genes Dev 19, 376-386.

Crnogorac-Jurcevic, T., Missiaglia, E., Blaveri, E., Gangeswaran, R., Jones, M., Terris, B., Costello, E., Neoptolemos, J. P., and Lemoine, N. R. (2003). Molecular alterations in pancreatic carcinoma: expression profiling shows that dysregulated expression of S100 genes is highly prevalent. J Pathol 201, 63-74.

Dyrskjot, L., Kruhoffer, M., Thykjaer, T., Marcussen, N., Jensen, J. L., Moller, K., and Orntoft, T. F. (2004). Gene expression in the urinary bladder: a common carcinoma in situ gene expression signature exists disregarding histopathological classification. Cancer Res 64, 4040-4048.

Ernst, T., Hergenhahn, M., Kenzelmann, M., Cohen, C. D., Bonrouhi, M., Weninger, A., Klaren, R., Grone, E. F., Wiesel, M., Gudemann, C., et al. (2002). Decrease and gain of gene expression are equally discriminatory markers for prostate carcinoma: a gene expression analysis on total and microdissected prostate tissue. Am J Pathol 160, 2169-2180.

Fodde, R., and Brabletz, T. (2007). Wnt/beta-catenin signaling in cancer sternness and malignant behavior. Curr Opin Cell Biol 19, 150-158.

Glebov, O. K., Rodriguez, L. M., Soballe, P., DeNobile, J., Cliatt, J., Nakahara, K., and Kirsch, I. R. (2006). Gene expression patterns distinguish colonoscopically isolated human aberrant crypt foci from normal colonic mucosa. Cancer Epidemiol Biomarkers Prev 15, 2253-2262.

Goddard, A. D., Borrow, J., Freemont, P. S., and Solomon, E. (1991). Characterization of a zinc finger gene disrupted by the t(15; 17) in acute promyelocytic leukemia. Science 254, 1371-1374.

Gordon M D and Nusse R. (2006). Wnt signaling: multiple pathways, multiple receptors, and multiple transcription factors. J Biol Chem 281, 22429-22433.

Gregorieff, A., and Clevers, H. (2005). Wnt signaling in the intestinal epithelium: from endoderm to cancer. Genes Dev 19, 877-890.

Hawthorn, L., Stein, L., Panzarella, J., Loewen, G. M., and Baumann, H. (2006). Characterization of cell-type specific profiles in tissues and isolated cells from squamous cell carcinomas of the lung. Lung Cancer 53, 129-142.

Hershko A and Ciechanover A. The ubiquitin system. (1998). Annu Rev Biochem 67, 425-479.

Hosoi, Y., and Kapp, L. N. (1994). Expression of a candidate ataxia-telangiectasia group D gene in cultured fibroblast cell lines and human tissues. Int J Radiat Biol 66, S71-76.

Hruban, R. H., Goggins, M., Parsons, J., and Kern, S. E. (2000). Progression model for pancreatic cancer. Clin Cancer Res 6, 2969-2972.

Jemal, A., Siegel, R., Ward, E., Murray, T., Xu, J., and Thun, M. J. (2007). Cancer statistics, 2007. C A Cancer J Clin 57, 43-66.

Kapp, L. N., Painter, R. B., Yu, L. C., van Loon, N., Richard, C. W., 3rd, James, M. R., Cox, D. R., and Murnane, J. P. (1992). Cloning of a candidate gene for ataxia-telangiectasia group D. Am J Hum Genet. 51, 45-54.

Kosaka, Y., Inoue, H., Ohmachi, T., Yokoe, T., Matsumoto, T., Mimori, K., Tanaka, F., Watanabe, M., and Mori, M. (2007). Tripartite motif-containing 29 (TRIM29) is a novel marker for lymph node metastasis in gastric cancer. Ann Surg Oncol 14, 2543-2549.

Logsdon, C. D., Simeone, D. M., Binkley, C., Arumugam, T., Greenson, J. K., Giordano, T. J., Misek, D. E., Kuick, R., and Hanash, S. (2003). Molecular profiling of pancreatic adenocarcinoma and chronic pancreatitis identifies multiple genes differentially regulated in pancreatic cancer. Cancer Res 63, 2649-2657.

Lowe, A. W., Olsen, M., Hao, Y., Lee, S. P., Taek Lee, K., Chen, X., van de Rijn, M., and Brown, P. O. (2007). Gene expression patterns in pancreatic tumors, cells and tissues. PLoS ONE 2, e323.

Lustig, B., and Behrens, J. (2003). The Wnt signaling pathway and its role in tumor development. J Cancer Res Clin Oncol 129, 199-221.

Miyazaki K, Fujita T, Ozaki T, Kato C, Kurose Y, Sakamoto M, Kato S, Goto T, Itoyama Y, Aoki M, et al. (2004). NEDL1, a novel ubiquitin-protein isopeptide ligase for disheveled-1, targets mutant superoxide dismutase-1. J Biol Chem 279, 11327-11335.

Mutter, G. L., Baak, J. P., Fitzgerald, J. T., Gray, R., Neuberg, D., Kust, G. A., Gentleman, R., Gullans, S. R., Wei, L. J., and Wilcox, M. (2001). Global expression changes of constitutive and hormonally regulated genes during endometrial neoplastic transformation. Gynecol Oncol 83, 177-185.

Nacht M, Ferguson A T, Zhang W, et al. (1999). Combining serial analysis of gene expression and array technologies to identify genes differentially expressed in breast cancer. Cancer Res 59, 5464-5470.

Ohmachi, T., Tanaka, F., Mimori, K., Inoue, H., Yanaga, K., and Mori, M. (2006). Clinical significance of TROP2 expression in colorectal cancer. Clin Cancer Res 12, 3057-3063.

Pasca di Magliano, M., Biankin, A. V., Heiser, P. W., Cano, D. A., Gutierrez, P. J., Deramaudt, T., Segara, D., Dawson, A., C., Kench, J. G., Henshall, S. M., et al. (2007). Common activation of canonical wnt signaling in pancreatic adenocarcinoma. PLoS ONE 2, e1155.

Reymond, A., Meroni, G., Fantozzi, A., Merla, G., Cairo, S., Luzi, L., Riganelli, D., Zanaria, E., Messali, S., Cainarca, S., et al. (2001). The tripartite motif family identifies cell compartments. Embo J 20, 2140-2151.

Santin, A. D., Zhan, F., Bellone, S., Palmieri, M., Cane, S., Bignotti, E., Anfossi, S., Gokden, M., Dunn, D., Roman, J. J., et al. (2004). Gene expression profiles in primary ovarian serous papillary tumors and normal ovarian epithelium: identification of candidate molecular markers for ovarian cancer diagnosis and therapy. Int J Cancer 112, 14-25.

Savitsky, K., Bar-Shira, A., Gilad, S., Rotman, G., Ziv, Y., Vanagaite, L., Tagle, D. A., Smith, S., Uziel, T., Sfez, S., et al. (1995). A single ataxia telangiectasia gene with a product similar to PI-3 kinase. Science 268, 1749-1753.

Simons M, Gloy J, Ganner A, Bullerkotte A, Bashkurov M, Kronig C, Schermer B, Benzing T, cabello O A, Jenny A, et al. (2005). Inversin, the gene product mutated in nephronophthisis type II, functions as a molecular switch between Wnt signaling pathways. Nature Genetics 37, 537-543.

Smith, A. P., Hoek, K., and Becker, D. (2005). Whole-genome expression profiling of the melanoma progression pathway reveals marked molecular differences between nevi/melanoma in situ and advanced-stage melanomas. Cancer Biol Ther 4, 1018-1029.

Stremlau, M., Owens, C. M., Perron, M. J., Kiessling, M., Autissier, P., and Sodroski, J. (2004). The cytoplasmic body component TRIM5alpha restricts HIV-1 infection in Old World monkeys. Nature 427, 848-853.

Tauchi, H., Green, C., Knapp, M., Laderoute, K., and Kapp, L. (2000). Altered splicing of the ATDC message in ataxia telangiectasia group D cells results in the absence of a functional protein. Mutagenesis 15, 105-108.

van Noort, M., Meeldijk, J., van der Zee, R., Destree, O., and Clevers, H. (2002). Wnt signaling controls the phosphorylation status of beta-catenin. J Biol Chem 277, 17901-17905.

Winer I S, Bommer G T, Gonik N, and Fearon, E R. (2006) Lysine residues Lys-19 and Lys-49 of b-catenin regulate its levels and function in T cell factor transcriptional activation and neoplastic transformation. J Biol Chem 281, 26181-26187.

Zhan, F., Hardin, J., Kordsmeier, B., Bumm, K., Zheng, M., Tian, E., Sanderson, R., Yang, Y., Wilson, C., Zangari, M., et al. (2002). Global gene expression profiling of multiple myeloma, monoclonal gammopathy of undetermined significance, and normal bone marrow plasma cells. Blood 99, 1745-1757.

Zeng, G, Germinaro M, Micsenyi A, Monga N K, Bell A, Sood A, Malhotra V, Sood N, Midda V, Monga D K, Kokkinakis D M, Monga S P S (2006). Aberrant Wnt/b-catenin signaling in pancreatic adenocarcinoma. Neoplasia 8, 279-289.

Zhang, L., Duan, C. J., Binkley, C., Li, G., Uhler, M. D., Logsdon, C. D., and Simeone, D. M. (2004). A transforming growth factor beta-induced Smad3/Smad4 complex directly activates protein kinase A. Mol Cell Biol 24, 2169-2180.

Zhang, P., Zhang, Z., Zhou, X., Qiu, W., Chen, F., and Chen, W. (2006). Identification of genes associated with cisplatin resistance in human oral squamous cell carcinoma cell line. BMC Cancer 6, 224.

All references, publications, patents, and patent applications mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for treating a human subject with pancreatic cancer comprising: administering an agent that inhibits human ATDC expression or activity to a human subject that has pancreatic cancer, wherein said agent comprises an oligonucleotide that functions via RNA interference, wherein said oligonucleotide consists of a sequence selected from the group consisting of: SEQ ID NO:38 (miR-34a), SEQ ID NO:24 (miR-34c), SEQ ID NO:43 (miR-296-5p), SEQ ID NO:44 (miR-296-3p), SEQ ID NO:40 (miR-650), SEQ ID NO:16 (miR-299-5p), SEQ ID NO:18 (miR-185), SEQ ID NO:26 (miR-765), SEQ ID NO:20 (miR-522), and SEQ ID NO:30 (miR-362).

2. The method of claim 1, further comprising administering a chemotherapeutic agent to said subject.

3. The method of claim 2, wherein said chemotherapeutic is gemcitabine.

4. The method of claim 1, further comprising: exposing said subject to ionizing-radiation and/or UV light.

5. The method of claim 1, wherein said subject is a human being that has been previously treated with chemotherapy.

6. The method of claim 1, wherein said subject comprises non-tumorigenic pancreatic cancer cells and tumorigenic pancreatic cancer stem cells, and wherein administering said agent kills said non-tumorigenic pancreatic cancer cells, said tumorigenic pancreatic cancer stem cells, or both said non-tumorigenic pancreatic cancer cells and said tumorigenic pancreatic cancer stem cells.

7. A method of inhibiting the increase in β-catenin level, TCF activity, and/or cell proliferation induced by ATDC in pancreatic cancer cells over-expressing ATDC, comprising: contacting a human pancreatic cancer cell over expressing human ATDC with an agent under conditions such that increases in β-catenin levels, TCF activity, and/or cell proliferation induced by ATDC in said pancreatic cancer cell is inhibited, wherein said agent is an oligonucleotide that functions via RNA interference and that is specific for human disheveled 2 (Dvl-2), wherein said oligonucleotide sequence consist of SEQ ID NO: 7 or 9.

8. The method of claim 7, wherein said oligonucleotide is selected from the group consisting of an antisense oligonucleotide, an siRNA, an shRNA, and a miRNA.

9. The method of claim 7, wherein said cancer cell is a non-tumorigenic cancer cell or a tumorigenic cancer stem cell.

* * * * *

SEQUENCE LISTING

```
<160> NUMBER OF SEQ ID NOS: 46

<210> SEQ ID NO 1
<211> LENGTH: 2980
<212> TYPE: DNA
<213> ORGANISM: Homo sapiens

<400> SEQUENCE: 1
gacgcctgcc agaaaggtca cctatcctga accccagcaa gcctgaaaca gctcagccaa      60
gcaccctgcg atggaagctg cagatgcctc caggagcaac gggtcgagcc cagaagccag     120
ggatgcccgg agcccgtcgg gccccagtgg cagcctggag aatggcacca aggctgacgg     180
gaaggatgcc aagaccacca acgggcacgg cggggaggca gctgagggca agagcctggg     240
cagcgccctg aagccagggt aaggtaggag cgccctgttc gcgggcaatg agtggcggcg     300
acccatcatc cagtttgtcg agtccgggga cgacaagaac tccaactact tcagcatgga     360
ctctatggaa ggcaagaggt cgccgtacgc agggctccag ctggggggctg ccaagaagcc     420 acccgttacc tttgccgaaa agggcgagct gcgcaagtcc attttctcgg agtcccggaa     480
gcccacggtg tccatcatgg agcccgggga gacccggcgg aacagctacc ccggggccga     540
cacgggcctt ttttcacggt ccaagtccgg ctccgaggag gtgctgtgcg actcctgcat     600
```

-continued

```
cggcaacaag cagaaggcgg tcaagtcctg cctggtgtgc caggcctcct tctgcgagct      660
gcatctcaag ccccacctgg agggcgccgc cttccgagac caccagctgc tcgagcccat      720
ccctacttgc agtgcccgca agtgtcccgt gcatggcaag acgatggagc tcttctgcca      780
gaccgaccag acctgcatct gctacctttg catgttccag gagcacaaga atcatagcac      840
cgtgacagtg gaggaggcca aggccgagaa ggagacggag ctgtcactgc aaaaggagca      900
gctgcagctc aagatcattg agattgagga tgaagctgag aagtggcaga aggagaagga      960
ccgcatcaag agcttcacca ccaatgagaa ggccatcctg gagcagaact tccgggacct     1020
ggtgcgggac ctggagaagc aaaaggagga agtgagggct cgctggagc agcgggagca      1080 ggatgctgtg gaccaagtga aggtgatcat ggatgctctg gatgagagag ccaaggtgct     1140
gcatgaggac aagcagaccc gggagcagct gcatagcatc agcgactctg tgttgtttct     1200
gcaggaattt ggtgcattga tgagcaatta ctctctcccc ccacccctgc ccacctatca     1260
tgtcctgctg gaggggagg gcctgggaca gtcactaggc aacttcaagg acgacctgct     1320
caatgtatgc atgcgccacg ttgagaagat gtgcaaggcg gacctgagcc gtaacttcat     1380
tgagaggaac cacatggaga acggtggtga ccatcgctat gtgaacaact acacgaacag     1440 cttcggggt gagtggagtg caccggacac catgaagaga tactccatgt acctgacacc      1500
caaaggtggg gtccggacat cataccagcc ctcgtctcct ggccgcttca ccaaggagac     1560
cacccagaag aatttcaaca atctctatgg caccaaaggt aactacacct cccgggtctg     1620
ggagtactcc tccagcattc agaactctga caatgacctg cccgtcgtcc aaggcagctc     1680
ctccttctcc ctgaaaggct atccctccct catgcggagc caaagcccca aggcccagcc     1740
ccagacttgg aaatctggca agcagactat gctgtctcac taccggccat tctacgtcaa     1800
caaaggcaac gggattgggt ccaacgaagc ccccatgagc cctggcggaa ggaacgaggc     1860
gccacacccc tgctcttcct cctgaccctg ctgctcttgc cttctaagct actgtgcttg     1920
tctgggtggg agggagcctg gtcctgcacc tgccctctgc agccctctgc cagcctcttg     1980
ggggcagttc cggcctctcc gacttcccca ctggccacac tccattcaga ctccttccct     2040
gccttgtgac ctcagatggt caccatcatt cctgtgctca gaggccaacc catcacaggg     2100
gtgagatagg ttggggcctg ccctaacccg ccagcctcct cctctcgggc tggatctggg     2160
ggctagcagt gagtacccgc atggtatcag cctgcctctc ccgcccacgc cctgctgtct     2220
ccaggcctat agacgtttct ctccaaggcc ctatccccca atgttgtcag cagatgcctg     2280
gacagcacag ccaccatct cccattcaca tggcccacct cctgcttccc agaggactgg      2340
ccctacgtgc tctctctcgt cctacctatc aatgcccagc atggcagaac ctgcagccct     2400
tggccactgc agatggaaac ctctcagtgt cttgacatca ccctacccag gcggtgggtc     2460
tccaccacag ccactttgag tctgtggtcc ctggagggtg gcttctcctg actggcagga     2520
tgaccttagc caagatattc ctctgttccc tctgctgaga taaagaattc ccttaacatg     2580
atataatcca cccatgcaaa tagctactgg cccagctacc atttaccatt tgcctacaga     2640
atttcattca gtctacactt tggcattctc tctggcgatg gagtgtggct gggctgaccg     2700
caaaaggtgc cttacacact gcccccaccc tcagccgttg ccccatcaga ggctgcctcc     2760
tccttctgat taccccccat gttgcatatc agggtgctca aggattggag aggagacaaa     2820
accaggagca gcacagtggg gacatctccc gtctcaacag ccccaggcct atgggggctc     2880
tggaaggatg ggccagcttg caggggttgg ggagggagac atccagcttg gctttcccc      2940 tttggaataa accattggtc tgtcaaaaaa aaaaaaaaa                            2980
```

-continued

```
<210> SEQ ID NO 2
<211> LENGTH: 446
<212> TYPE: PRT
<213> ORGANISM: Homo sapiens

<400> SEQUENCE: 2

Met Glu Pro Gly Glu Thr Arg Arg Asn Ser Tyr Pro Arg Ala Asp Thr
1               5                   10                  15

Gly Leu Phe Ser Arg Ser Lys Ser Gly Ser Glu Glu Val Leu Cys Asp
            20                  25                  30

Ser Cys Ile Gly Asn Lys Gln Lys Ala Val Lys Ser Cys Leu Val Cys
        35                  40                  45

Gln Ala Ser Phe Cys Glu Leu His Leu Lys Pro His Leu Glu Gly Ala
    50                  55                  60

Ala Phe Arg Asp His Gln Leu Leu Glu Pro Ile Pro Thr Cys Ser Ala
65                  70                  75                  80

Arg Lys Cys Pro Val His Gly Lys Thr Met Glu Leu Phe Cys Gln Thr
                85                  90                  95

Asp Gln Thr Cys Ile Cys Tyr Leu Cys Met Phe Gln Glu His Lys Asn
            100                 105                 110

His Ser Thr Val Thr Val Glu Glu Ala Lys Ala Glu Lys Glu Thr Glu
        115                 120                 125

Leu Ser Leu Gln Lys Glu Gln Leu Gln Leu Lys Ile Ile Glu Ile Glu
    130                 135                 140

Asp Glu Ala Glu Lys Trp Gln Lys Glu Lys Asp Arg Ile Lys Ser Phe
145                 150                 155                 160

Thr Thr Asn Glu Lys Ala Ile Leu Glu Gln Asn Phe Arg Asp Leu Val
                165                 170                 175

Arg Asp Leu Glu Lys Gln Lys Glu Glu Val Arg Ala Ala Leu Glu Gln
            180                 185                 190

Arg Glu Gln Asp Ala Val Asp Gln Val Lys Val Ile Met Asp Ala Leu
        195                 200                 205

Asp Glu Arg Ala Lys Val Leu His Glu Asp Lys Gln Thr Arg Glu Gln
210                 215                 220

Leu His Ser Ile Ser Asp Ser Val Leu Phe Leu Gln Glu Phe Gly Ala
225                 230                 235                 240

Leu Met Ser Asn Tyr Ser Leu Pro Pro Leu Pro Thr Tyr His Val
                245                 250                 255

Leu Leu Glu Gly Glu Gly Leu Gly Gln Ser Leu Gly Asn Phe Lys Asp
            260                 265                 270

Asp Leu Leu Asn Val Cys Met Arg His Val Glu Lys Met Cys Lys Ala
        275                 280                 285

Asp Leu Ser Arg Asn Phe Ile Glu Arg Asn His Met Glu Asn Gly Gly
    290                 295                 300

Asp His Arg Tyr Val Asn Asn Tyr Thr Asn Ser Phe Gly Gly Glu Trp
305                 310                 315                 320

Ser Ala Pro Asp Thr Met Lys Arg Tyr Ser Met Tyr Leu Thr Pro Lys
                325                 330                 335

Gly Gly Val Arg Thr Ser Tyr Gln Pro Ser Ser Pro Gly Arg Phe Thr
            340                 345                 350

Lys Glu Thr Thr Gln Lys Asn Phe Asn Asn Leu Tyr Gly Thr Lys Gly
        355                 360                 365

Asn Tyr Thr Ser Arg Val Trp Glu Tyr Ser Ser Ser Ile Gln Asn Ser
    370                 375                 380
```

```
Asp Asn Asp Leu Pro Val Val Gln Gly Ser Ser Phe Ser Leu Lys
385                 390                 395                 400

Gly Tyr Pro Ser Leu Met Arg Ser Gln Ser Pro Lys Ala Gln Pro Gln
            405                 410                 415

Thr Trp Lys Ser Gly Lys Gln Thr Met Leu Ser His Tyr Arg Pro Phe
            420                 425                 430

Tyr Val Asn Lys Gly Asn Gly Ile Gly Ser Asn Glu Ala Pro
            435                 440                 445

<210> SEQ ID NO 3
<211> LENGTH: 50
<212> TYPE: DNA
<213> ORGANISM: Homo sapiens

<400> SEQUENCE: 3
caccgcgacc catcatccag tttgtcgaaa caaactggat gatgggtcgc            50

<210> SEQ ID NO 4
<211> LENGTH: 50
<212> TYPE: DNA
<213> ORGANISM: Homo sapiens

<400> SEQUENCE: 4
aaaagcgacc catcatccag tttgtttcga caaactggat gatgggtcgc            50

<210> SEQ ID NO 5
<211> LENGTH: 49
<212> TYPE: DNA
<213> ORGANISM: Homo sapiens

<400> SEQUENCE: 5
caccgaagag ctccatcgtc ttgccacgaa tggcaagacg atggagctc             49

<210> SEQ ID NO 6
<211> LENGTH: 49
<212> TYPE: DNA
<213> ORGANISM: Homo sapiens

<400> SEQUENCE: 6
aaaagagctc catcgtcttg ccattcgtgg caagacgatg agctcttc              49

<210> SEQ ID NO 7
<211> LENGTH: 66
<212> TYPE: DNA
<213> ORGANISM: Homo sapiens

<400> SEQUENCE: 7
cacctgtagc tgcctttgtt actctattta tttcgaaaaa taaatagagt aacaaaggca   60
gctaca                                                              66

<210> SEQ ID NO 8
<211> LENGTH: 67
<212> TYPE: DNA
<213> ORGANISM: Homo sapiens

<400> SEQUENCE: 8
aaaatgtagc tgcctttgtt actctattta tttattcgaa ataaatagag taacaaaggc   60
agctaca                                                             67
```

```
<210> SEQ ID NO 9
<211> LENGTH: 66
<212> TYPE: DNA
<213> ORGANISM: Homo sapiens

<400> SEQUENCE: 9
caccggaccg catgtggctc aagatcacca tcccgaagga tggtgatctt gagccacatg      60
cggtcc                                                                 66

<210> SEQ ID NO 10
<211> LENGTH: 65
<212> TYPE: DNA
<213> ORGANISM: Homo sapiens

<400> SEQUENCE: 10
aaaaggaccg cagtggctca agatcaccat ccttcgggat ggtgatcttg agccacatgc      60
ggtcc                                                                  65

<210> SEQ ID NO 11
<211> LENGTH: 50
<212> TYPE: DNA
<213> ORGANISM: Homo sapiens

<400> SEQUENCE: 11
cacccaacaa gatgaagagc accaacgaat tggtgctctt catcttgttg                 50

<210> SEQ ID NO 12
<211> LENGTH: 50
<212> TYPE: DNA
<213> ORGANISM: Homo sapiens

<400> SEQUENCE: 12
cacccaacaa gatgaagagc accaacgaat tggtgctctt catcttgttg                 50

<210> SEQ ID NO 13
<211> LENGTH: 3046
<212> TYPE: DNA
<213> ORGANISM: Homo sapiens

<400> SEQUENCE: 13
agtcacgtga catgaggaga ggtgggcggg tacctggagg aagctcgcgg cgtcggtggc      60
ggtggcgcgc ggcggccgct gagaccgggg cttttgagtcg caccccgcgg cccgcccccc   120
gccgccaccc tcgcagatcc gtgctttttc cctttgctt ctctcccgta ctgggtcagt     180
cctgtccgcg ctcgcgcgtc ggtttgcggg tgtgcgcagg cgcggcaggg gccattagcc    240
ctttgggtgg gcggtggagc ccgggagcgc gcggcgaga ccatggcggg tagcagcact      300
gggggcggtg gggttgggga acgaaggtg atttaccacc tggatgagga agagactccc      360
tacctggtga agatccctgt ccccgccgag cgcatcaccc tcggcgattt caagagcgtc      420
ctgcagcggc ccgcgggcgc caagtacttt ttcaagtcta tggatcagga tttcggggtg      480
gtgaaggaag aaatttcaga tgacaacgcc cgcctcccct gcttcaacgg aagggtggta      540
tcctggctgg tgtcctcaga taatccccaa cccgagatgg cccctccagt ccatgagcct      600
cgggcagaac tggcgcctcc agccccacct ttacctcctt tgccacccga ggaccagc       660 ggcattgggg actcaaggcc tccatccttc caccctaatg tgtccagcag ccatgagaat      720
ctggagcctg agacagaaac cgagtcagta gtgtcactga gcggggagcg gcctcgcagg      780
agagacagca gtgagcatgg cgctgggggc cacaggactg tggcccctc aaggctggag       840 cgccacctgg ccggatacga gagctcctct accctcatga ccagcgagct ggagagtacc      900
```

| | |
|---|---|
| agcctgggggg actcggacga ggaggacacc atgagcaggt tcagcagctc cacggagcag | 960 |
| agcagtgcct cccgcctcct taagcgccac cggcggcgaa ggaagcagag gccacccccgc | 1020 |
| ctggagagga cgtcatcctt cagcagcgtc acagattcca caatgtctct caatatcatc | 1080 |
| acagtcacgc taaacatgga gaagtacaac ttcctgggta tctccattgt tggccagagc | 1140 |
| aatgagcggg gagacggagg catctacatt ggctccatca tgaagggtgg ggctgtggcg | 1200 |
| gccgacgggc gcattgagcc aggggacatg cttttgcagg tgaatgacat gaactttgag | 1260 |
| aacatgagca acgatgacgc tgtgcgggtg ctgagggaca ttgtgcacaa gcctggcccc | 1320 |
| attgtgctga ctgtggccaa gtgctgggat ccctctcctc aggcctattt cactctcccc | 1380 |
| cgaaatgagc ccatccagcc aattgaccct gctgcctggg tgtcccattc cgcggctctg | 1440 |
| actggcacct tcccagccta tccaggttcc tcctccatga gcaccattac atctggatcg | 1500 |
| tctttgcctg atggctgtga aggccggggt ctctccgtcc atacggacat ggcatcggtg | 1560 |
| accaaggcca tggcagctcc agagtctgga ctggaagtcc gggaccgcat gtggctcaag | 1620 |
| atcaccatcc ctaatgcctt tctgggctcg gatgtggttg actggctcta ccatcacgtg | 1680 |
| gagggctttc ctgagcggcg ggaggcccgc aagtatgcca gcgggctgct caaagcaggc | 1740 |
| ctgatccgac acaccgtcaa caagatcacc ttctctgagc agtgctatta cgtcttcgga | 1800 |
| gacctcagtg gtggctgtga gagctaccta gtcaacctgt ctctcaatga caacgatggc | 1860 |
| tccagtgggg cttcagacca ggataccctg gctcctctgc ctggggccac ccctggccc | 1920 |
| ctgctgccca ctttctccta ccaataccct gccccacacc cctacagccc gcagcctcca | 1980 |
| ccctaccatg agctttcatc ttacacctat ggtggggca gtgccagcag ccagcatagt | 2040 |
| gagggcagcc ggagcagtgg gtcgacacgg agtgatgggg gggcagggcg cacggggagg | 2100 |
| cccgaggagc gggcccccga gtccaagtcc ggcagtggca gtgagtctga gccctccagc | 2160 |
| cgaggggca gccttcggcg gggtggggaa gcaagtggga ctagcgatgg gggccctcct | 2220 |
| ccatccagag gctcaactgg gggtgcccct aatctccgag cccacccagg gctccatccc | 2280 |
| tatggaccgc cccctggcat ggccctcccc tacaacccca tgatggtggt catgatgccc | 2340 |
| ccacctccac ctccagtccc tccagcagtg cagcctccgg ggggccctcc agtcagagac | 2400 |
| ctgggctctg tgcccccaga actgacagcc agccgccaaa gcttccacat ggccatgggc | 2460 |
| aatcccagcg agttctttgt ggatgttatg tagcccactg tggggccagg ctgggccggg | 2520 |
| cgctcctggt gtgtgactgg gtgtcctggc cgtcatgtgc ttgctcttac agtgcctggg | 2580 |
| ctcagcctac cagctgctgc catacaggag attgtggcca ctgtgactct caccagcagt | 2640 |
| gcctggttcc tcccccttcc ctcagggta gacaagggac ctttgattat ttttagcttt | 2700 |
| gttttttat aagccttttt ggggttaaa atagagtttc ttacattttt gggactttt | 2760 |
| taataggcat ttcctctttt atatgaagaa ttcccatcca ttgggcccct tctaacccca | 2820 |
| gaatgtgacc tcctcctcca gttacccaca gcccctgccct ttgcagggtt gggggtggtc | 2880 |
| agcggtaccc cggggttagg catcctagac agcagcctga ggaagctggg agatttgggc | 2940 |
| catgtagctg cctttgttac tctatttatt ttagtcactt gtataaaaca ccaaataaag | 3000 |
| caatagaggc aaactcaaaa aaaaaaaaaa aaaaaaaaaa aaaaa | 3046 |

<210> SEQ ID NO 14
<211> LENGTH: 1146
<212> TYPE: DNA
<213> ORGANISM: Homo sapiens -continued

```
<400> SEQUENCE: 14
gctcctggcg gaaggaacga ggcgccacac ccctgctctt cctcctgacc ctgctgctct       60
tgccttctaa gctactgtgc ttgtctgggt gggagggagc ctggtcctgc acctgccctc      120
tgcagccctc tgccagcctc ttgggggcag ttccggcctc tccgacttcc ccactggcca      180
cactccattc agactccttt cctgccttgt gacctcagat ggtcaccatc attcctgtgc      240
tcagaggcca acccatcaca ggggtgagat aggttgggc ctgccctaac ccgccagcct      300
cctcctctcg ggctggatct gggggctagc agtgagtacc cgcatggtat cagcctgcct      360
ctcccgccca cgccctgctg tctccaggcc tatagacgtt tctctccaag gcccatccc      420
ccaatgttgt cagcagatgc ctggacagca cagccaccca tctcccattc acatggccca      480
cctcctgctt cccagaggac tggccctacg tgctctctct cgtcctacct atcaatgccc      540
agcatggcag aacctgcagc ccttggccac tgcagatgga aacctctcag tgtcttgaca      600
tcacccctacc caggcggtgg gtctccacca cagccacttt gagtctgtgg tccctggagg      660
gtggcttctc ctgactggca ggatgacctt agccaagata ttcctctgtt ccctctgctg      720
agataaagaa ttcccttaac atgatataat ccacccatgc aaatagctac tggcccagct      780
accatttacc atttgcctac agaatttcat tcagtctaca ctttggcatt ctctctggcg      840
atggagtgtg gctgggctga ccgcaaaagg tgccttacac actgccccca ccctcagccg      900
ttgcccccatc agaggctgcc tcctccttct gattacccccc catgttgcat atcagggtgc      960
tcaaggattg gagaggagac aaaaccagga gcagcacagt ggggacatct cccgtctcaa     1020
cagccccagg cctatggggg ctctggaagg atgggccagc ttgcaggggt tggggaggga     1080
gacatccagc ttgggctttc cccttttggaa taaaccattg gtctgtcaaa aaaaaaaaaa     1140
aaaaaa                                                                1146

<210> SEQ ID NO 15
<211> LENGTH: 23
<212> TYPE: RNA
<213> ORGANISM: Homo sapiens

<400> SEQUENCE: 15 cuuucccuu uggaauaaac cau                                                23

<210> SEQ ID NO 16
<211> LENGTH: 22
<212> TYPE: RNA
<213> ORGANISM: Homo sapiens

<400> SEQUENCE: 16
uacauacacc cugccauuug gu                                                22

<210> SEQ ID NO 17
<211> LENGTH: 23
<212> TYPE: RNA
<213> ORGANISM: Homo sapiens

<400> SEQUENCE: 17
aggccuauag acguuucucu cca                                               23

<210> SEQ ID NO 18
<211> LENGTH: 18
<212> TYPE: RNA
<213> ORGANISM: Homo sapiens
```

```
<400> SEQUENCE: 18
cuugacggaa agagaggu                                                      18

<210> SEQ ID NO 19
<211> LENGTH: 23
<212> TYPE: RNA
<213> ORGANISM: Homo sapiens

<400> SEQUENCE: 19
gcuacuggcc cagcuaccau uua                                                23

<210> SEQ ID NO 20
<211> LENGTH: 23
<212> TYPE: RNA
<213> ORGANISM: Homo sapiens

<400> SEQUENCE: 20
uugugagauu ucccuuggua aaa                                                23

<210> SEQ ID NO 21
<211> LENGTH: 23
<212> TYPE: RNA
<213> ORGANISM: Homo sapiens

<400> SEQUENCE: 21
ggcugaccgc aaaaggugcc uua                                                23

<210> SEQ ID NO 22
<211> LENGTH: 21
<212> TYPE: RNA
<213> ORGANISM: Homo sapiens

<400> SEQUENCE: 22
agaugagucu ucccacggaa u                                                  21

<210> SEQ ID NO 23
<211> LENGTH: 23
<212> TYPE: RNA
<213> ORGANISM: Homo sapiens

<400> SEQUENCE: 23
aaaaggugcc uuacacacug ccc                                                23

<210> SEQ ID NO 24
<211> LENGTH: 23
<212> TYPE: RNA
<213> ORGANISM: Homo sapiens

<400> SEQUENCE: 24
cguuagucga uugaugugac gga                                                23

<210> SEQ ID NO 25
<211> LENGTH: 23
<212> TYPE: RNA
<213> ORGANISM: Homo sapiens

<400> SEQUENCE: 25
cccaucagag gcugccuccu ccu                                                23

<210> SEQ ID NO 26
<211> LENGTH: 21
<212> TYPE: RNA
<213> ORGANISM: Homo sapiens
```

```
<400> SEQUENCE: 26
guaguggaag gaagaggagg u                                           21

<210> SEQ ID NO 27
<211> LENGTH: 23
<212> TYPE: RNA
<213> ORGANISM: Homo sapiens

<400> SEQUENCE: 27
cccuaacccg ccagccuccu ccu                                         23

<210> SEQ ID NO 28
<211> LENGTH: 21
<212> TYPE: RNA
<213> ORGANISM: Homo sapiens

<400> SEQUENCE: 28
guaguggaag gaagaggagg u                                           21

<210> SEQ ID NO 29
<211> LENGTH: 23
<212> TYPE: RNA
<213> ORGANISM: Homo sapiens

<400> SEQUENCE: 29
gcauaucagg gugcucaagg auu                                         23

<210> SEQ ID NO 30
<211> LENGTH: 24
<212> TYPE: RNA
<213> ORGANISM: Homo sapiens

<400> SEQUENCE: 30
ugagugugga uccaagguuc cuaa                                        24

<210> SEQ ID NO 31
<211> LENGTH: 23
<212> TYPE: RNA
<213> ORGANISM: Homo sapiens

<400> SEQUENCE: 31
cagggugcuc aaggauugga gag                                         23

<210> SEQ ID NO 32
<211> LENGTH: 24
<212> TYPE: RNA
<213> ORGANISM: Homo sapiens

<400> SEQUENCE: 32
gucuuucacg aaagaaaacc ucuu                                        24

<210> SEQ ID NO 33
<211> LENGTH: 23
<212> TYPE: RNA
<213> ORGANISM: Homo sapiens

<400> SEQUENCE: 33
ucccgucuca acagccccag gcc                                         23

<210> SEQ ID NO 34
<211> LENGTH: 24
<212> TYPE: RNA
<213> ORGANISM: Homo sapiens
```

```
<400> SEQUENCE: 34
ugcgcguccg gucucugggu ccgu                                         24

<210> SEQ ID NO 35
<211> LENGTH: 23
<212> TYPE: RNA
<213> ORGANISM: Homo sapiens

<400> SEQUENCE: 35
ccaggccuau gggggcucug gaa                                          23

<210> SEQ ID NO 36
<211> LENGTH: 21
<212> TYPE: RNA
<213> ORGANISM: Homo sapiens

<400> SEQUENCE: 36
ucuuucacgu agggagaccu c                                            21

<210> SEQ ID NO 37
<211> LENGTH: 23
<212> TYPE: RNA
<213> ORGANISM: Homo sapiens

<400> SEQUENCE: 37
aaaaggugcc uuacacacug ccc                                          23

<210> SEQ ID NO 38
<211> LENGTH: 23
<212> TYPE: RNA
<213> ORGANISM: Homo sapiens

<400> SEQUENCE: 38
uuguuggucg auucugugac ggu                                          23

<210> SEQ ID NO 39
<211> LENGTH: 23
<212> TYPE: RNA
<213> ORGANISM: Homo sapiens

<400> SEQUENCE: 39
ugccccauca gaggcugccu ccu                                          23

<210> SEQ ID NO 40
<211> LENGTH: 21
<212> TYPE: RNA
<213> ORGANISM: Homo sapiens

<400> SEQUENCE: 40
caggacucuc gcgacggagg a                                            21

<210> SEQ ID NO 41
<211> LENGTH: 16
<212> TYPE: RNA
<213> ORGANISM: Homo sapiens

<400> SEQUENCE: 41
auguucccaa cccucu                                                  16

<210> SEQ ID NO 42
<211> LENGTH: 19
<212> TYPE: RNA
<213> ORGANISM: Homo sapiens
```

```
<400> SEQUENCE: 42
ugcucaagga uuggagagg                                            19

<210> SEQ ID NO 43
<211> LENGTH: 21
<212> TYPE: RNA
<213> ORGANISM: Homo sapiens

<400> SEQUENCE: 43
agggcccccc cucaauccug u                                         21

<210> SEQ ID NO 44
<211> LENGTH: 22
<212> TYPE: RNA
<213> ORGANISM: Homo sapiens

<400> SEQUENCE: 44
gaggguuggg uggaggcucu cc                                        22

<210> SEQ ID NO 45
<211> LENGTH: 21
<212> TYPE: DNA
<213> ORGANISM: Homo sapiens

<400> SEQUENCE: 45
caaggacgac ctgctcaatg t                                         21

<210> SEQ ID NO 46
<211> LENGTH: 20
<212> TYPE: DNA
<213> ORGANISM: Homo sapiens

<400> SEQUENCE: 46
cgatggtcac caccgttctc                                           20
```